(12) United States Patent
Rajagopal et al.

(10) Patent No.: US 11,877,928 B2
(45) Date of Patent: Jan. 23, 2024

(54) TRANSCATHETER ANCHOR SUPPORT AND METHODS OF IMPLANTATION

(71) Applicant: OPUS MEDICAL THERAPIES, LLC, Atlanta, GA (US)

(72) Inventors: Vivek Rajagopal, Atlanta, GA (US); Jaime Eduardo Sarabia, Mableton, GA (US); Yenchin Liao, Cary, CO (US)

(73) Assignee: OPUS MEDICAL THERAPIES, LLC, Atlanta, GA (US)

( * ) Notice: Subject to any disclaimer, the term of this patent is extended or adjusted under 35 U.S.C. 154(b) by 221 days.

(21) Appl. No.: 17/490,924

(22) Filed: Sep. 30, 2021

(65) Prior Publication Data

US 2022/0104941 A1 Apr. 7, 2022

Related U.S. Application Data

(60) Provisional application No. 63/086,582, filed on Oct. 1, 2020.

(51) Int. Cl.
*A61F 2/24* (2006.01)

(52) U.S. Cl.
CPC .......... *A61F 2/2427* (2013.01); *A61F 2/2466* (2013.01); *A61F 2220/0016* (2013.01); *A61F 2220/0075* (2013.01); *A61F 2230/0091* (2013.01)

(58) Field of Classification Search
CPC ........ A61F 2/24; A61F 2/2427; A61F 2/2487; A61F 2002/249; A61B 17/0401; A61B 2017/048; A61B 2017/0487
See application file for complete search history.

(56) References Cited

U.S. PATENT DOCUMENTS

| | | | |
|---|---|---|---|
| 4,242,715 | A | 12/1980 | Gerald |
| 4,337,496 | A | 6/1982 | Gerald |
| 4,746,057 | A | 5/1988 | Wagner |
| 4,830,360 | A | 5/1989 | Carr, Jr. |
| 5,079,776 | A | 1/1992 | Crawford |
| 5,312,438 | A | 5/1994 | Johnson |

(Continued)

FOREIGN PATENT DOCUMENTS

| | | |
|---|---|---|
| AU | 2016202264 A1 | 11/2016 |
| CA | 3059102 A1 | 10/2018 |

(Continued)

OTHER PUBLICATIONS

International Search Report issued in corresponding International Application No. PCT/US2021/052954 dated Dec. 22, 2021.

(Continued)

*Primary Examiner* — Seema Mathew
(74) *Attorney, Agent, or Firm* — FisherBroyles LLP; Rachel Huffstetler

(57) ABSTRACT

A minimally invasively implanted anchor support for securing a medical prosthesis device with a tether to an implanted anchor. The anchor support includes a lock cap for connecting to the anchor, a tether swivel connected to the lock cap, a tock cone within the tether swivel and a tether collar on a proximal end of the tether swivel. An anchor support delivery system cooperates with the anchor support for securing to the lock cap.

58 Claims, 40 Drawing Sheets

(56) References Cited

U.S. PATENT DOCUMENTS

| | | | |
|---|---|---|---|
| 5,683,451 A | 11/1997 | Lenker | |
| 5,706,520 A | 1/1998 | Thornton | |
| 6,093,162 A | 7/2000 | Fairleigh | |
| 7,530,995 B2 | 5/2009 | Quijano | |
| 7,780,725 B2 | 8/2010 | Haug | |
| 8,147,542 B2 | 4/2012 | Maisano | |
| 8,236,049 B2 | 8/2012 | Rowe | |
| 8,252,050 B2 | 8/2012 | Maisano | |
| 8,273,973 B2 | 9/2012 | Kimmons | |
| 8,333,155 B2 | 12/2012 | Cylvick | |
| 8,403,983 B2 | 3/2013 | Quadri | |
| 8,449,599 B2 | 5/2013 | Chau | |
| 8,489,165 B2 | 7/2013 | Segman | |
| 8,545,553 B2 | 10/2013 | Zipory | |
| 8,549,175 B2 | 10/2013 | Krishna | |
| 8,690,939 B2 | 4/2014 | Miller | |
| 8,728,155 B2 | 5/2014 | Montorfano | |
| 8,790,394 B2 | 7/2014 | Miller | |
| 8,888,843 B2 | 11/2014 | Khairkhahan | |
| 8,900,295 B2 | 12/2014 | Migliazza | |
| 8,932,348 B2 | 1/2015 | Solem | |
| 8,998,976 B2 | 4/2015 | Gregg | |
| 9,005,084 B2 | 4/2015 | Silagy | |
| 9,033,383 B2 | 5/2015 | Rampersad | |
| 9,034,033 B2 | 5/2015 | McLean | |
| 9,078,749 B2 | 7/2015 | Lutter | |
| 9,375,312 B2 | 6/2016 | Weber | |
| 9,439,763 B2 | 9/2016 | Geist | |
| 9,441,832 B2 | 9/2016 | Bushee | |
| 9,474,605 B2 | 10/2016 | Rowe | |
| 9,480,559 B2 | 11/2016 | Robert | |
| 9,486,306 B2 | 11/2016 | Tegels | |
| 9,578,982 B2 | 2/2017 | Rampersad | |
| 9,827,092 B2 | 11/2017 | Robert | |
| 9,849,001 B2 | 12/2017 | Thompson, Jr. | |
| 9,877,833 B1 * | 1/2018 | Bishop | A61F 2/2457 |
| 9,895,221 B2 | 2/2018 | Robert | |
| 9,986,993 B2 | 6/2018 | Vidlund | |
| 10,039,639 B2 | 8/2018 | Marchand | |
| 10,219,900 B2 | 3/2019 | Vidlund | |
| 2004/0049207 A1 * | 3/2004 | Goldfarb | A61B 17/1227 606/139 |
| 2004/0116992 A1 | 6/2004 | Wardle | |
| 2004/0190383 A1 | 9/2004 | Marcucelli | |
| 2005/0137697 A1 | 6/2005 | Salahieh | |
| 2006/0235509 A1 | 10/2006 | Lafontaine | |
| 2006/0241656 A1 | 10/2006 | Starksen | |
| 2006/0241745 A1 | 10/2006 | Solem | |
| 2007/0049980 A1 | 3/2007 | Zielinski | |
| 2007/0066863 A1 | 3/2007 | Rafiee | |
| 2007/0073351 A1 | 3/2007 | Zielinski | |
| 2007/0118151 A1 | 5/2007 | Davidson | |
| 2007/0265658 A1 * | 11/2007 | Nelson | A61B 17/0469 606/213 |
| 2007/0277279 A1 | 12/2007 | Battat | |
| 2008/0125860 A1 | 5/2008 | Webler | |
| 2009/0012557 A1 | 1/2009 | Osypka | |
| 2009/0276040 A1 | 11/2009 | Rowe | |
| 2010/0016655 A1 | 1/2010 | Annest | |
| 2010/0161041 A1 | 6/2010 | Maisano | |
| 2011/0004296 A1 | 1/2011 | Lutter | |
| 2011/0112737 A1 | 5/2011 | Neelakantan | |
| 2011/0312018 A1 | 12/2011 | Shusta | |
| 2012/0078360 A1 | 3/2012 | Rafiee | |
| 2012/0136430 A1 | 5/2012 | Sochman | |
| 2013/0023985 A1 | 1/2013 | Khairkhahan | |
| 2013/0172978 A1 | 7/2013 | Robert | |
| 2013/0184811 A1 | 7/2013 | Rowe | |
| 2013/0190861 A1 | 7/2013 | Chau | |
| 2013/0211508 A1 | 8/2013 | Lane | |
| 2013/0304197 A1 | 11/2013 | Buchbinder | |
| 2013/0331929 A1 | 12/2013 | Mitra | |
| 2014/0005778 A1 | 1/2014 | Buchbinder | |
| 2014/0031928 A1 | 1/2014 | Murphy | |
| 2014/0163668 A1 | 6/2014 | Rafiee | |
| 2014/0296972 A1 | 10/2014 | Tegels | |
| 2014/0316516 A1 | 10/2014 | Vidlund | |
| 2014/0379076 A1 | 12/2014 | Vidlund | |
| 2015/0142103 A1 | 5/2015 | Vidlund | |
| 2015/0157268 A1 | 6/2015 | Winshtein | |
| 2015/0250590 A1 | 9/2015 | Gries | |
| 2015/0305861 A1 * | 10/2015 | Annest | A61F 2/2427 623/2.11 |
| 2015/0342602 A1 | 12/2015 | Jimenez | |
| 2015/0366666 A1 | 12/2015 | Khairkhahan | |
| 2016/0022501 A1 | 1/2016 | Schultz | |
| 2016/0067395 A1 | 3/2016 | Jimenez | |
| 2016/0120646 A1 | 5/2016 | Dwork | |
| 2016/0213467 A1 | 7/2016 | Backus | |
| 2016/0262878 A1 | 9/2016 | Backus | |
| 2016/0262881 A1 | 9/2016 | Schankereli | |
| 2016/0310268 A1 | 10/2016 | Oba | |
| 2016/0317305 A1 | 11/2016 | Pelled | |
| 2016/0324635 A1 | 11/2016 | Vidlund | |
| 2016/0367360 A1 | 12/2016 | Cartledge | |
| 2016/0367368 A1 * | 12/2016 | Vidlund | A61F 2/2487 |
| 2017/0143478 A1 | 5/2017 | Schwartz | |
| 2017/0209293 A1 | 7/2017 | Combs | |
| 2017/0227320 A1 | 8/2017 | Derousse | |
| 2018/0085215 A1 | 3/2018 | Vaturi | |
| 2018/0140421 A1 * | 5/2018 | Sampson | A61B 17/0401 |
| 2018/0289473 A1 | 10/2018 | Rajagopal | |
| 2018/0289474 A1 * | 10/2018 | Rajagopal | A61F 2/2418 |
| 2018/0289485 A1 | 10/2018 | Rajagopal | |
| 2018/0318071 A1 | 11/2018 | Lozonschi | |
| 2019/0015205 A1 * | 1/2019 | Rajagopal | A61B 18/1492 |
| 2020/0001135 A1 | 1/2020 | Rajagopal | |
| 2020/0069426 A1 * | 3/2020 | Conklin | A61F 2/2481 |
| 2020/0078000 A1 * | 3/2020 | Rajagopal | A61F 2/2409 |
| 2020/0178977 A1 * | 6/2020 | Coleman | A61B 17/12109 |
| 2020/0330228 A1 | 10/2020 | Anderson | |
| 2020/0397571 A1 | 12/2020 | Rajagopal | |
| 2021/0093454 A1 * | 4/2021 | Sampson | A61F 2/2487 |
| 2021/0220130 A1 | 7/2021 | Rajagopal | |
| 2022/0104941 A1 * | 4/2022 | Rajagopal | A61F 2/2466 |

FOREIGN PATENT DOCUMENTS

| | | |
|---|---|---|
| CA | 3059106 A1 | 10/2018 |
| CN | 103826750 A | 5/2014 |
| CN | 106618798 A | 5/2017 |
| CN | 105658178 B | 5/2018 |
| DE | 102012002785 A1 | 8/2013 |
| EP | 1462880 A2 | 9/2004 |
| EP | 1462880 A3 | 4/2005 |
| EP | 3311774 A1 | 4/2018 |
| KR | 20200007805 | 1/2020 |
| KR | 20200007806 | 1/2020 |
| NO | 2018187390 A1 | 10/2018 |
| UY | 37667 A | 10/2018 |
| UY | 37668 A | 10/2018 |
| WO | 1994020049 A1 | 9/1994 |
| WO | 2005094711 A2 | 10/2005 |
| WO | 2014021905 A1 | 2/2014 |
| WO | 2016050751 A1 | 4/2016 |
| WO | 2016179427 A1 | 11/2016 |
| WO | 2016186909 A1 | 11/2016 |
| WO | 098100 S | 6/2017 |
| WO | 2017117560 A1 | 7/2017 |
| WO | 2018187495 A1 | 10/2018 |
| WO | 2020005527 A1 | 1/2020 |

OTHER PUBLICATIONS

Bai Y, Chen HY, Zong GJ, et al. Percutaneous establishment of tricuspid regurgitation: an experimental model for transcatheter tricuspid valve replacement. Chinese medical journal 2010;123:806-9.

Boudjemline Y, Agnoletti G, Bonnet D, et al. Steps toward the percutaneous replacement of atrioventricular valves an experimental study. Journal of the American College of Cardiology 2005;46:360-5.

(56) References Cited

OTHER PUBLICATIONS

Cao R Catheter-Based Tricuspid Valve Replacement via Right Atrium: An Animal Experimental Study. Transcatheter Cardiovascular Therapeutics; 2017; Denver, Colorado.

Figulla HR, Kiss K, Lauten A. Transcatheter interventions for tricuspid regurgitation—heterotopic technology: TricValve. EuroIntervention : journal of EuroPCR in collaboration with the Working Group on Interventional Cardiology of the European Society of Cardiology 2016;12:Y116-8.

Hahn RT, Meduri CU, Davidson CJ, et al. Early Feasibility Study of a Transcatheter Tricuspid Valve Annuloplasty: SCOUT Trial 30-Day Results. Journal of the American College of Cardiology 2017;69:1795-806.

International Preliminary Report on Patentability received for PCT Application Serial No. PCT/US2018/025971 dated Oct. 17, 2019, 9 pages.

International Preliminary Report on Patentability received for PCT Application Serial No. PCT/US2018/026118 dated Oct. 17, 2019, 11 pages.

International Search Report and Written Opinion in corresponding International application No. PCT/PCT/US2018/026118 dated Jun. 15, 2018.

International Search Report and Written Opinion in corresponding International application No. PCT/US2018/025971 dated Jul. 10, 2018.

International Search Report and Written Opinion in corresponding International application No. PCT/US2021/014644 dated Apr. 9, 2021.

International Search Report and Written Opinion issued in corresponding International Application No. PCT/US2019/057145 dated Dec. 31, 2019.

International Search Report and Written Opinion of the International Searching Authority dated Aug. 30, 2019, in International Application No. PCT/US19/36428.

Kuwata S, Taramasso M, Nietlispach F, Maisano F. Transcatheter tricuspid valve repair toward a surgical standard: first-in-man report of direct annuloplasty with a cardioband device to treat severe functional tricuspid regurgitation. European heart journal 2017.

Laule M, Stangl V, Sanad W, Lembcke A, Baumann G, Stangl K. Percutaneous transfemoral management of severe secondary tricuspid regurgitation with Edwards Sapien XT bioprosthesis: first-in-man experience. Journal of the American College of Cardiology 2013;61:1929-31.

Lauten A, Doenst T, Hamadanchi A, Franz M, Figulla HR. Percutaneous bicaval valve implantation for transcatheter treatment of tricuspid regurgitation: clinical observations and 12-month follow-up. Circulation Cardiovascular Interventions 2014,7:268-72.

Lauten A, Ferrari M, Hekmat K, et al. Heterotopic transcatheter tricuspid valve implantation: first-in-man application of a novel approach to tricuspid regurgitation. European heart journal 2011;32:1207-13.

Lauten A, Figulla HR, Unbehaun A, et al. Interventional Treatment of Severe Tricuspid Regurgitation: Early Clinical Experience in a Multicenter, Observational, First-in-Man Study. Circulation Cardiovascular interventions 2018;11:e006061.

Lauten A, Figulla HR, Willich C, et al. Percutaneous caval stent valve implantation: investigation of an interventional approach for treatment of tricuspid regurgitation. European heart journal 2010;31:1274-81.

Lauten A, Laube A, Schubert H, et al. Transcatheter treatment of tricuspid regurgitation by caval valve implantation—experimental evaluation of decellularized tissue valves in central venous position. Catheterization and cardiovascular Interventions : official journal of the Society for Cardiac Angiography & Interventions 2014.

Navia JL, Kapadia S, Elgharably H, et al. First-in-Human Implantations of the NaviGate Bioprosthesis in a Severely Dilated Tricuspid Annulus and in a Failed Tricuspid Annuloplasty Ring. Circulation Cardiovascular interventions 2017;10.

Nickenig G, Kowalski M, Hausleiter J, et al. Transcatheter Treatment of Severe Tricuspid Regurgitation With the Edge-to-Edge MitraClip Technique. Circulation 2017;135:1802-14.

Non-Final Office Action received for U.S. Appl. No. 15/943,792 dated Jan. 8, 2020, 50 pages.

Non-Final Office Action received for U.S. Appl. No. 15/943,971 dated Jan. 8, 2020, 49 pages.

Parada-Campelo F, Perlman G, Philippon F, et al. First-in-Man Experience of a Novel Transcatheter Repair System for Treating Severe Tricuspid Regurgitation Journal of the American College of Cardiology 2015;66:2475-83.

Regueiro, et al. Transcatheter Mitral Valve Replacement: Insights From Early Clinical Experience and Future Challenges; JACC vol. 69, No. 17, 2017; May 2, 2017: 2175-92.

Rogers J. Transcatheter TR solution 6: Millipede. Transcatheter Cardiovascular Therapeutics; Nov. 1, 2017, 2017; Denver, Colorado.

Rosser BA, Taramasso M, Maisano F. Transcatheter interventions for tricuspid regurgitation: TriCinch (4Tech). EuroIntervention : journal of EuroPCR in collaboration with the Working Group on Interventional Cardiology of the European Society of Cardiology 2016;12:Y110-2.

Stephan von Bardeleben R, Tamm A, Emrich T, Munzel T, Schulz E. Percutaneous transvenous direct annuloplasty of a human tricuspid valve using the Valtech Cardioband. European heart journal 2017;38:690.

Toyama et al. Mitral annular motion in patients after transcatheter MitraClip and mitral valve surgery; Echocardiography 2017; 34: 334-339.

\* cited by examiner

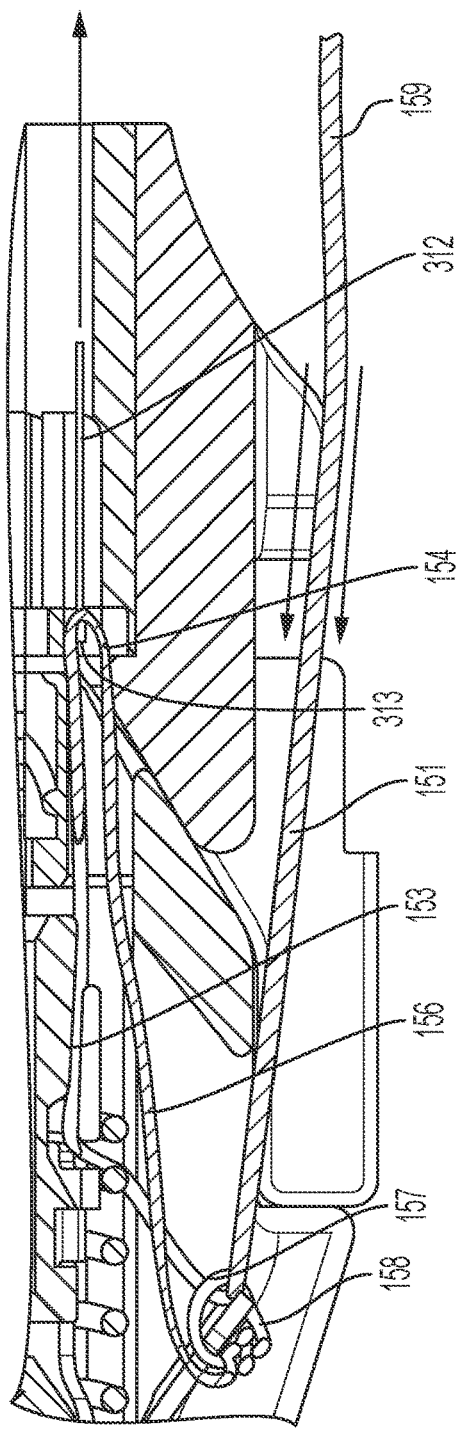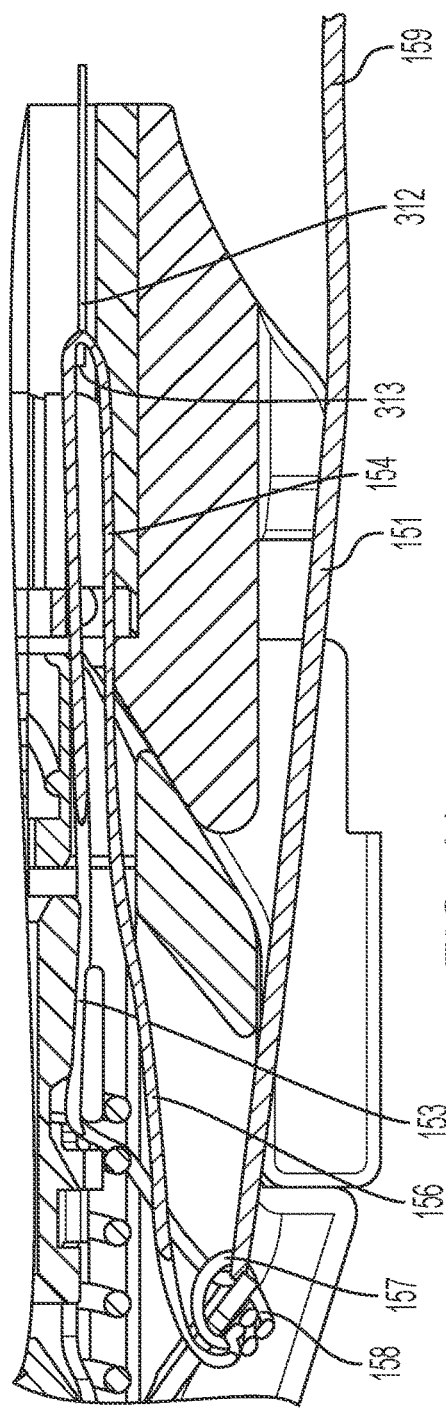

TRANSCATHETER ANCHOR SUPPORT AND METHODS OF IMPLANTATION

CROSS REFERENCE TO RELATED APPLICATIONS

This application claims priority to U.S. Provisional Ser. No. 63/086,582, filed Oct. 1, 2020, the disclosure of which is incorporated herein by reference.

FIELD OF THE INVENTION

The present invention relates generally to medical devices and systems for minimally invasively being implanted into the heart and methods of implantation of these devices and systems. More specifically, the invention shown and described in detail pertains to medical devices and systems which are implanted minimally invasively to provide a locking mechanism between two or more components of any cardiac implant, or between two or more cardiac implants. Although contemplated as a locking mechanism for cardiac implants, the present invention could be used to secure other implants within the body, such as intravascular, osteal, or other implants.

SUMMARY OF THE INVENTION

Presented herein are medical devices and systems which are implanted minimally invasively inside the heart, using one or more locking systems. The locking systems include a lock cap, lock cone, lock collar, and a tethering system, which includes a tether swivel and tethers. The distal end of the lock cap may cooperate with any anchor with or without an anchor support, and the proximal end of the locking system may connect to a tethering system. Alternatively, the distal end of the lock cap may cooperate with another tethering system, or with any type of rigid or non-rigid member connected to a cardiac wall and/or to a cardiac implant. Via the distal end of the lock cap, or via the proximal end of the lock cap connected to a tethering system, the locking system may connect to any type of intracardiac prosthesis including, but not limited to, a transcatheter valve replacement (complete or hemi-valve replacement), valve repair system (chordal implant, coaptation element, leaflet augmentation device, or annuloplasty ring), myocardial remodeling device, or ventricular assist device, microelectromechanical, pressure, or other type of sensors, drug-eluting implants, nerve fixation/stimulation devices, or stem cell implants.

According to one aspect, the locking system connects to an anchoring system, extension member, or to a cardiac implant on its distal end, and connects via the proximal end to a tethering system to any implant as described above. In one aspect, the locking system is delivered completely endovascularly, using a lock delivery system, which may or may not be integrated into another delivery system, such as a valve delivery system.

In another aspect, the system comprises a trans-septal guide catheter and a lock delivery system. The lock delivery system is comprised of a lock delivery system guide catheter (comprised of a distal end, shaft, and proximal control handle), lock delivery system cap, lock delivery system guidewire, lock delivery system spring, lock delivery system collar controllers, and lock delivery system tether controllers. The integrated tethering system comprises a tether swivel and tethers.

According to various aspects, the lock cap is comprised of a distal anchoring end, body, and a proximal head. The distal end has the cross-section of a circle, ellipse, or any polygon and optionally has a diameter different from the rest of the lock cap. For example, the terminal portion of distal end might have the cross-section of a circle that is larger than the cross-section of the body or proximal tethering end. Also, the distal anchoring end selectively includes a lumen that allows it to couple, reversibly or irreversibly, directly to an anchoring system, to an extension member connected to another intracardiac implant, or directly to another intracardiac implant. Other mechanisms of connecting the distal anchoring end of the lock cap (direct fusion, clasps, clamps, tethers) to an anchoring system, intracardiac implant via an extension member, or directly to the intracardiac implant, are within the scope of the instant invention. The body of the lock cap has the shape of any type of circular or elliptical column, or a portion of any polyhedron, and selectively includes a variable width along its length. As shown, the body of the lock cap takes a frustoconical shape with a larger diameter near the distal end. The proximal head likewise has the shape of any circular or elliptical column, or a portion of any polyhedron; as shown, it is defined by a frustoconical shape with its basal diameter bigger than the adjacent portion of the body. The proximal head has a lumen at its very end to allow connection to a guidewire. The guidewire attaches to the proximal head via complementary threads, but other methods of connection are contemplated. Any portion of the lock cap may be constructed of cobalt chromium, stainless steel, nitinol, or any metal alloy and may or may not have plastic polymeric elements, and any portion of the lock cap may or may not be covered with biological membranes, such as adult or juvenile bovine, ovine, equine, or porcine pericardium, or with synthetic membranes, such as, but not limited to classes consisting of polycarbonate, polyurethane, polyester, expanded polytetrafluoroethylene (ePTFE), polyethylene terephthalate (PET), polyetheretherketone (PEEK), silicone, natural or synthetic rubbers, or a combination thereof.

In another aspect, the lock cone includes a distal end with an assembly groove to allow coupling to a portion of a tethering system, specifically a tether swivel or the like, and a proximal end with a surface for coupling to the lock collar. The distal end has the shape of any elliptical or circular column, or polygon, and the assembly groove is a circumferential section with a smaller diameter than the rest of the distal end to allow any portion of the tethering system, such as a tether swivel, to couple to the distal end. The proximal end has any shape, similar or different to the distal end, but is shown as a tapered surface such that the diameter of the proximal end decreases as the proximal end approaches the assembly groove (inverted frustoconical shape). Alternatively, the proximal end is a tapered surface such that the diameter increases as the proximal end approaches the assembly groove (frustoconical shape). The lock cone has a lumen running from the proximal to distal end to allow a guidewire to run through the lock cone. Like the lock cap, the lock cone is constructed of any combination of metallic alloys or plastic polymers and is optionally covered with either biological or synthetic membranes.

The lock collar is comprised of a coupling collar and one or more control rod connectors. Alternatively, the lock collar is comprised of a coupling collar alone without control rod connectors. The lock collar has a perimeter that is circular, elliptical or that of any polygon, but as shown, is circular and includes a varying diameter along its length (i.e., may be a frustoconical or inverted frustoconical shape). The lock collar has a lumen that is shaped to couple with the proximal end of the lock cone. If the collar has control rod connectors, the one or more control rod connectors are connected to the outside of the lock collar and are positioned at an equal or variable distance from each other around the perimeter of the lock collar. The one or more control rod connectors are columns and/or have any cross-sectional shape. One or more of the control rod connectors have a lumen into which the control rods insert and are coupled via complementary threads or via other mechanisms. Alternatively, the one or more control rod connectors are protrusions in the shape of any portion of a circle, ellipse, or polygon, and have one or more grooves or lumens to attach to the control rods. The lock collar is constructed of any of the aforementioned the materials and/or covered by any membranes as described above for the lock cap and lock cone.

In another aspect, the tethering system consists of a tether swivel, composed of any metal or metallic alloy, and tethers, composed of, but without limitation, expanded polyethylene tetrafluoroethylene (ePTFE), ultra-high-molecular-weight polyethylene (UHMPWE or UHMW), nitinol wire, or any known surgical suture. The tether swivel further consists of a distal tether base, one or more locking arms, shaft, one or more coupling tabs, and a proximal tether collar. The tether swivel includes one or more tether arms, but alternatively is constructed without tether arms. The locking arms and tether arms (if tether arms are present) have a variable length and thickness and are spaced equally or at variable distances along the circumference of the tether ring. The tether arms have distal coupling members, in the shape of eyelets, but without limitation in shape, that attach to tethers. If the tether swivel does not have tether arms, the tethers attach to holes in the shaft of the tether swivel. The locking arms couple the tether swivel to the lock cap shaft. The proximal tether collar has one or more coupling tabs that connect the proximal tether collar of the tether swivel to the assembly groove of the lock cone. The tethering system may be composed of any of the materials or membranes as detailed above.

In another aspect, the tethering system includes tether routing, which is able to transmit, redirect, amplify, or deamplify force similar to a pulley system. The lock is modular, permanently implantable, or temporarily implantable, allowing for routing of tethers to allow for binary (locked/unlocked) states or continuously variable performance for the purpose of positioning, adjusting, implanting, fixating, locating, and/or delivering an implant. This includes the ability to utilize tethers and/or geometric surfaces to achieve temporary, permanent, or continuously adjustable possibilities of built-in, local or global, force amplification/limits/de-amplification.

In another aspect the lock delivery system has a lock delivery system guide catheter which is connected distally to the lock delivery system cap, which houses the lock cone, tether swivel and tethers, lock collar, and lock delivery system spring. The shaft of the lock delivery system guide catheter houses the lock delivery system tether controllers, and these controllers extend through the shaft and connect to the proximal control handle. If the lock collar has control rod connectors, the associated lock system collar controllers also extend through the shaft and connect to the proximal control handle.

In one aspect, the lock delivery system delivers the lock cone, lock collar, and tethering system as a unit over a guidewire connected to the lock cap, which has been previously delivered as an integrated part of an anchoring system or separately from an anchoring system. The tether swivel, housed within the distal lock delivery system cap, advances over the guidewire, going over the proximal end of the lock cap, until the locking arms of the tether swivel snap into place over the shaft of the lock cap, fixing the tether swivel to the lock cap. In this baseline state, the lock delivery system spring, while encircling the tether swivel shaft, urges the lock collar upwards, trapping the one or more tethers in between the lock collar and the lock cone (the locked state).

In another aspect, to achieve the unlocked state, either lock delivery system collar controllers or an unlocking tube, are advanced, pushing the lock collar downwards relative to the lock cone, compressing the lock delivery spring, thereby allowing the proximal portion of the tethers to translate freely. In this state, one or more lock delivery system tether controllers are pulled, thereby shortening the length of one or more tethers. By releasing forward pressure of either the system collar controllers or the unlocking tube, the spring is free to expand, pushing the lock collar back up relative to the lock cone, thereby trapping the one or more tethers in the locked position. If forward pressure is exerted on the system collar controllers again, and the delivery system tether controllers are released, the one or more tethers are allowed to lengthen again. In another aspect, the unlocked state is the default of the lock assembly. The collar and cone may be temporarily fixed into the unlocked state to allow for free adjustment and actuation until a desired criterion is met. At this point the collar and cone may be unfixed by any number of mechanisms, including but not limited to the pulling of a retaining pin, to thereby trap the tethers and have the lock enter a permanent or temporary locked state. In another implementation of this aspect, blade-like features on any part of the assembly may exist such that the act of releasing the cone and collar would selectively sever any number of tether lines to achieve desired position or force equilibrium when locked as well as allow certain features to be retrievable and making others permanently implanted. In another aspect, once final locking position is achieved, the lock delivery system tether controllers are disengaged from the tethers, and if lock delivery system collar controllers are used to control lock collar position, they are capable of being disengaged from the lock collar control rod connectors. If a locking tube is used to control collar position, the tube is not connected to the collar and does not have to be disengaged. At this point, the lock delivery system is removed from the locking system, leaving the tether swivel and tethers connected to the anchor cap, secured in position by the lock cone and lock collar. Finally, the delivery guidewire is disengaged from the proximal end of the lock cap.

In another aspect, the tethers are routed in such a manner that after the tether controllers are disengaged from the tethers, excess length of the tethers proximal to the lock is cut away. At this point, the lock delivery system may be removed, and delivery guidewire disengaged as described herein.

In another aspect, the tethers are routed in such a manner that the force on the tether is coupled to the force maintaining the lock state. One such implementation of this would include routing the tethers around parts of the collar such that the supporting forces push the frustoconical shapes of the collar and cone together. In this depiction, with more force applied to the tethers, the tighter the grip and locking ability of the frustoconical surfaces.

The lock delivery system cap is composed of any metallic alloy or plastic polymer and covered with any biological or synthetic membrane, and the same or different material properties are true for the lock delivery system spring, lock delivery system collar controllers, and lock delivery system tether controllers.

Related methods of operation are also provided. Other apparatuses, methods, systems, features, and advantages of the medical devices and systems that are implanted minimally invasively in the heart will be or become apparent to one with skill in the art upon examination of the following figures and detailed description. It is intended that all such additional apparatuses, methods, systems, features, and advantages be included within this description, be within the scope of the medical devices and systems that are implanted minimally invasively in the heart and be protected by the accompanying claims.

BRIEF DESCRIPTION OF THE FIGURES

FIG. 40 is a magnified cross-sectional side elevational view of the tether in its original position;

FIG. 41 is magnified cross-sectional side elevational view of the tether pulled upwards;

DETAILED DESCRIPTION OF THE INVENTION

Figure 1:
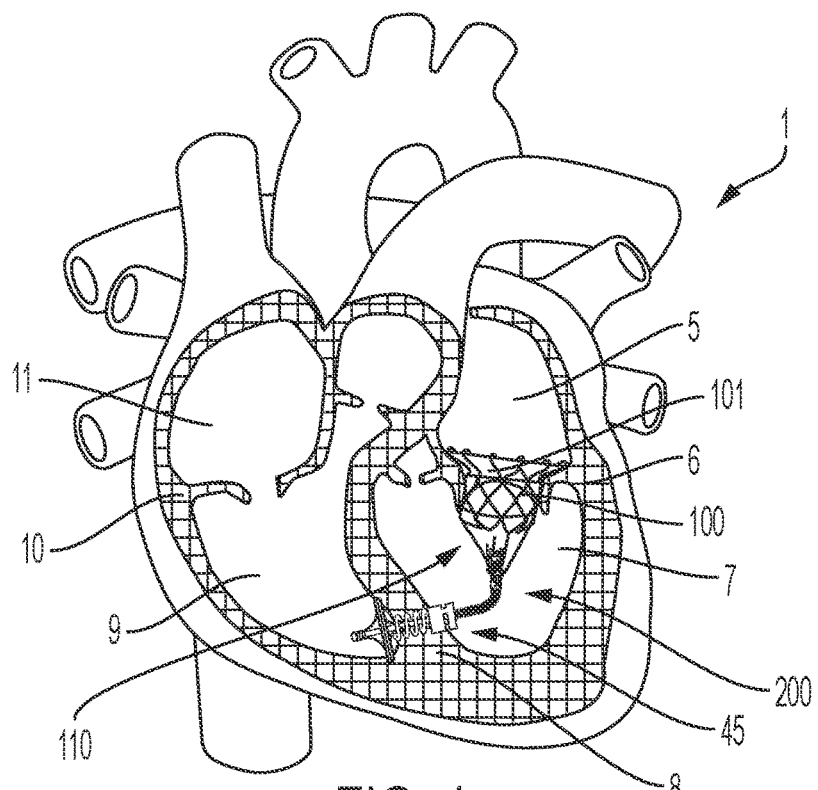
FIG. 1 is a cut-away perspective view of a heart showing a transcatheter heart valve positioned across the mitral valve in the heart and secured to an anchoring system by the locking system, according to the present invention.

The present invention is understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "tether" includes aspects having two or more tethers unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not. For the purposes of describing and defining the present invention it is noted that the use of relative terms, such as "substantially", "generally", "approximately", and the like, are utilized herein to represent an inherent degree of uncertainty that is attributed to any quantitative comparison, value, measurement, or other representation. These terms are also utilized herein to represent the degree by which a quantitative representation may vary from a stated reference without resulting in a change in the basic function of the subject matter at issue. As used herein, "distal" refers generally to the operative end of a member or facing the direction of implantation and "proximal" refers generally to the end of a member facing the direction of introduction or facing the user performing the implantation.

The application relates to medical devices and systems to be minimally invasively implanted in the heart and methods of implantation of these devices and systems. More specifically, the application relates to locking systems 200, and methods and systems for endovascularly introducing and implanting locking systems 200 so that an intracardiac implant, such as a valve 100 in the heart, may be secured to an anchoring system, or to another intracardiac implant with or without an extension member in between. This application also relates to use of this system for the implantation of other intracardiac implants, such as valve repair devices (e.g., chordal repair systems, valve coaptation devices, leaflet augmentation systems, or annuloplasty rings), ventricular remodeling devices, or other cardiac implants such as transcatheter ventricular assist devices, microelectromechanical, pressure, or other type of sensors, drug-eluting implants, nerve fixation/stimulation devices, or stem cell implants.

Figure 2:
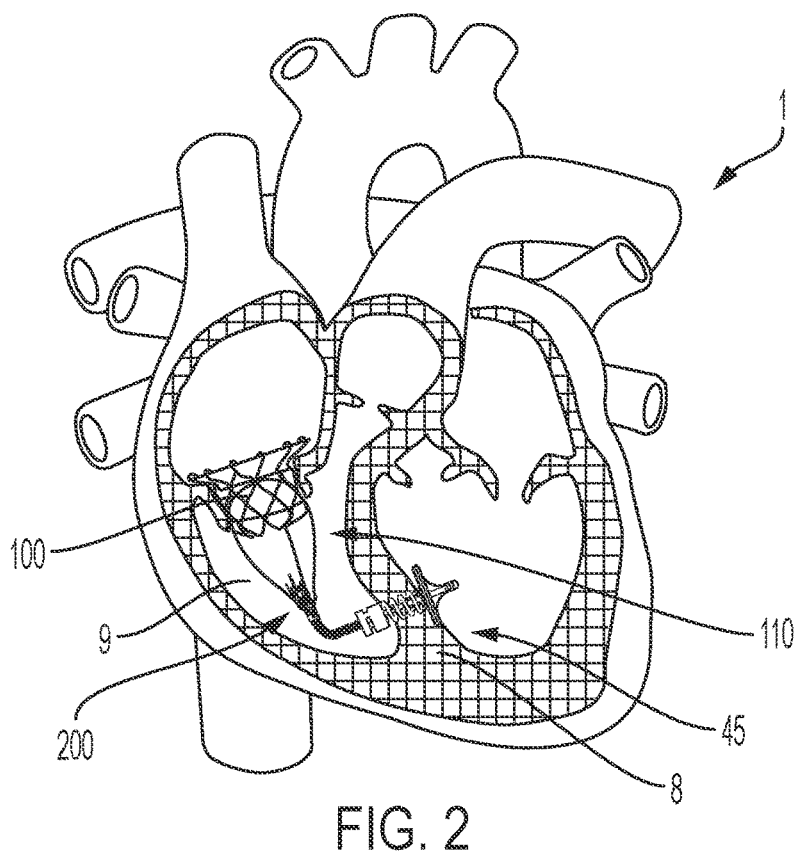
FIG. 2 is a cut-away perspective view of a heart showing a transcatheter heart valve positioned across the tricuspid valve in the heart and secured to an anchoring system by the locking system, according to the present invention.
Figure 3:
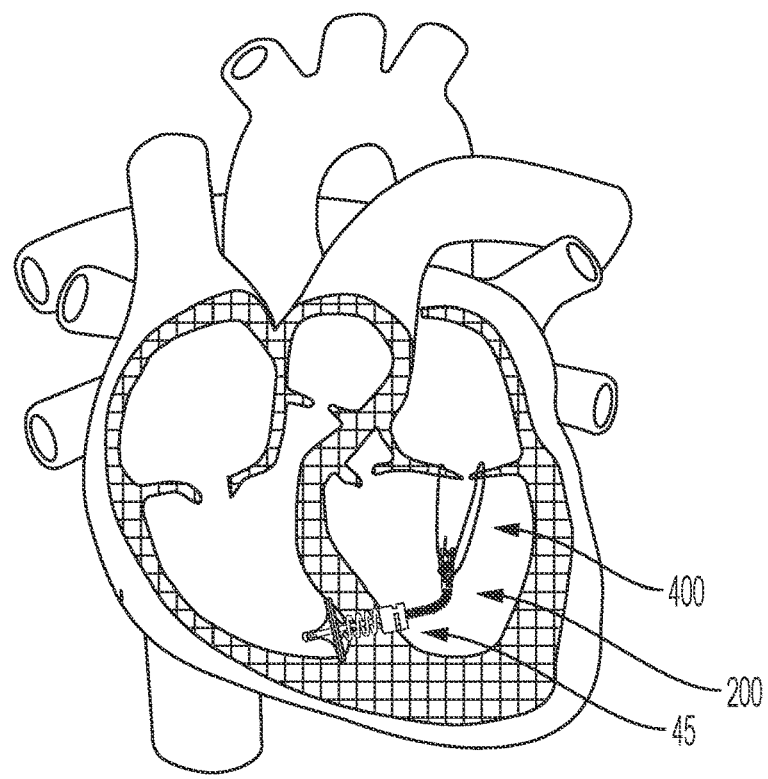
FIG. 3 is a cut-away perspective view of a heart showing a transcatheter chordal repair system for a mitral valve in the heart and secured to an anchoring system by the locking system, according to the present invention.
Figure 4:
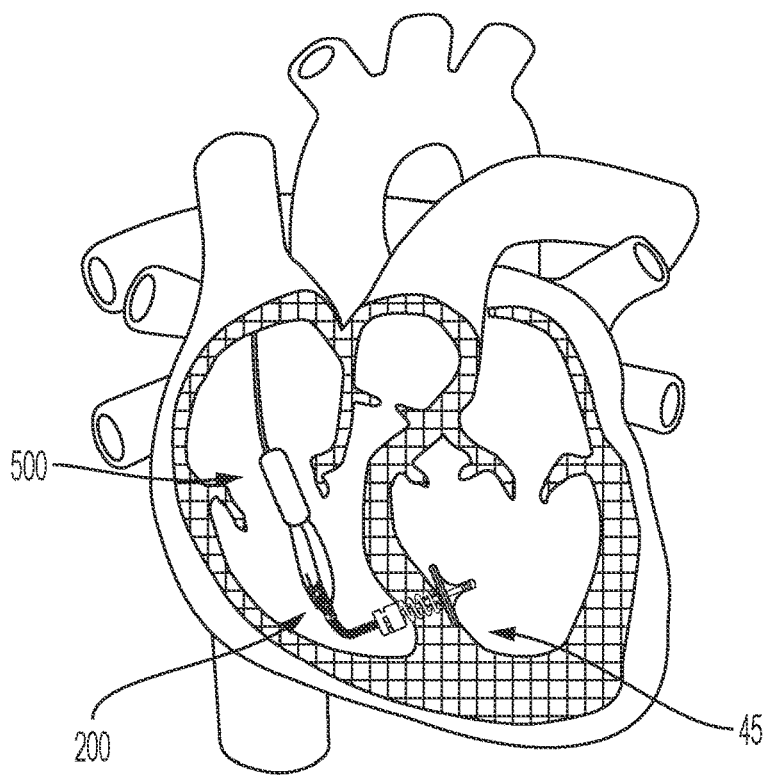
FIG. 4 is a cut-away perspective view of a heart showing a transcatheter coaptation element for a tricuspid valve in the heart and secured to an anchoring system by the locking system, according to the present invention.
Figure 5:
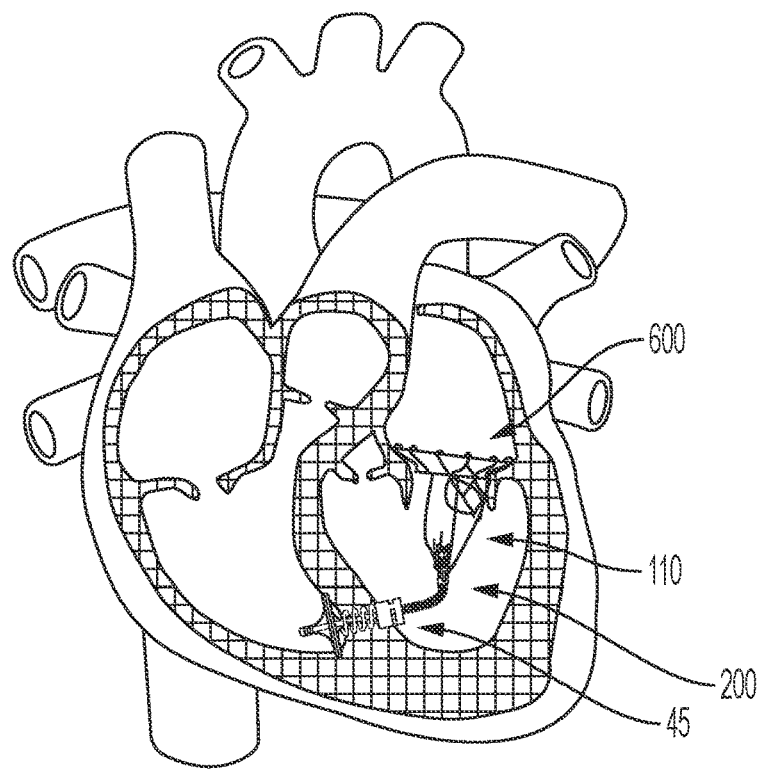
FIG. 5 is a cut-away perspective view of a heart showing a transcatheter hemi-valve replacement or leaflet augmentation element for a mitral valve in the heart and secured to an anchoring system by the locking system, according to the present invention.
Figure 6:
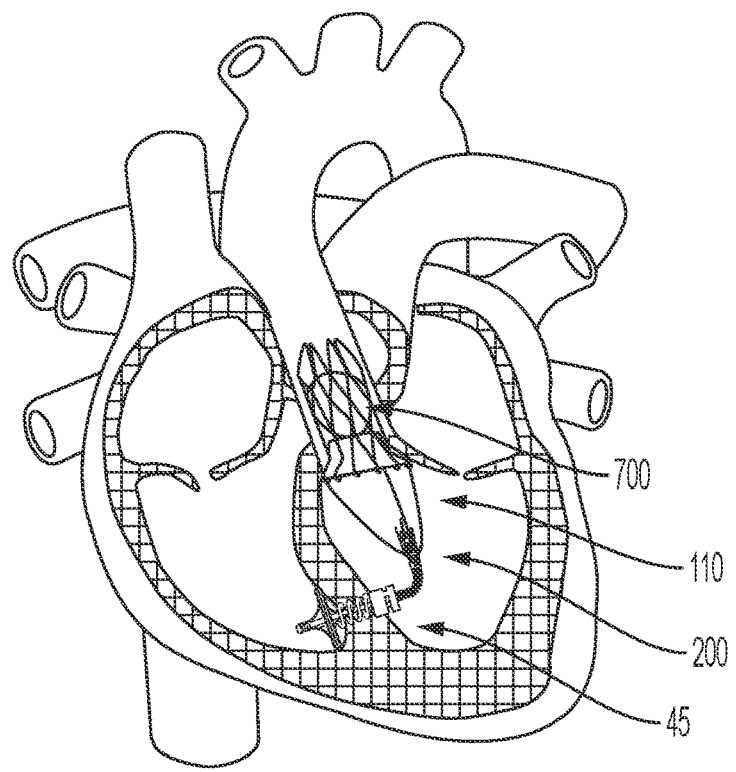
FIG. 6 is a cut-away perspective view of a heart showing a transcatheter left ventricular assist device in the heart secured to an anchoring system by the locking system, according to the present invention.
Figure 7:
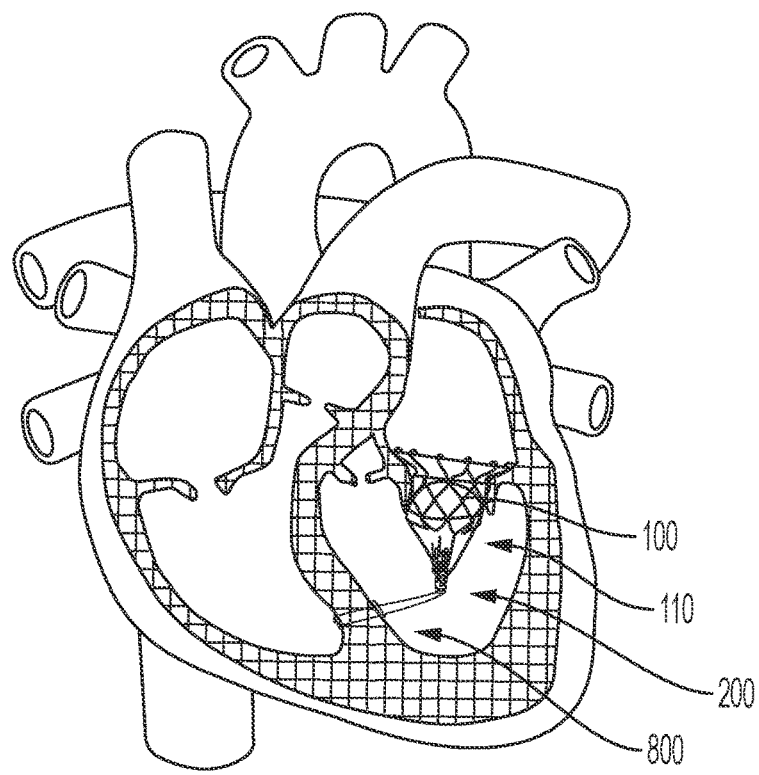
FIG. 7 is a cut-away perspective view of a heart showing a transcatheter heart valve positioned across the mitral valve and secured to a suture-based anchoring system by the locking system, according to the present invention.
Figure 8:
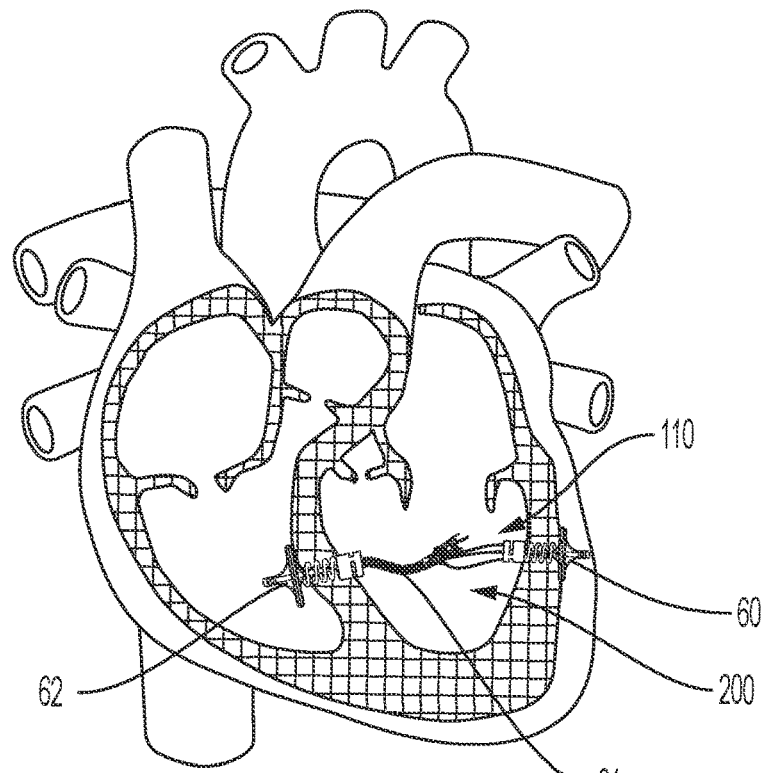
FIG. 8 is a cut-away perspective view of a heart showing a transcatheter left ventricular remodeling device with both cardiac wall implants secured together by the locking system, according to the present invention.

The disclosure herein relates to devices and systems having locking systems 200 and a lock delivery system 300 for implanting minimally invasively in the heart 1 and methods of implantation. FIG. 1 illustrates the transcatheter valve 100 which has been implanted to the replace the native mitral valve (for example) according the medical assembly disclosed herein. FIG. 2 illustrates the valve 100 implanted to replace the native tricuspid valve. FIG. 3 illustrates the transcatheter chordal system 400 implanted to provide chordal support to the native mitral valve. FIG. 4 illustrates the coaptation element 500 implanted to facilitate coaptation of the native tricuspid leaflets. FIG. 5 illustrates the hemi-valve or leaflet augmentation device 600 implanted to improve function of the native mitral valve. FIG. 6 illustrates the transcatheter left ventricular assist device 700 implanted to improve function of the left ventricle. The heart, of course, includes the left atrium 5, mitral valve 6, left ventricle 7, interventricular septum 8, right ventricle 9, tricuspid valve 10, and right atrium 11. The replacement valve 100 is positioned either to replace the mitral valve 6 or the tricuspid valve 10, or other intracardiac implants positioned as shown in FIGS. 3-7. As shown and described in FIGS. 1 and 2, by way of example, the locking system 200, is used to lock a transcatheter valve 100 to a tethering system 110 and to an anchoring system 45. The locking system 200 may connect distally to any type of anchoring system other then system 45, directly to another intracardiac implant or to another intracardiac implant via a connecting member. For example, FIG. 7 illustrates the locking system 200 connecting a transcatheter valve 100 to a tethering system 110 and to a suture-based anchoring system 800. As another example, in FIG. 8 the locking system 200 connects on one end via tethering system 110 to a cardiac implant 60 and on the other end via a flexible extension member 61 to a cardiac implant 62, so that the cardiac implants, extension member, locking system, and tethering system function as a left ventricular remodeling device.

The Lock Cap

Figure 9:
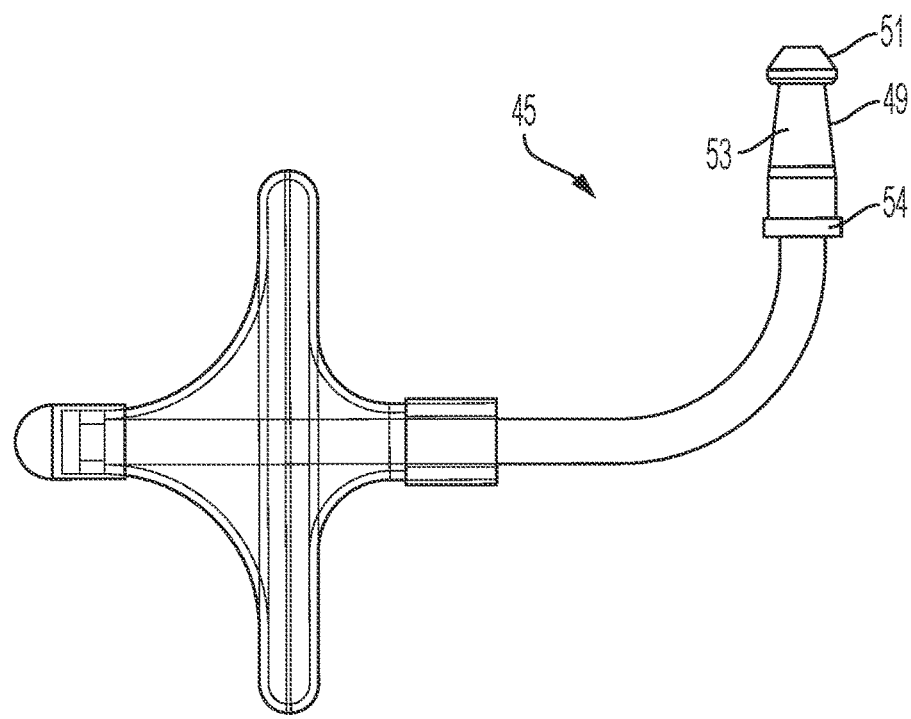
FIG. 9 is a side elevational view of an anchoring system with lock cap fused to the proximal end.
Figure 10:
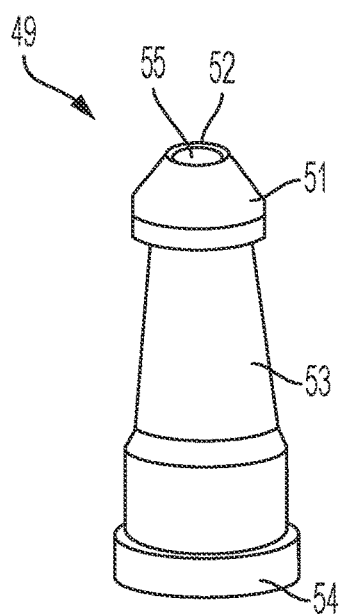
FIG. 10 is a perspective view of a lock cap.
Figure 11:
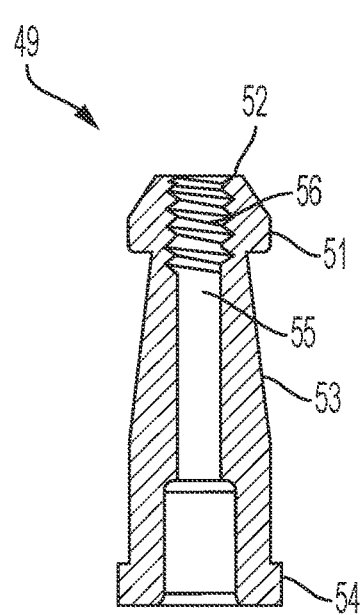
FIG. 11 is a cut-away perspective view of a lock cap.
Figure 13:
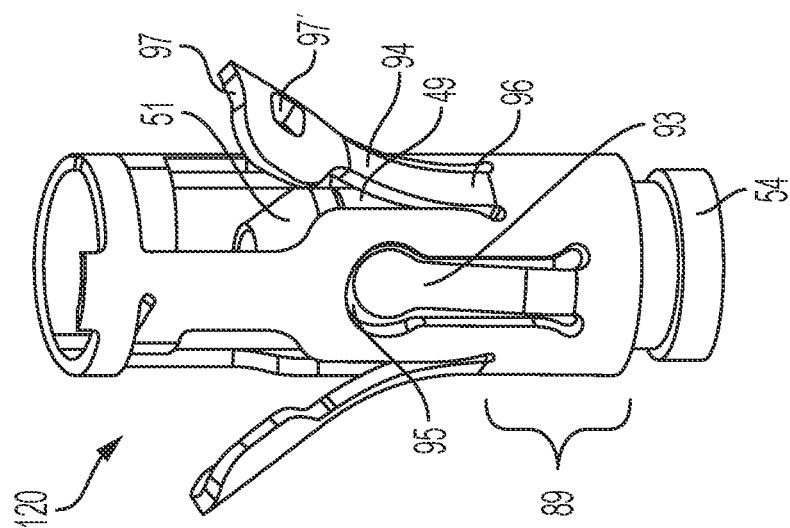
FIG. 13 is a perspective view of a tether swivel coupled to a lock cap.

Referring now to FIG. 9-11, at least one lock cap 49 is shown as an integral part of an anchoring system 45, but lock cap 49 may also be independent of anchoring system 45. Referring to FIGS. 10-11, the lock cap 49 includes lock cap head 51 with proximal end 52, lock cap body 53, and lock cap end 54. The lock cap end 54 is shown with a circular cross-section, although a cross-sectional shape of any polygon and with any diameter relative to the lock cap body 53, such as the same diameter or a larger diameter as the lock cap body 53 is within the scope of the present invention. The lock cap body defines a central lumen 55 configured for receipt of a guidewire or other member for connecting the lock cap 49 to the anchor assembly 45 and, on its proximal end, for receipt of a guidewire or other connecting member for connecting to the device being anchored. The lock cap body 53 shown has a frustoconical shape, and it is within the scope of this invention to have the shape of any polyhedron, and with a variable diameter along its length, such as with a larger diameter near the distal end 54 with a smaller diameter near the lock cap head 51. The lock cap head 51 shown has a frustoconical shape although it may take the shape of any polyhedron. The base of the lock head 51 shown has a larger diameter (although any diameter is contemplated) than the adjacent end of the lock cap body 53, and the lock cap head 51 may have a variable diameter along its course. In one aspect, the lock head 51 of lock cap 49 is coupled to a guidewire via complementary threads 56 within lock cap head 51. In another aspect the lock cap 49 is coupled to the tether swivel 88 of the tethering system 110 as shown in FIG. 13. In one aspect, the lock cap 49 is composed of any known metal alloy, including, but not limited to, nitinol, titanium, or cobalt-chromium. In another aspect, the lock cap 49 is covered in synthetic membranes such as polytetrafluoroethylene (PTFE), expanded polytetrafluoroethylene (ePTFE) or polyethylene terephthalate (PET). In another aspect, the lock cap 49 is covered in biological tissue, such as bovine, ovine, porcine, or equine pericardium, or with any combination of anti-inflammatory drugs or other natural or synthetic compounds that might promote healing and limit inflammation.

The Tether Swivel

Figure 12:
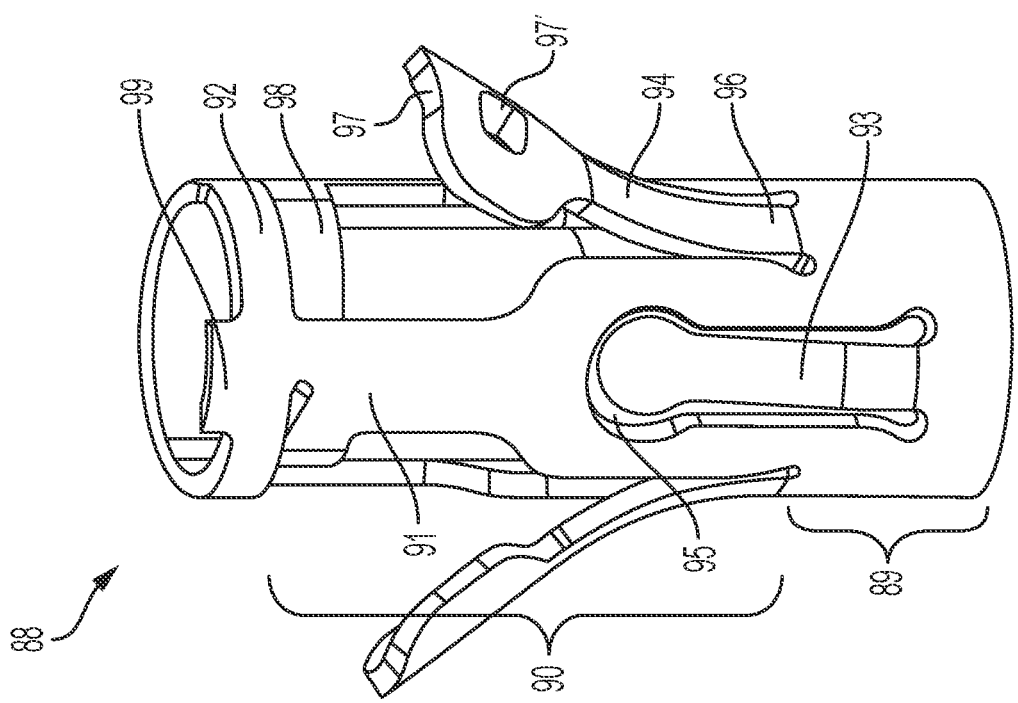
FIG. 12 is a perspective view of a tether swivel.
Figure 26:
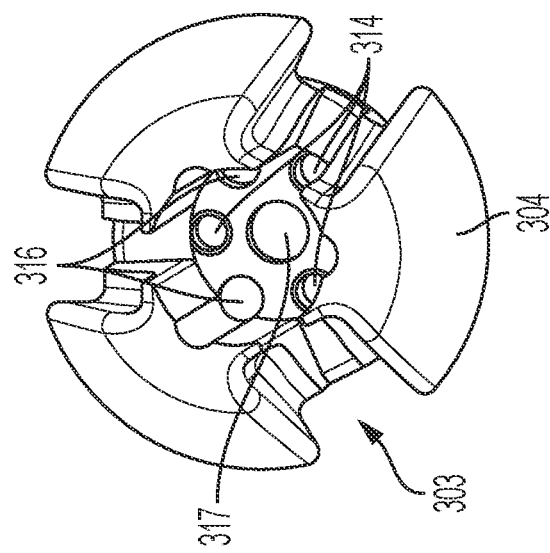
FIG. 26 is a perspective view looking at the end of the prothesis delivery cap.

Referring to the exemplary tether swivel 88 shown in FIG. 12, the tether swivel 88 having a tether swivel base 89 at its distal end, shaft collar 92 at its proximal end, and in between a shaft body 90 including shaft columns 91, locking arms 93, tether arms 94 with a base 96 and eyelet 97, and coupling arms 98. As FIGS. 12 and 13 show a front perspective view where two tether swivel arms 94, one locking arm 93 and one columnar support 91 are visible in the front perspective view. The tether swivel shaft 90 above the base 89 includes at least one, and as shown three, columnar members 91 or columns which define, on a distal portion thereof, a pair of tines defining a locking arm aperture 95. The opposite side of the tether swivel mirrors the side shown wherein there are three tether arms 94, three columnar supports 91 and three locking arms 94. As shown in FIG. 26 and described below, the three tether swivel arms cooperate with a respective one of the tether arm grooves 303. It is within the scope of the present invention to provide any number of tether arms 94, columnar supports 91 and locking arms 94 and the number of each need not be the same.

The tether swivel base 89 as shown is cylindrical, although other polygonal cross-sections are within the scope of the invention, and the base 89 has an internal diameter large than the lock cap body 53, but the internal diameter of base 89 is shown to be smaller than the outer diameter of the lock cap distal end 54. The shaft body 90 extends from the base 89 to shaft collar 92. The shaft body 90 may have the same or different thickness or shape compared to the base 89. The shaft column 91 resembles a tuning fork with a vertical portion extending distally from the shaft collar 92 and thicker bottom portion defining the locking arm aperture 95 adjacent the tether swivel base 89. Shaft collar 92 is shown as cylindrical, although other polygonal cross-sections are envisioned. Connected to the base 89 is at least one locking arm 93, which extends from the base 89 within the locking arm aperture 95 defined by the tether swivel body 90. Each locking arm 93 is flexible and is biased inwardly, in the direction of the longitudinal axis of the tether swivel 88, and each locking arm 93 bends or leans at the same or variable angle from each other. The arms 93 are shown similar but may also be of the same or variable width, length, and thickness. Similarly, the tether arm 94 is flexible and bends at the same or a different angle from any other tether arm 94 measured from the longitudinal axis of the tether swivel 88. The tether arm 94 has a distal base 96 that is connected to the tether swivel base 89, and a proximal end which defines an eyelet head 97, which has at least one aperture 97' to connect to at least one tether 150 described below. The coupling arm 98, shown as a rectangular tab, flexes radially inward, extends from the proximal end of the shaft column 91, may be shaped as a straight, an edge of any polygon, or as a curved member, and bends inwards towards the center of the swivel body 90. The upper or proximal end of the shaft column 91 connects to the shaft collar 92.

In another aspect, the tether swivel 88 is composed of any known metal alloy, including, but not limited to, nitinol, titanium, or cobalt-chromium. In another aspect, the tether swivel 88 may be covered in synthetic membranes such as polytetrafluoroethylene (PTFE), expanded polytetrafluoroethylene (ePTFE) or polyethylene terephthalate (PET). In another aspect, the tether swivel 88 may be covered in biological tissue, such as bovine, ovine, porcine, or equine pericardium, or with any combination of anti-inflammatory drugs or other natural or synthetic compounds that might promote healing and limit inflammation.

The Tether Swivel and Lock Cap Assembly

Figure 14:
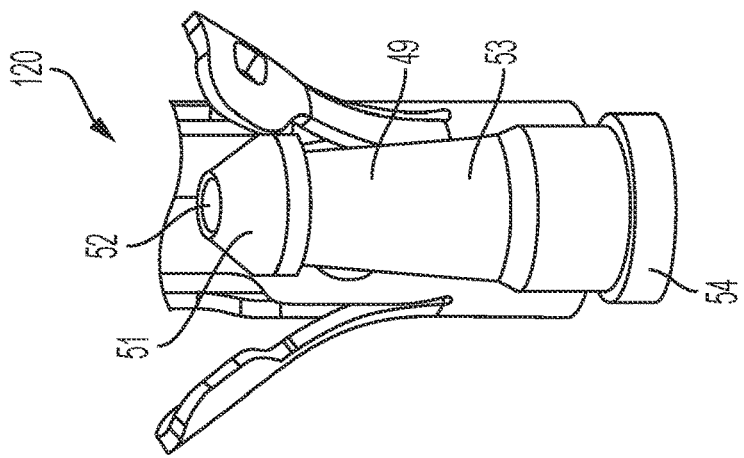
FIG. 14 is a partial cut-away of the tether swivel depicting the lock cap within and coupled to the tether swivel wherein the front columns of the tether swivel body is cut away.

Now referring to FIGS. 13-14, the tether swivel 88 is configured to receive the lock cap 49 to form a tether swivel/lock cap assembly as shown. In this aspect, the lock cap body 53 is configured to cooperate with and/or to attach to the tether swivel base 89 and the locking arms 93. FIG. 14 show the front fact of the tether swivel 88 removed to illustrate the lock cap 49 positioned within the tether swivel 88. Specifically, the lock cap distal end 54 has a diameter larger than the tether swivel base 89 of the tether swivel 88, preventing the tether swivel 88 from receiving the lock cap end 54. The lock cap body 53 as shown has a frustoconical shape (although other polygonal shapes are contemplated) such that the locking arms 93 of the tether swivel 88 bend or are urged inwardly to abut the surface of the lock cap body 53, wherein the proximal ends of the locking arms 93 cooperate with and rest below the lock cap head 51 to limit relative longitudinal movement. The larger diameter of the lock cap head 51 compared to the proximal end of the lock cap body 53 prevents the locking arms 93 (bent inwards and abutting the lock cap body 53), and thus the tether swivel 88, from moving past the lock cap head 51.

The Lock Cone and Lock Collar

Figure 16:
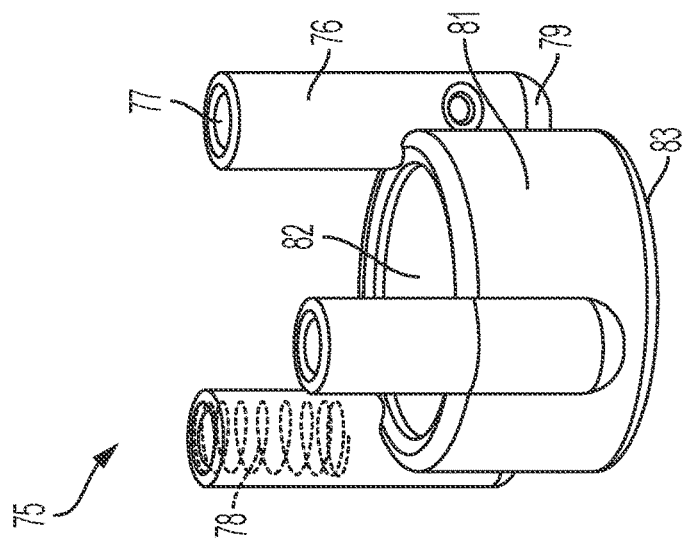
FIG. 16 is a perspective view of a lock collar.
Figure 15:
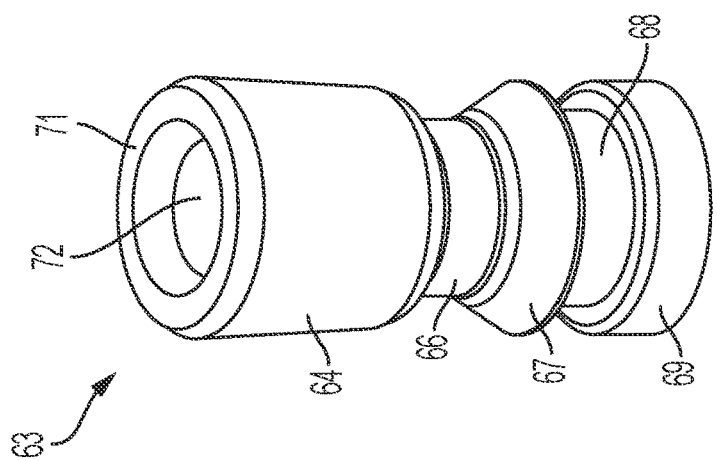
FIG. 15 is a perspective view of a lock cone.
Figure 17:
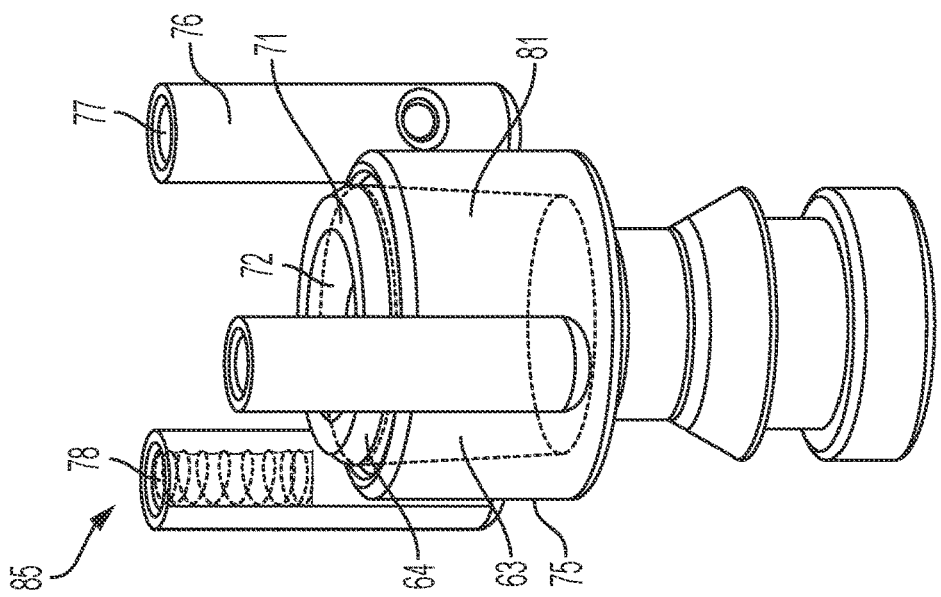
FIG. 17 is a perspective view of a lock collar coupled to a lock cone.

Referring to FIGS. 15-17, the locking systems 200 also includes a lock cone 63 and lock collar 75. The lock cone 63 includes a proximal end 71, lock cone tapered surface 64, lock cone mid-section 66, lock cone assembly hood 67, lock cone assembly groove 68, lock cone distal end 69, and lock cone lumen 72. The lock collar 75 includes a lock collar body 81, at least one (or as shown three) lock collar connector 76, lock collar body distal end 83 and lock collar lumen 82. Each lock collar connector 76 has a distal end 79, a central lumen 77 configured for receipt of a control rod 309 which defines internal threads 78 for mating with the control rod 309 as explained below.

In one aspect, the tapered surface 64 of the lock cone 72 has a reverse frustoconical shape, although any polygonal shape is contemplated, and has a diameter smaller than lock collar body lumen 82, which has a complementary shape to tapered surface 64. Referring to FIG. 17, the lock collar 75 is pre-assembled with lock cone 63, such that the lock collar body 81 and lock collar lumen 82 circumscribe the tapered surface 64 of the lock cone 63. In this configuration, the tether 150 runs between the tapered surface 64 of the lock cone 63 and the lock collar lumen 82. Attached to the lock collar 75 is at least one (and as shown, three, one for each lock collar connector 76 as shown in FIG. 21) lock collar control rods 309, which connects to the lock collar 75 via complementary threads 78 within the at least one control rod connectors 76, which are connected to the lock collar via the control rod connector proximal end 79.

In another aspect, the lock cone 63 or lock collar 75 is composed of any known metal alloy, including, but not limited to, nitinol, titanium, or cobalt-chromium. In another aspect, the lock cone 63 or lock collar 75 may be covered in synthetic membranes such as polytetrafluoroethylene (PTFE), expanded polytetrafluoroethylene (ePTFE) or polyethylene terephthalate (PET). In another aspect, the lock cone 63 or lock collar 75 may be covered in biological tissue, such as bovine, ovine, porcine, or equine pericardium, or with any combination of anti-inflammatory drugs or other natural or synthetic compounds that might promote healing and limit inflammation.

The Complete Locking System

Figure 19:
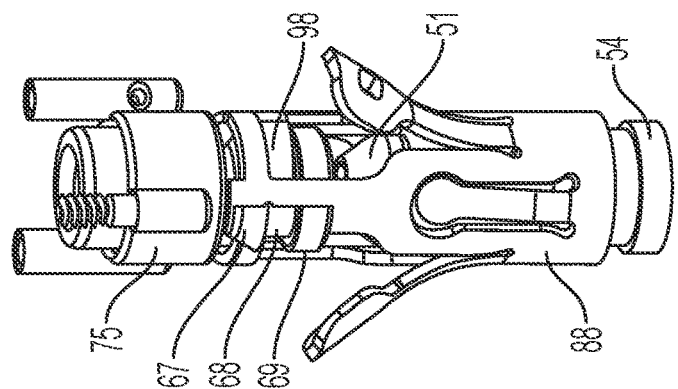
FIG. 19 is a partial cut-away view of the tether swivel connected to the lock cap assembly and having the lock cone and lock collar integrated therein wherein a portion of the tether swivel column is removed.
Figure 18:
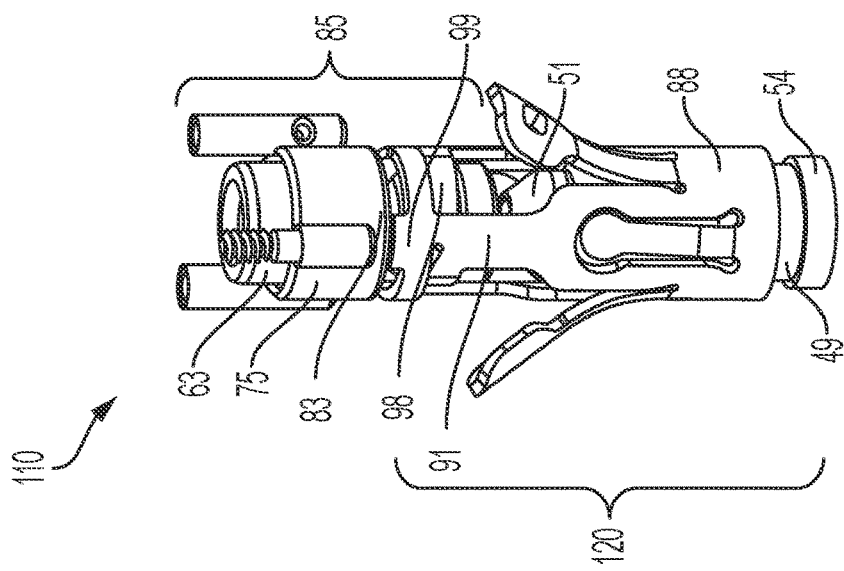
FIG. 18 is a perspective view of the tether swivel/lock cap assembly coupled with the lock cone and lock collar.
Figure 21:
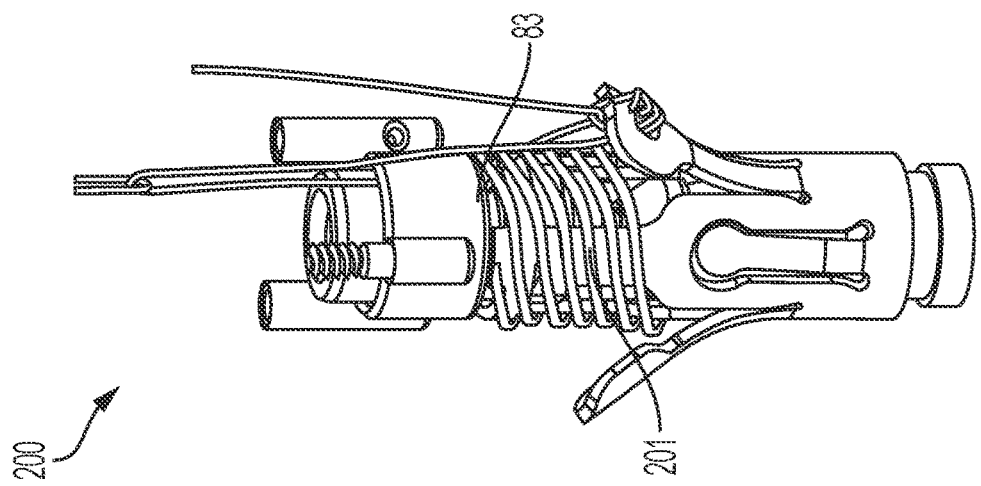
FIG. 21 is a perspective view of the system of FIG. 21 with the locking spring in place.

FIGS. 18-21 show the various components of the locking system 200 assembled together with the complete locking system 200 shown in FIG. 21. FIGS. 18-21 illustrate how the tether swivel 88, lock cone 63, lock collar 75, lock cap 49 and the lock collar 75 cooperate. As shown in FIG. 19, lock cone distal end 69 is positioned within the tether swivel 88 above lock cap head 51, of the tether swivel/lock assembly 120, and the lock cone distal end 69 is adjacent to and may or may not touch lock cap head 51. Above the lock cone distal end 69, the lock cone assembly groove 68 cooperates and/or couples with the tether swivel 88 by the tether swivel coupling arm 98, which bends into the assembly groove 68, in between the lock cone assembly hood 67 and lock cone end 69. The proximal end 99 of the shaft column 91 of the tether swivel 88 rests within the lock collar body end 83.

Figure 20:
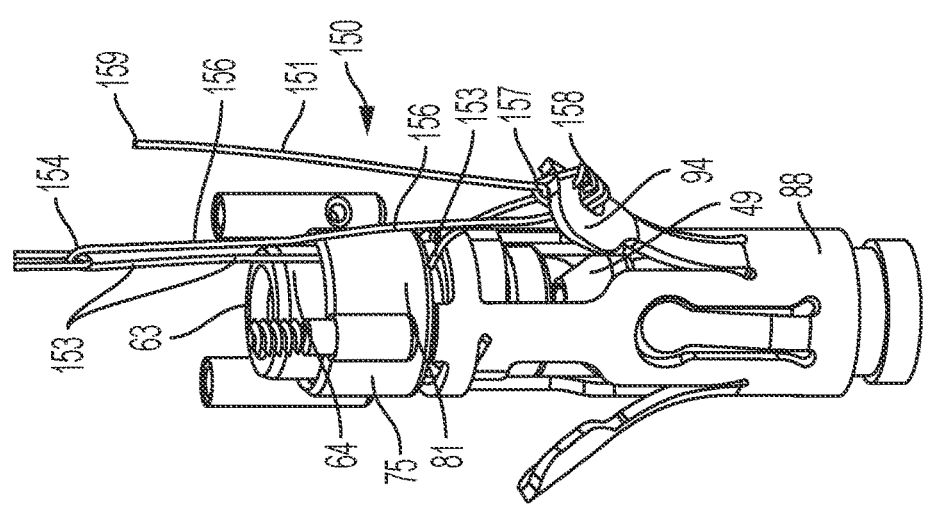
FIG. 20 is a perspective view of the system of FIG. 19 with a tether attached.

FIG. 20 illustrates the tether 150 coupled to the tether swivel 88, lock cone 63, and lock collar 75. Tether 150 as illustrated includes segments 151, 153, 154, 156, 157 and 158 for discussion purposes. The implant segment 151 of each tether 150 is attached proximally to the intracardiac implant as appropriate (not shown). Distally, the implant end 151 runs through the tether arm loop 157, which is next to the tether arm 94 of the tether swivel 88. Next, the implant segment 151, passes beneath and behind (facing its longitudinal axis) the lock collar body 81. Between the lock cone surface 64 and lock collar body 81, the interbody tether segment 153 of the tether 150 extends proximally until it loops around, forming the tether control loop 154. After the tether control loop 154, the lock tether segment 156 of the tether 150 extends through the eyelet 97' of the tether arm 94. The tether lock segment 156 extends around the top of the tether arm 94, forming the tether arm loop 157, which passes over the implant segment 151, and then tether lock segment 156 passes through eyelet 97 again, wrapping around itself to form a tether knot 158.

Referring now to FIG. 21 which depicts the entire locking system 200, which comprises the system of FIG. 20 and a locking spring 201. The locking spring 201 is positioned at or adjacent the tether arms 94, wrapping around the shaft columns 91 of the tether swivel 88, ending just below or adjacent to the lock collar body end 83 of the lock collar 75. The locking spring 201 may or may not encircle a portion of the implant segment 151 before it turns into the interbody tether segment 153.

The locking spring 201, as shown, is sized and configured as a helical spring. Optionally, each section of locking spring 201 may be differentially sized by radius, length, or pitch of coil. In one aspect, any section of the locking spring 201 is composed of any known metal alloy, including, but not limited to, nitinol, titanium, or cobalt-chromium. In another aspect, any section of the locking spring 201 may be covered in synthetic membranes such as polytetrafluoroethylene (PTFE), expanded polytetrafluoroethylene (ePTFE) or polyethylene terephthalate (PET). In another aspect, any section of the locking spring 201 may be covered in biological tissue, such as bovine, ovine, porcine, or equine pericardium, or with any combination of anti-inflammatory drugs or other natural or synthetic compounds that might promote healing and limit inflammation.

Figure 22:
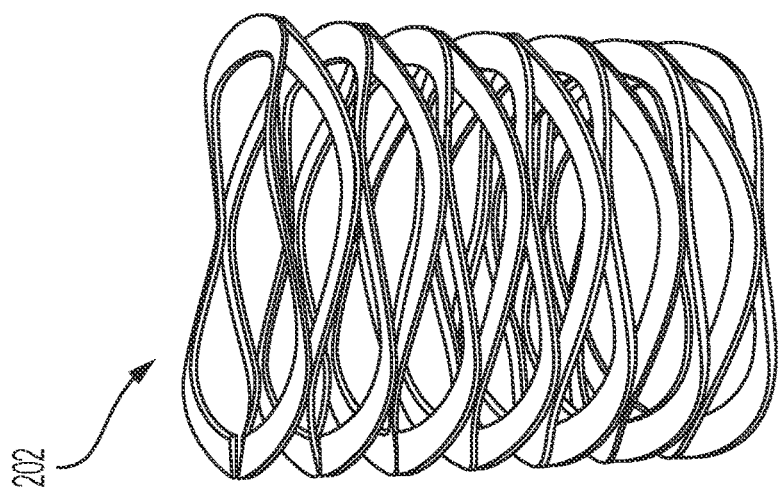
FIG. 22 is a perspective view of an alternative type of locking spring.

In another aspect, the locking spring could be in the form of a wave spring 202 as shown in FIG. 22. The displacement element could take other shapes, such as that of an elastomeric washer, or even be a cantilever beam. In principle, this element could be anything that may minimize the conical space between the lock cone and the lock collar using elastic displacement. Any section of this element may be covered in synthetic membranes such as polytetrafluoroethylene (PTFE), expanded polytetrafluoroethylene (ePTFE) or polyethylene terephthalate (PET). In another aspect, any section of the wave spring 202 may be covered in biological tissue, such as bovine, ovine, porcine, or equine pericardium, or with any combination of anti-inflammatory drugs or other natural or synthetic compounds that might promote healing and limit inflammation.

The Lock System with Simplified Tether Routing

Figure 23:
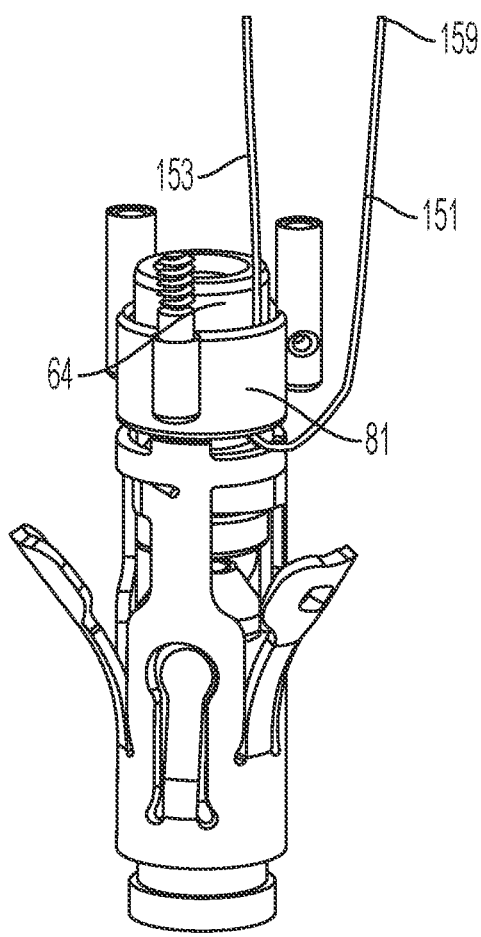
FIG. 23 is a perspective view of the system of FIG. 19 with a tether attached in alternative configuration.
Figure 24:
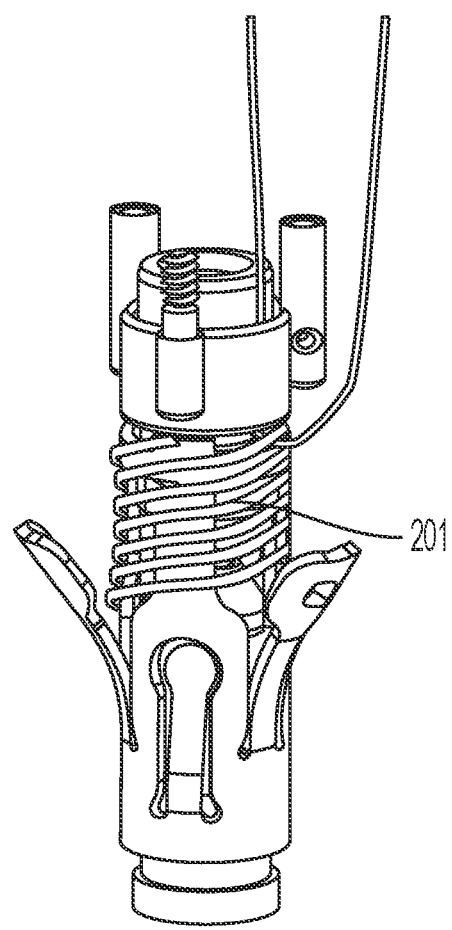
FIG. 24 is a perspective view of the system of FIG. 23 with the locking spring in place.

An alterative routing of the tether 150 is illustrated in FIGS. 23-24. The proximal end 159 of the implant segment 151 of tether 150 is attached to the intracardiac implant. The implant segment 151 passes underneath the lock collar body 81, forming the interbody segment 153 extending between the lock collar body 81 and the lock cone surface 64, and extends proximally through the lock delivery system.

The Lock Delivery System

Figure 25:
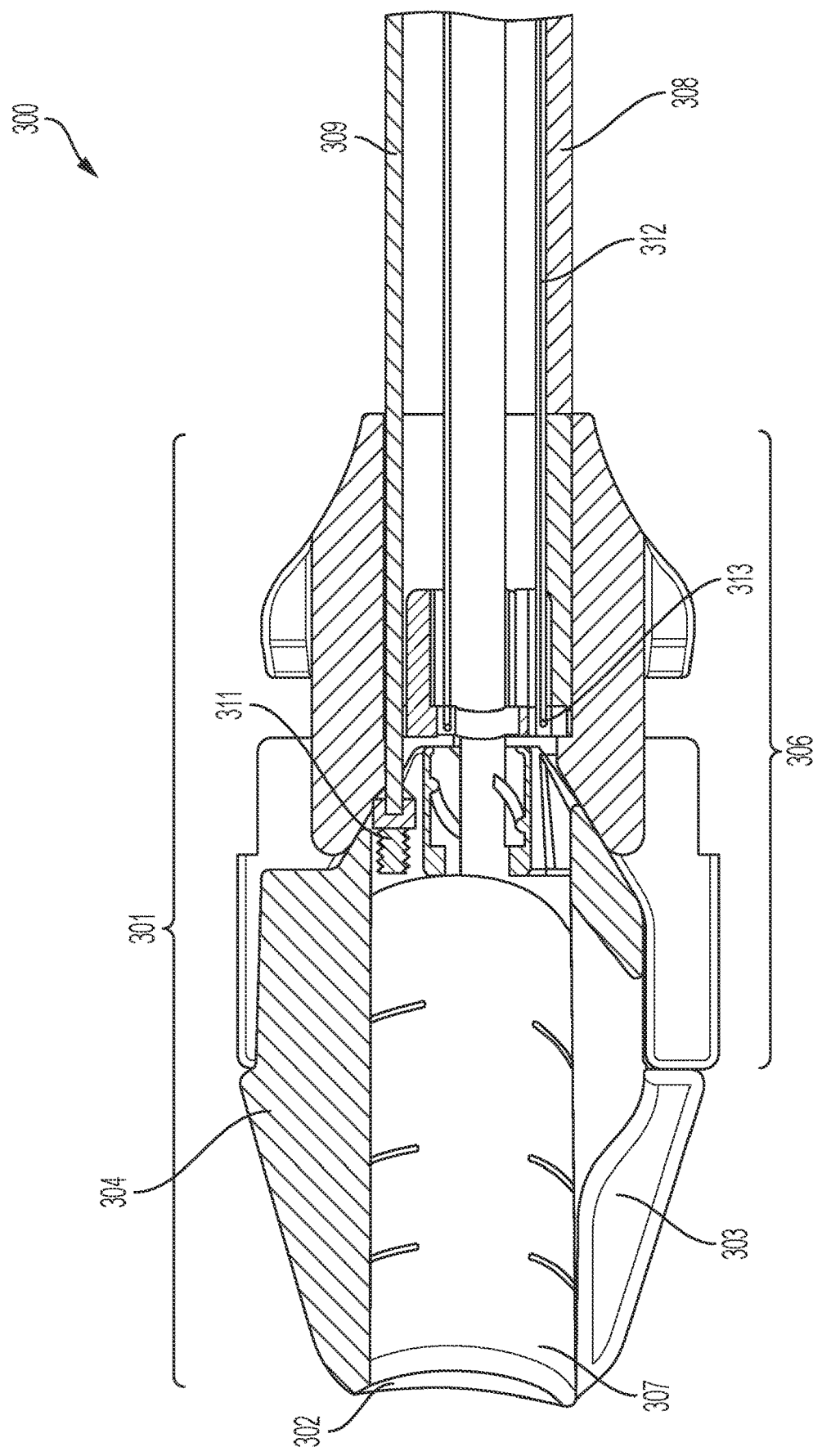
FIG. 25 is a cross-sectional side view of a locking delivery system without the locking components.
Figure 27:
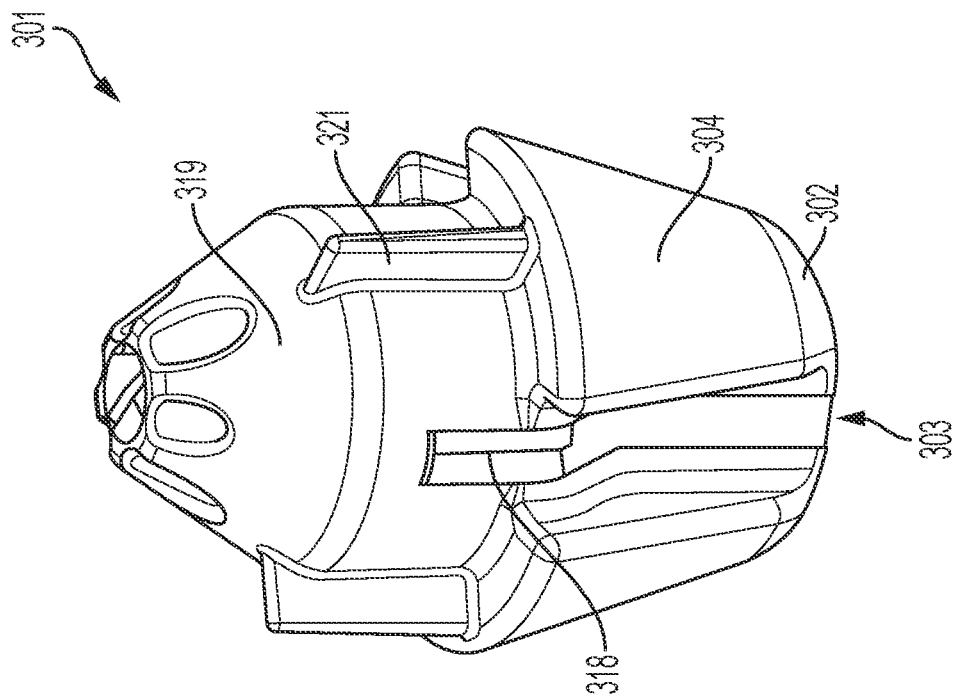
FIG. 27 is a perspective view of the entire prosthesis delivery cap without locking components.

FIGS. 25-27 show the lock delivery system 300 without any of the lock components (lock cap 49, lock cone 63, lock collar 75, or tether swivel 88) pre-loaded. FIG. 25 shows a longitudinal cross-section of the lock delivery system with a prosthesis delivery system cap 301 that has a distal end 302, proximal end 306, lumen 307 running through cap, at least one (as shown, three) tether arm groove 303, outer surface 304, lock delivery system shaft 308, at least one (as shown, three) lock collar control rod 309, and at least one (as shown, three) tether control lines 312. When the prosthesis delivery system cap 301 is associated with a valve system, it is termed a valve delivery system (VDS) cap. FIG. 26 shows an end-on view of the lock cap illustrating the at least one tether collar/tether connector hole 314, guidewire hole 317, and at least one supplemental hole 316. FIG. 27 is a perspective view of the prothesis delivery system cap and illustrates the at least one cap tether window 318.

The prothesis delivery system cap 301 as shown has a frustoconical shape distally, although other polyhedral shapes are not excluded. The proximal end 306 shown has a cylindrical base connected to proximal conical segment 319. Each of the holes within the distal end may be spaced evenly or at variable distance, and may have the same or different diameter, may take any polygonal shape. The e tether arm groove 303 may have the same or different polygonal shape with same or variable width, length, and degree of angulation to accommodate the associated tether arm of the tether swivel. Above the tether arm groove 303, the cap tether window 318 may have any polygonal shape, width, and length to accommodate a tether. Finally, the mating panel 321, extends from the mid-portion of the prosthesis delivery system cap 301, and extends proximally. Each panel 321 may be shaped as a rectangle or any shape, may be spaced equally or at variable distance along the circumference of the cap 301, and may have the same, or different thickness and length. Like other components of the locking system, the lock delivery system 300 may be composed of any type of metallic alloy and may be covered by any biological or synthetic membrane.

The Lock Delivery System and Lock Components

Figure 28:
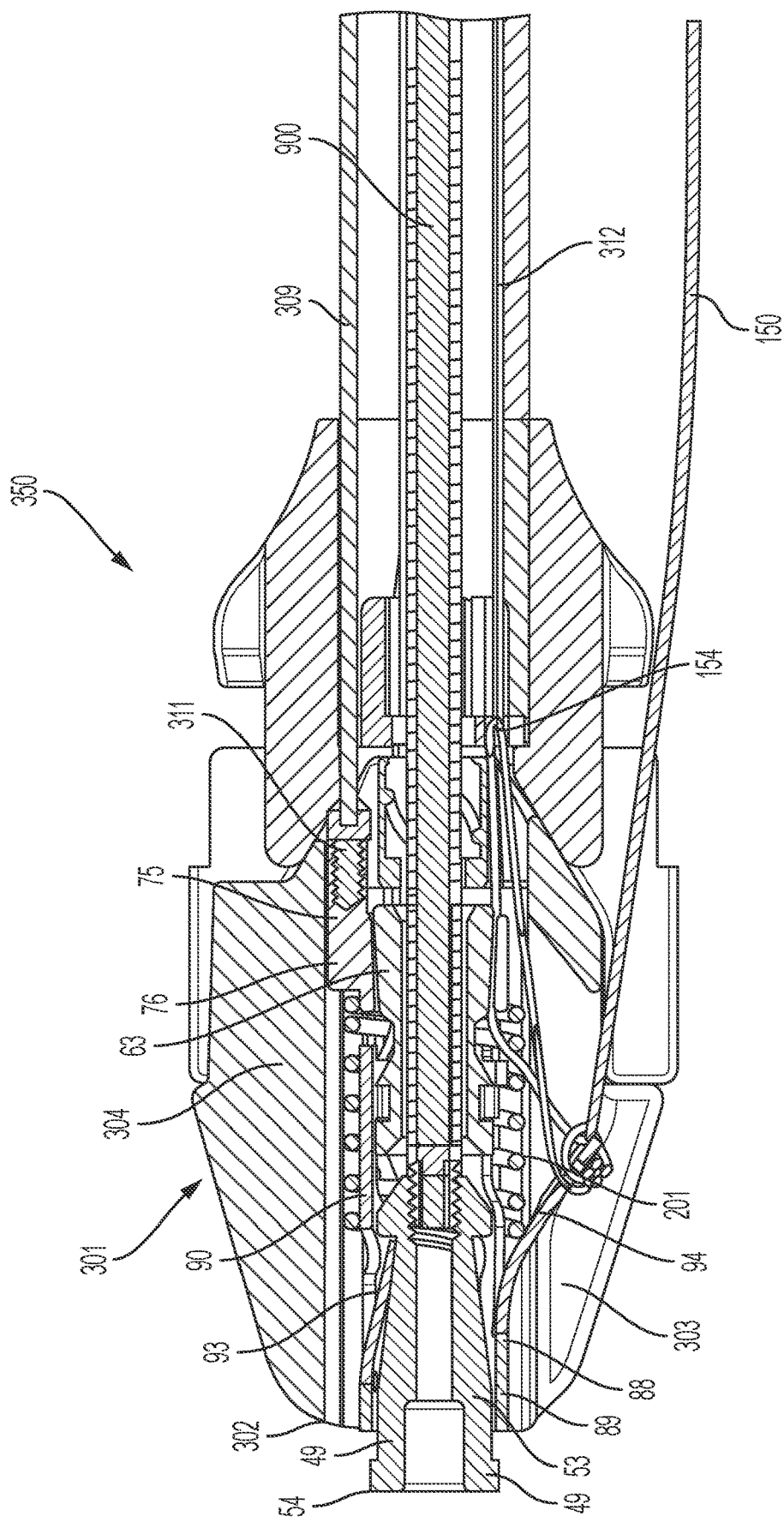
FIG. 28 is a cross sectional side view of a locking delivery system with locking components.
Figure 29:
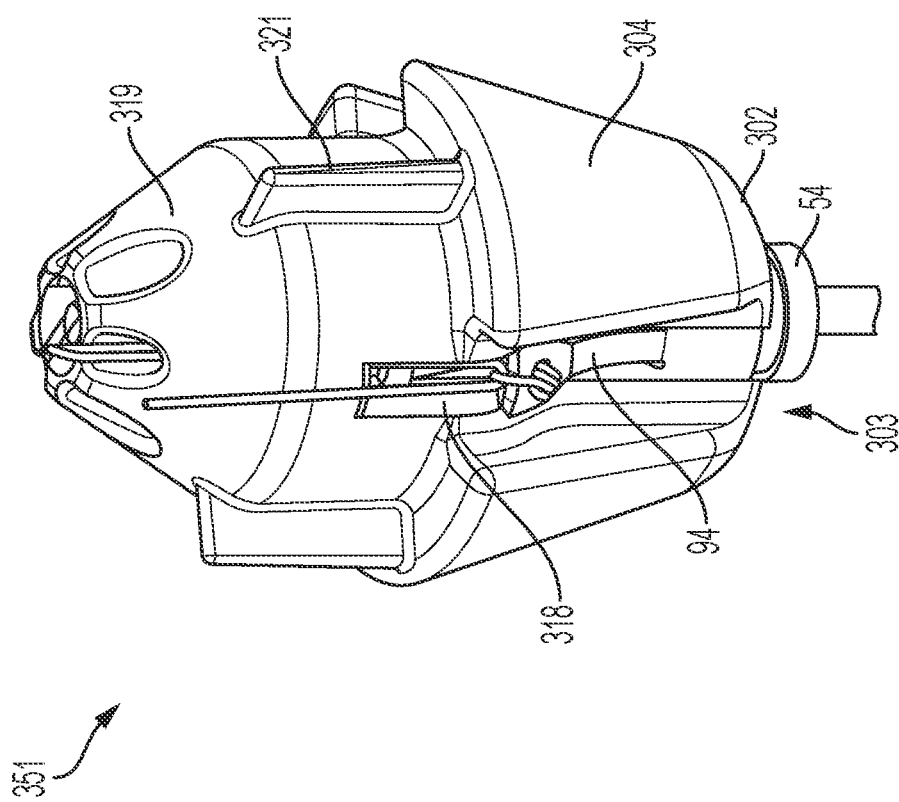
FIG. 29 is a perspective view of the entire prosthesis delivery cap with locking components.
Figure 30:
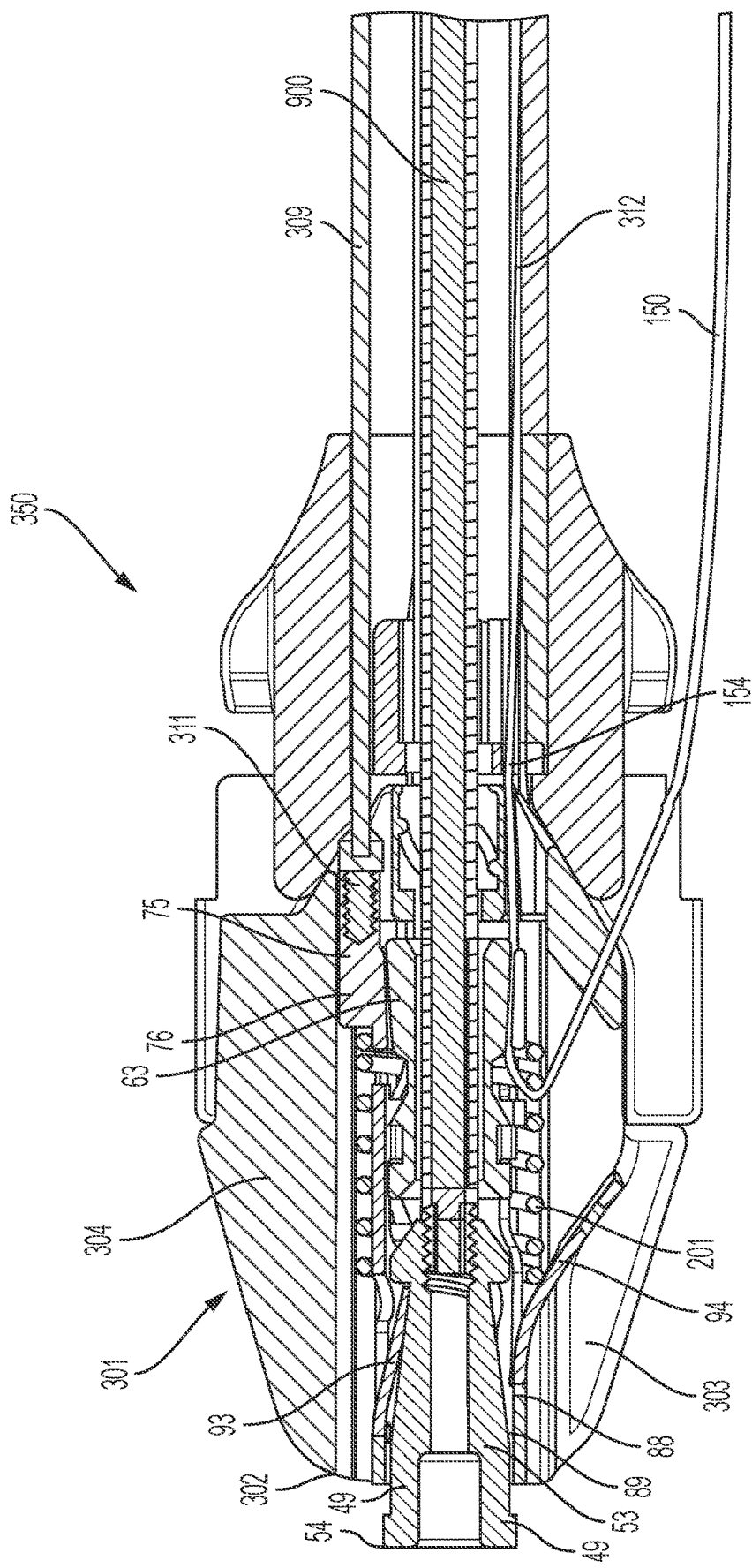
FIG. 30 is a cross-sectional side view of a locking delivery system with locking components and simplified tether routing.
Figure 31:
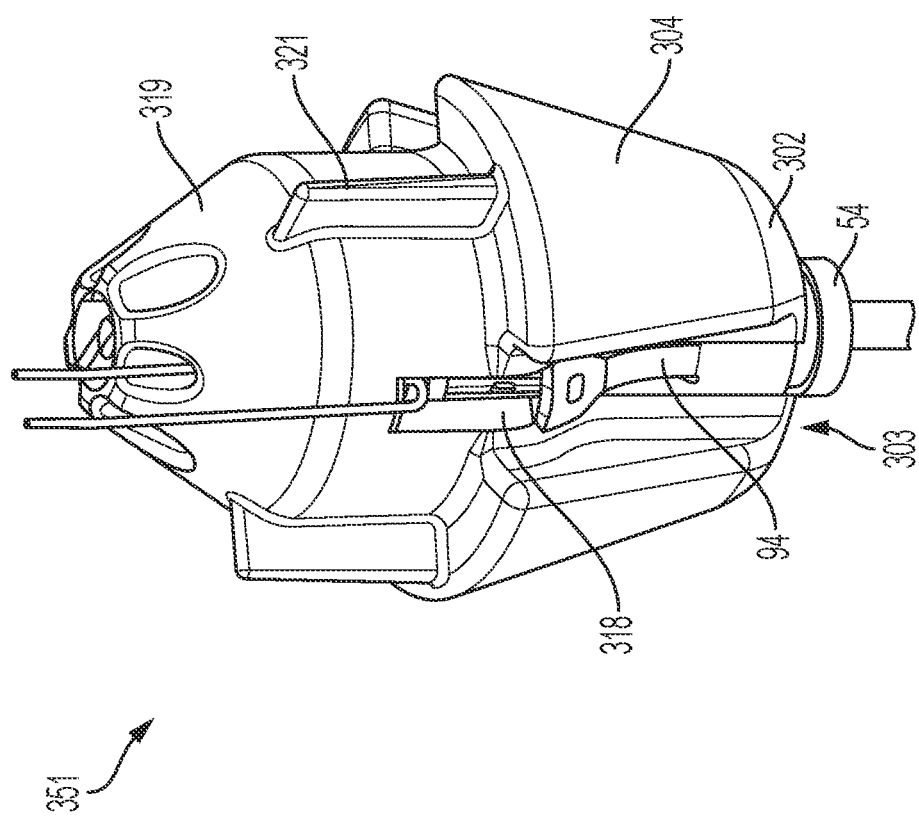
FIG. 31 is a perspective view of the entire prosthesis delivery cap with locking components with simplified tether routing.

Referring to FIGS. 28-29, the lock delivery system 350 including the lock components (lock cap 49, lock cone 63, lock collar 75, or tether swivel 88) are shown in FIG. 28 and the prosthesis delivery cap/lock components 351 in FIG. 29. FIG. 30 shows the lock delivery system/lock components 350 with simplified routing of tether 150 as described with respect to FIGS. 23-24 and FIG. 30 shows the prosthesis delivery cap/lock components 351 with simplified routing of tether 150. FIG. 28 shows all components after the lock delivery system has passed over guidewire 900 and the tether swivel 88 has docked onto lock cap 49. In this aspect the end 54 of lock cap 49 has a larger diameter than lumen 307 (FIG. 25), so that end 302 of the prothesis delivery system cap 301 does not extend past end 54. The lumen 307 is large enough to accommodate the lock cap body 53 and associated tether swivel base 89 and at least one locking arm 93. As shown in cross-section in FIG. 28 and in perspective in FIG. 29, the at least one tether arm 94 extends from tether swivel base 89 and rests in the tether arm groove 303. Within lumen 307, the rest of the locking system 110 (FIG. 19) extends proximally. As shown in FIG. 28, the end 311 of lock collar control rod 309 connects to the lock collar 75 via complementary threads 78 within the lock collar connector 76. The tether 150 is configured as per FIG. 20. Additionally, following the description above the interbody segment 153 enters the cap tether window 318 creates loop 154 and exits out the window 318 as lock tether segment 156. Loop 154 is connected to loop 313 (FIG. 25) of tether control line 312. The at least one tether control line 312, lock collar control rod 309, and guidewire 900 extend proximally through lock delivery system shaft 308, and all of these components exit the body and are connected to a lock delivery system controller (not shown).

Docking and Basline Locked State

Figure 33:
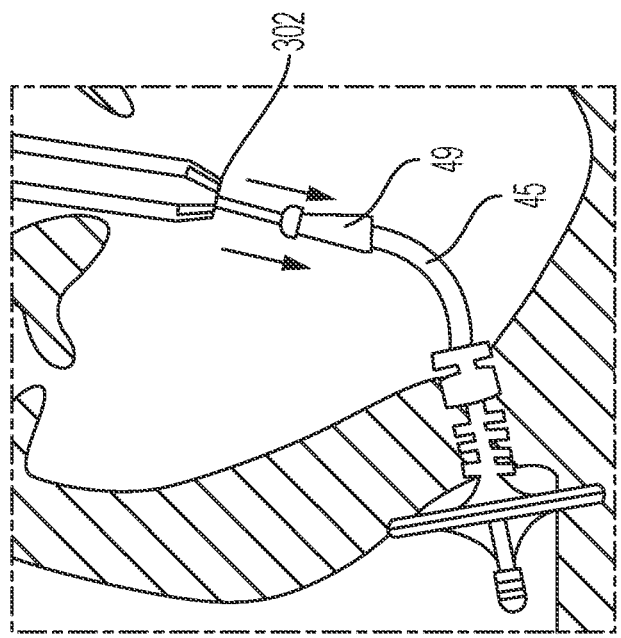
FIG. 33 is a magnified cut-away perspective view of the lock delivery system advancing to the anchor cap, which was placed with anchor support across the interventricular septum.
Figure 32:
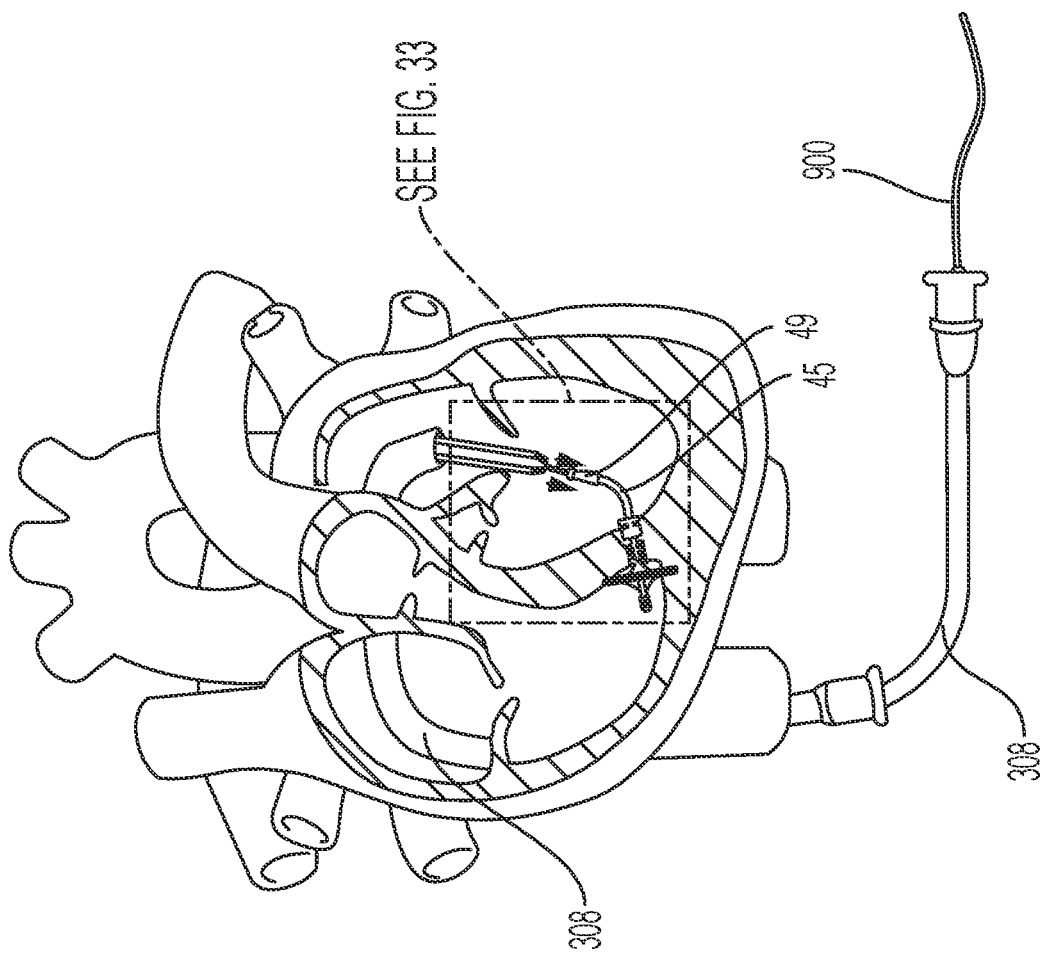
FIG. 32 is a cross-sectional perspective view of the lock delivery system advancing to the anchor cap, which was placed with anchor support across the interventricular septum.
Figure 34:
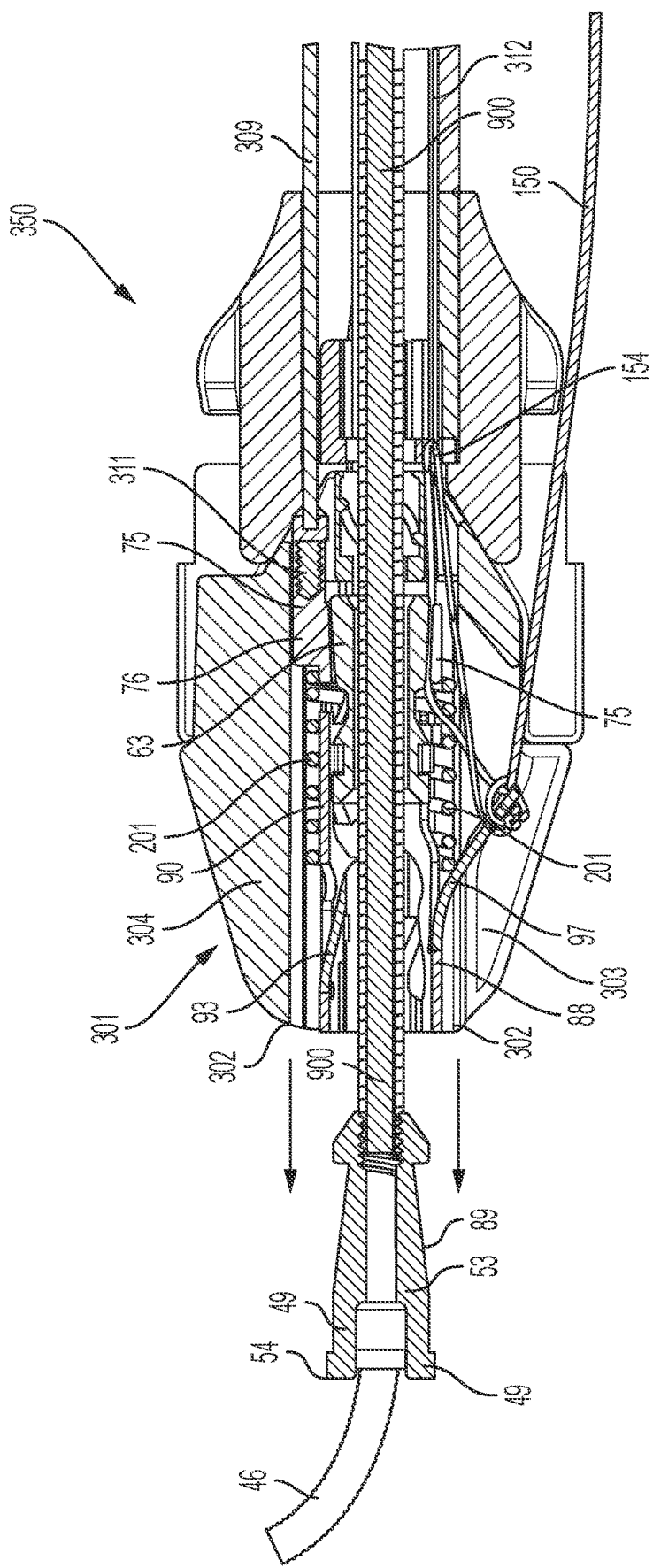
FIG. 34 is a cross-sectional side elevational view of the lock delivery system advancing to the anchor cap.

FIG. 32-34 illustrate the locking system 350 including the lock components (lock cap 49, lock cone 63, lock collar 75, or tether swivel 88) advancing over guidewire 900 for the purpose of locking a mitral prosthesis to an anchoring system as shown in FIG. 1, although the same process may be used for any of the other applications as shown in FIGS. 2-8. In use, whether the lock cap 49 is attached to an anchoring system 45 with/without a flex connector 46, to an extension member, or directly to another intracardiac implant, position of the lock cap 49 is stabilized by both the connection of the lock cap end 54 to distal elements and by the connection of the lock cap 51 to the proximal guidewire 900 via complementary threads. Thus, the stable position of lock cap 49 provides a platform so that the lock 200 may change from its baseline locked state to its unlocked state.

Figure 35:
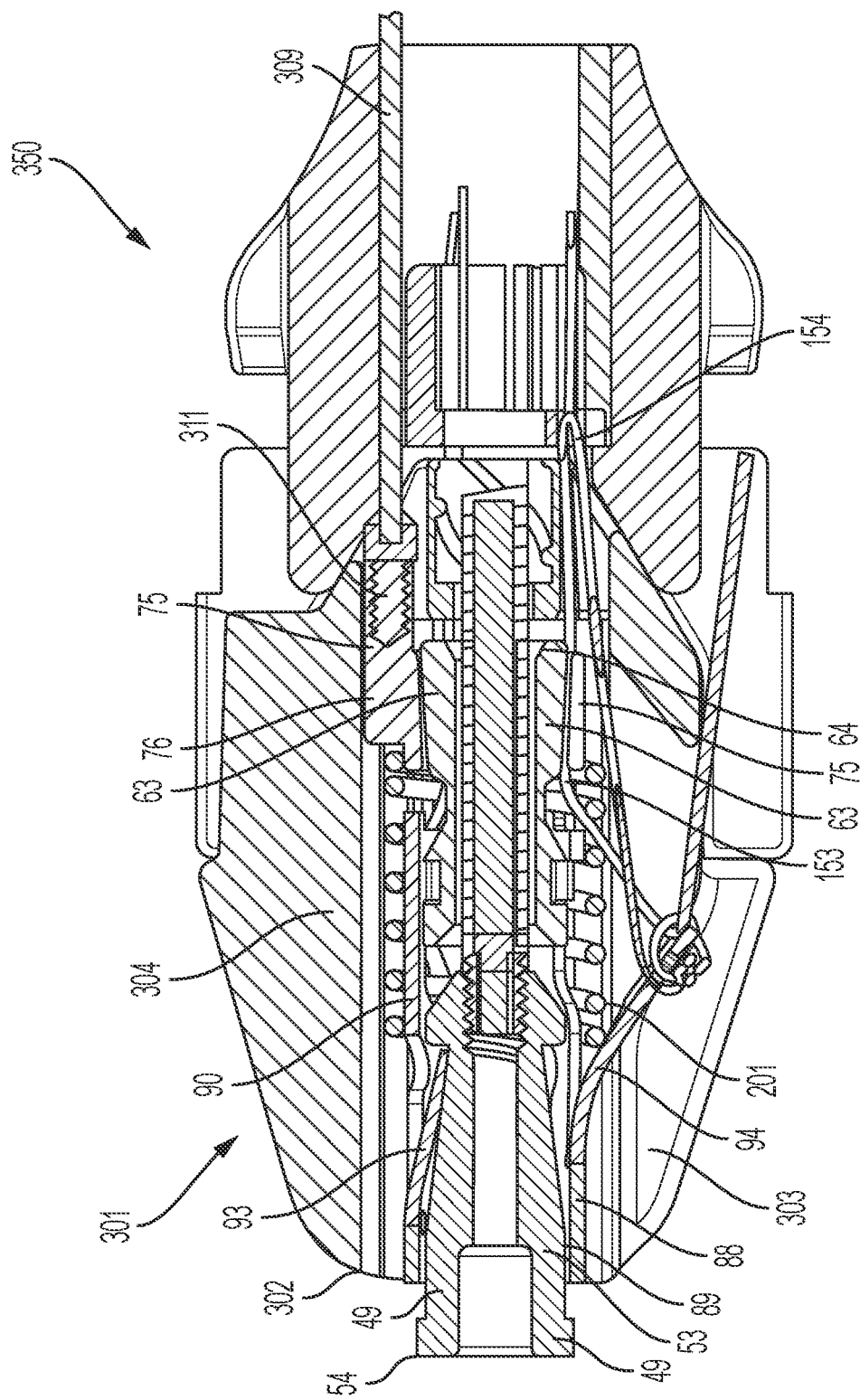
FIG. 35 is a cross-sectional side elevational view of the lock delivery system docked onto the anchor cap, and in the locked position.
Figure 36:
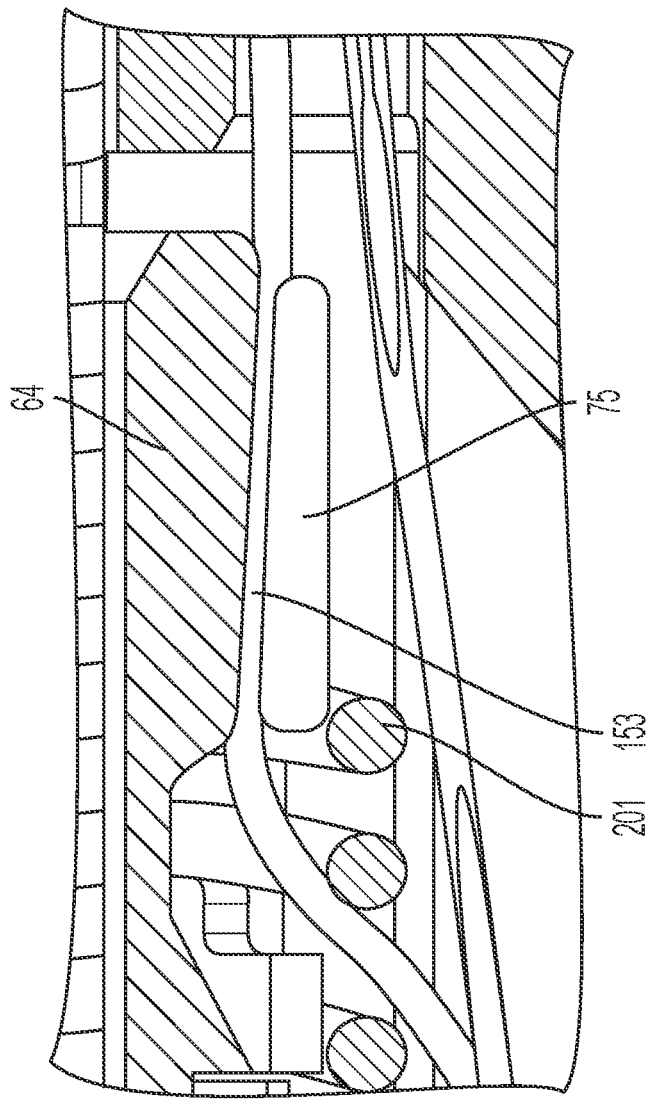
FIG. 36 is a magnified cross-sectional side elevational view of the tether locked.

FIG. 34 illustrates the locking system 350 as the tether swivel 88 is advanced distally. FIG. 35 illustrates the tether swivel 88 coupled to the lock cap 49. In this baseline state, the system is locked. Specifically, the locking spring 201 is expanded, urging the lock collar 75 upwards or proximally with respect to the locking cone 63 tapered surface 64, thereby pinching the interbody segment 153 of the tether 150, thereby fixing the length of the implant segment 151 of the tether 150. FIG. 36 is a magnified view of the interbody segment 153 being pinched by the lock collar 75, urged upwards by lock spring 201, and the locking cone tapered surface 64.

Unlocking Tether(s)

Figure 37A:
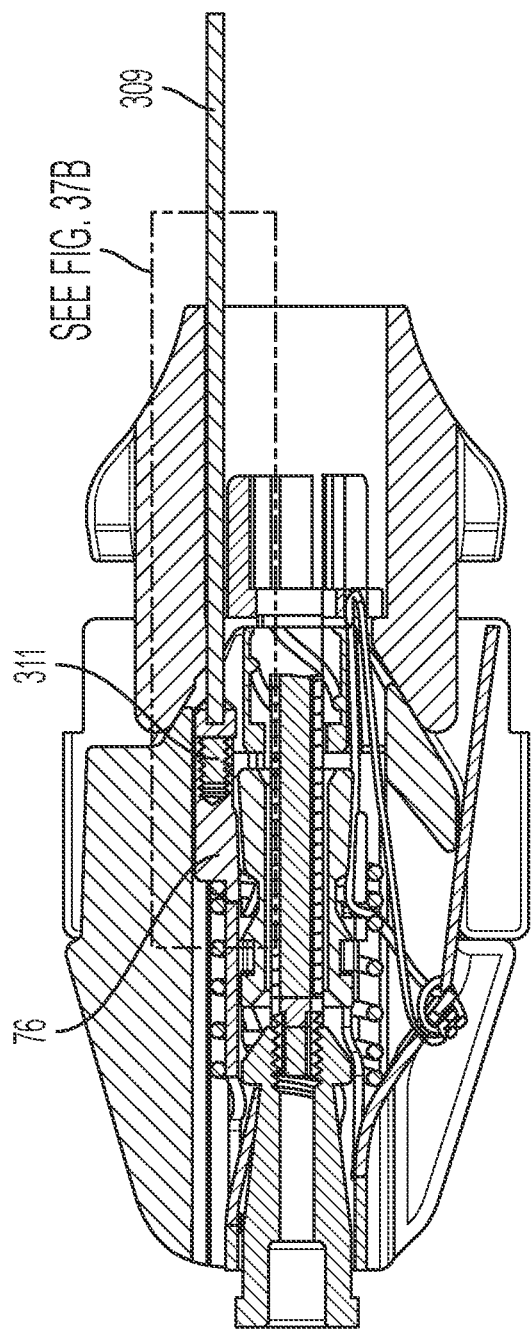
FIG. 37A is a cross-sectional side elevational view of the lock delivery system in the unlocked position.
Figure 37B:
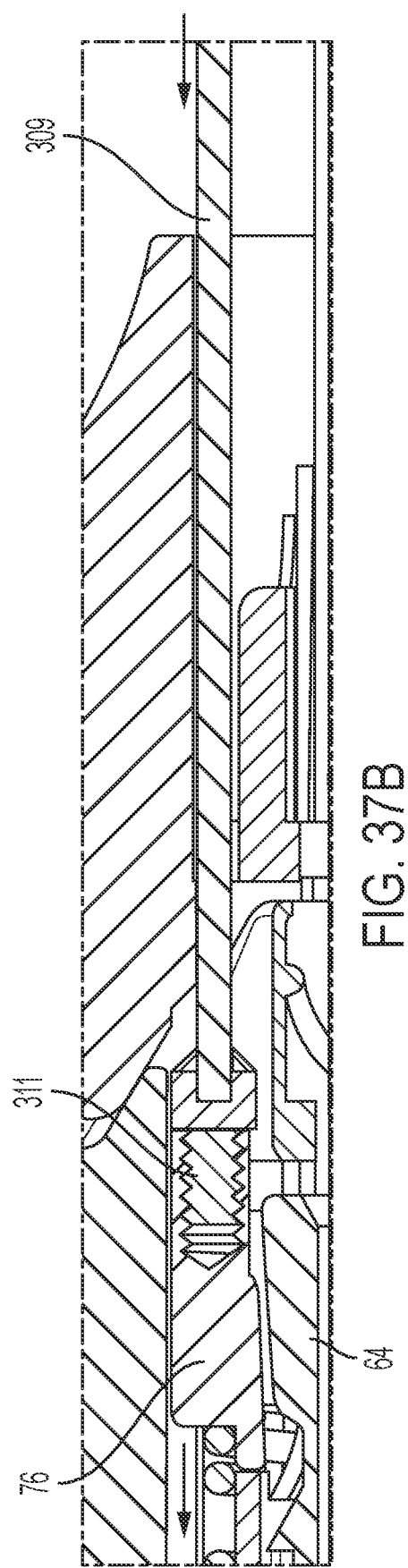
FIG. 37B is a magnified cross-sectional side elevational view of the lock collar control rod pushing the lock collar inferior to the lock cone so that the lock delivery system is in the unlocked position.
Figure 39:
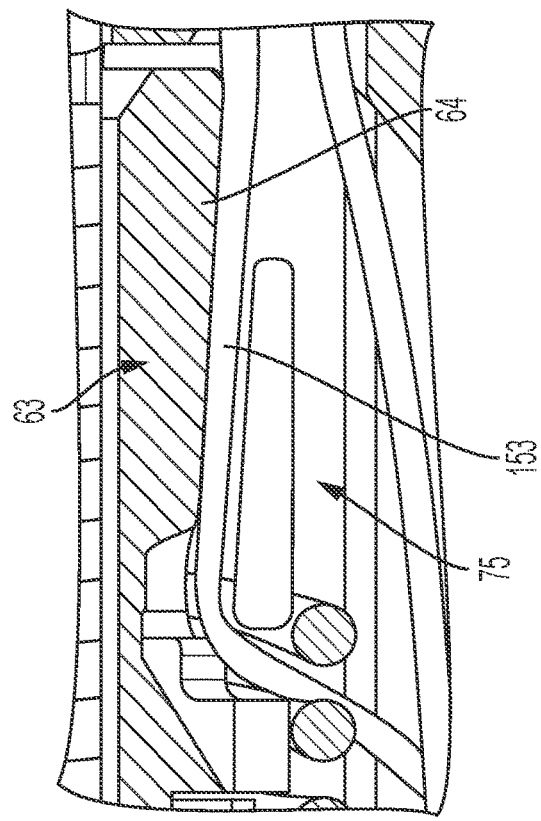
FIG. 39 is a magnified cross-sectional side elevational view of the lock collar and lock cone in the unlocked position.
Figure 38:
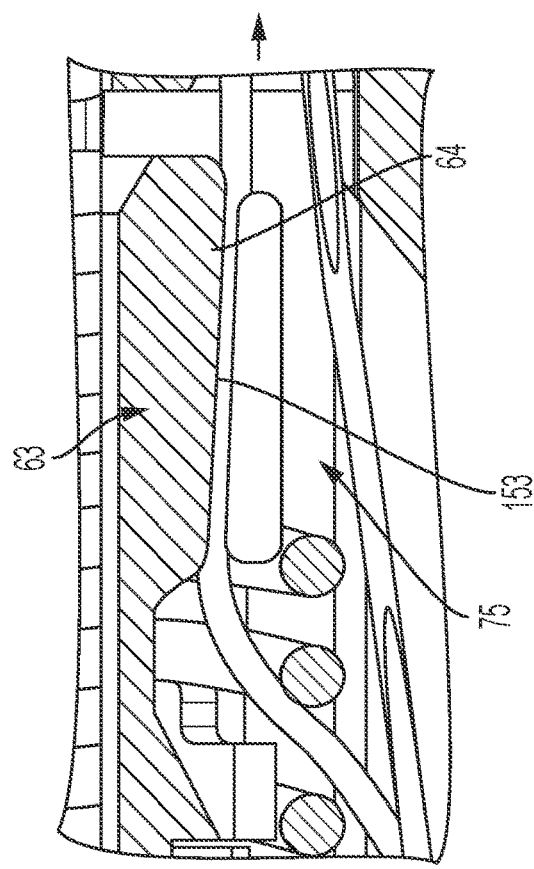
FIG. 38 is a magnified cross-sectional side elevational view of the lock collar and lock cone in the locked position.

FIGS. 37A-B illustrate the step to unlock the system. Specifically, the lock collar control rod 309 is pushed, and via its end 311 pushes the lock collar connector 76, thereby translating the lock collar 75 inferior or distal to the tapered surface 64 of the lock cone 63. FIGS. 38-39 are magnified pictures of the locking mechanism. As shown in FIG. 38, at baseline the lock collar 75 is at the same level as or aligned with the lock cone 63, thereby minimizing the gap between the tapered surface 64 of the lock cone 63, and the internal wall of the lock collar 75, thereby trapping the interbody segment 153 of the tether 150. As shown in FIG. 39, when the lock collar control rod 309 pushes the lock collar 75 past the lock cone 63, the distance between the tapered surface 64 and internal wall of the lock collar 75 increases, thereby releasing the interbody segment 153 of the tether 150.

Adjusting Tether(s) Length

Now referring to FIGS. 40-41, when the lock is in the unlocked state as described above, the tether control line 312 is pulled, and via tether control line loop 313, pulls on loop 154 of the tether 150. Pulling on loop 154 will not change the length of lock tether segment 156, because it is fixed to tether knot 158. Pulling on loop 154 will pull interbody segment 153 upwards. As interbody segment 153 translates, implant segment 151 is pulled through tether loop 157. In this way, the length of implant segment 151 shortens, bringing any intracardiac implant attached to implant segment 151 via its proximal end 159, closer to the locking system. To allow the implant segment 151 to lengthen, releasing tension on tether control line loop 313 allows the interbody segment 153 to go downwards as the implant segment 151 is pushed upwards at its proximal end 159 by the systolic force of the cardiac contraction pushes the attached intracardiac implant upwards.

Figure 42:
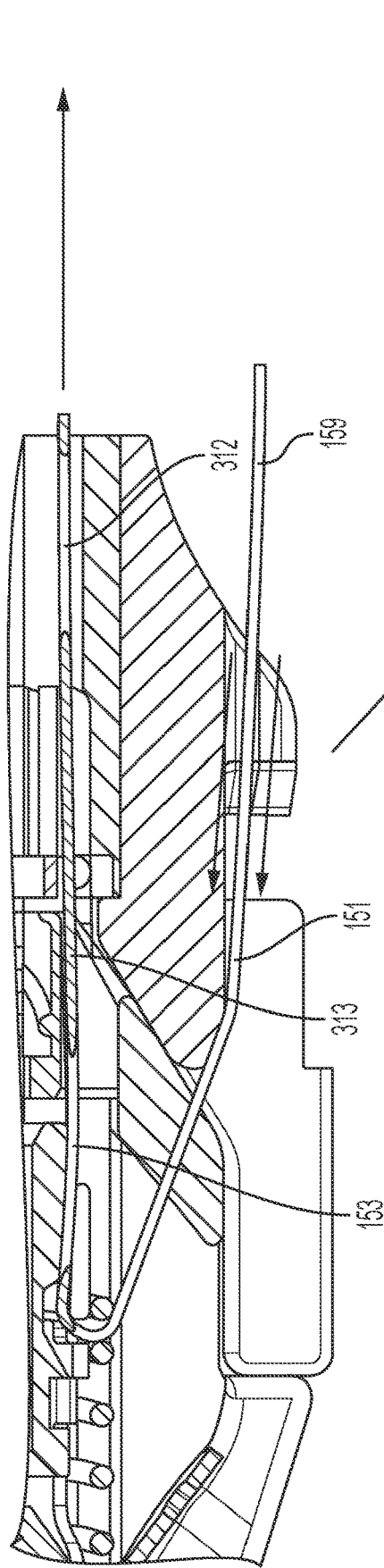
FIG. 42 is a magnified cross-sectional side elevational view of the tether with simplified routing in its original position.
Figure 43:
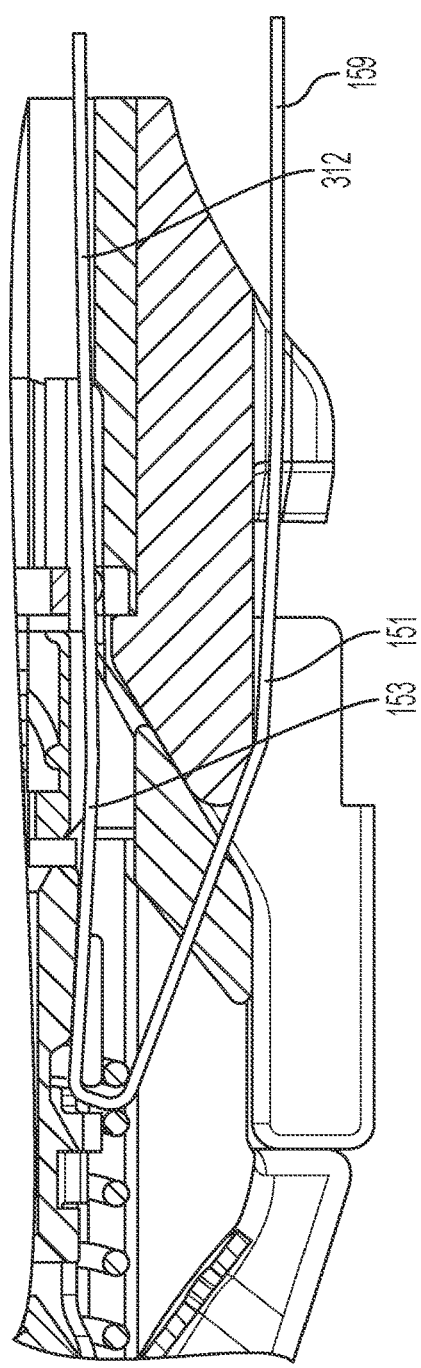
FIG. 43 is a magnified cross-sectional side-elevational view of the tether with simplified routing pulled upwards.

If the tether is in the simplified configuration as shown in FIGS. 42-43, then pulling the tether control line 312 pulls the proximal portion of interbody segment 153 upwards, thereby pulling implant segment 151 downwards, bringing any intracardiac implant attached to the implant segment 151 via its proximal end 159, closer to the locking system. Just like above, releasing tension of the tether control line 312 allows the interbody segment 153 to go downwards as the implant segment 151 is pushed upwards at its proximal end 159 by the systolic force of the cardiac contraction pushes the attached intracardiac implant upwards. After final adjustment the tether control line 312 and any portion of the implant segment 151 may be cut away, releasing the tether.

At anytime, the system can transition from the unlocked state shown in FIG. 39 and FIG. 40 to the locked state in FIG. 38 and FIG. 35. Specifically, releasing tension on the lock collar control rod 309 allows the lock collar 75 to be urged upwards by expansion of the lock spring 201; when the lock collar 75 moves upwards relative to the lock cone 63, the gap between the tapered surface 64 of the lock cone 63 and the inner surface of the lock collar 75 narrows, thereby pinching the interbody segment 153 in place, and fixing the length of the implant segment 151.

Alternative Lock Collar and Control Rod (FIGS. 44-48)

Figure 45:
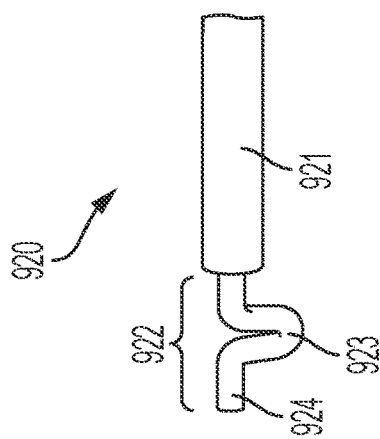
FIG. 45 is a side-elevational view of an alternative lock collar control rod.
Figure 44:
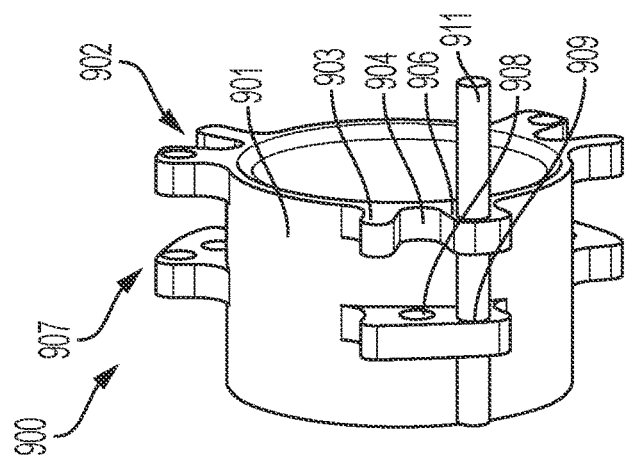
FIG. 44 is a perspective view of an alternative lock collar.

FIG. 44 illustrates a lock collar 900, and FIG. 45 illustrates a lock collar control rod 920. Like lock collar 75, lock collar 900 has a shape complementary to the top of the lock cone 63 and has a diameter larger than the tapered surface 64, to that the interbody segment 153 of the tether 150 runs between the tapered surface 64 of the lock cone 63 and the inner wall of the lock collar 900. Lock collar 900 has at least one control rod guide 902 attached to the outside of the lock collar and may be spaced anywhere along the circumference of the lock collar. The at least one control rod guide 902 has a guide tab 903, which may have the cross-section of any sinusoidal curve or any polygon, a guide valley 904, and a guide aperture 906. The guide valley 904 may be the shape of any curve of side of a polygon, and the guide aperture 906 may be circular, elliptical, or have the cross section of any polygon. Distal to the at least one control rod guide 902 is at control rod guide stabilizer 907, which may take any shape, and has a stabilizer aperture 908, and an end aperture 909. Each aperture may take any shape. A limiting rod 911 extends through the guide aperture 906 and through the end aperture 909.

FIG. 45 illustrates a lock collar control rod 92, which has a shaft 921 and a control rod limiter 922, comprised of limiter tab 923, and end 924. Shaft 921 may be a column of any length and diameter and have any type of cross-sectional shape. Control rod limiter 922 is a column of smaller diameter than shaft 921, with a protruding limiter tab 923, which may be a bent section of control rod limiter 922 or may be a separate element fused to the control rod limiter 922.

Figure 46:
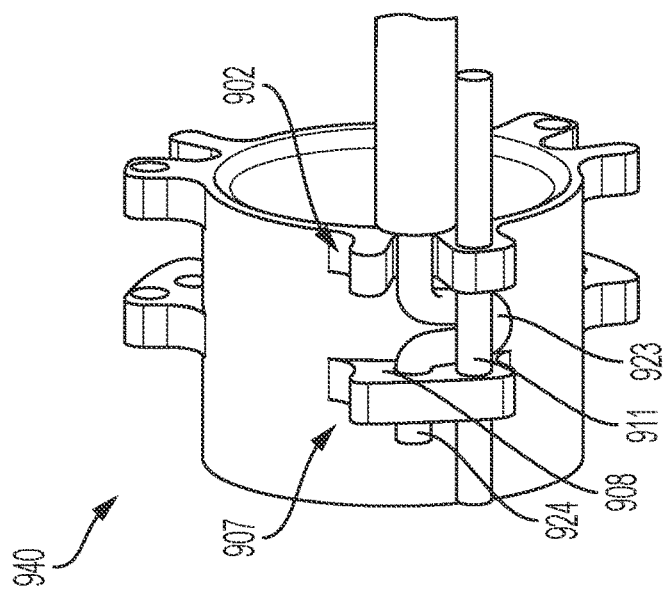
FIG. 46 is a perspective view of the alternative lock collar connected to the lock collar control rod.

Alternative Lock Collar and Control Rod Assembly (FIG. 46)

FIG. 46 shows how lock collar control rod 920 is attached to lock collar 900 in the control position. The end 924 of the control rod limiter 922 of the lock collar control rod 920 inserts into stabilizer aperture 908 of the control rod guide stabilizer 907 of the lock collar 900. In the control configuration, the limiter tab 923 of the control rod limiter 922 prevents rotation of the lock collar control rod 902 past the limiting rod 911. The proximal portion of the control rod limiter 922 rests in the guide valley 904 of the control rod guide 902. In this configuration, movement of the lock collar control rod 920 moves the whole lock collar 900.

Disconnecting Alternative Lock Collar from Control Rod (FIGS. 47-48)

Figure 47C:
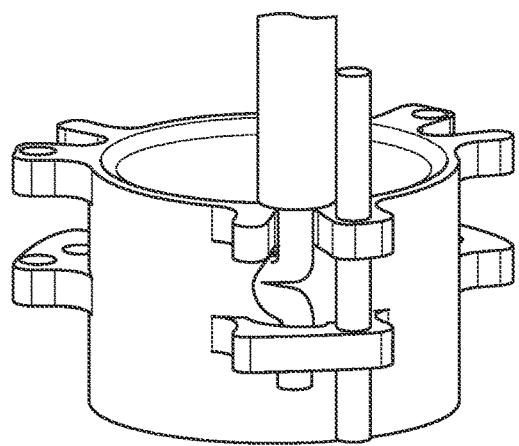
FIG. 47C is a perspective view of the alternative lock collar connected to the lock collar control rod, which has rotated radially away from the lock collar control rod.
Figure 47B:
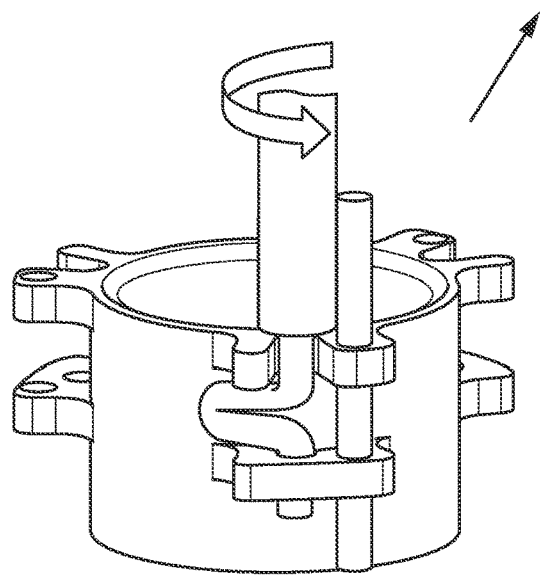
FIG. 47B is a perspective view the alternative lock collar connected to the lock collar control rod, which has been rotated 180 degrees.
Figure 47A:
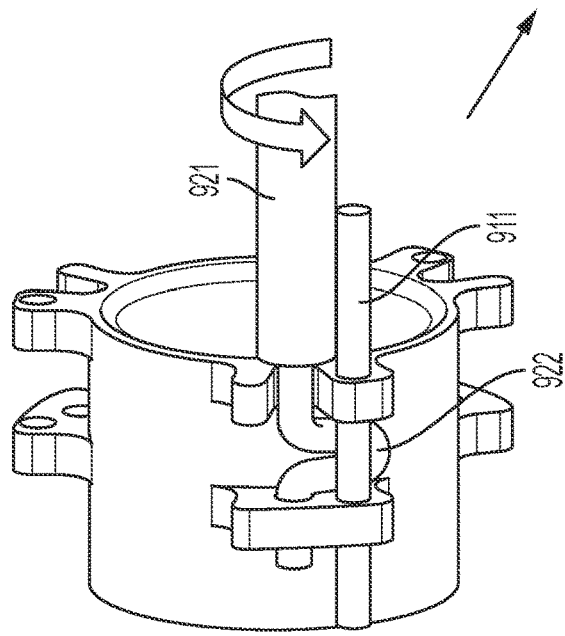
FIG. 47A is equivalent to FIG. 39.

Now referring to FIGS. 47A-C, the lock collar control rod 920 may be rotated by rotation of shaft 921. With this rotation, control rod limiter 922 rotates away from limiting rod 911 until the control rod limiter 922 is pointing away from the body of the lock collar 900.

Figure 48B:
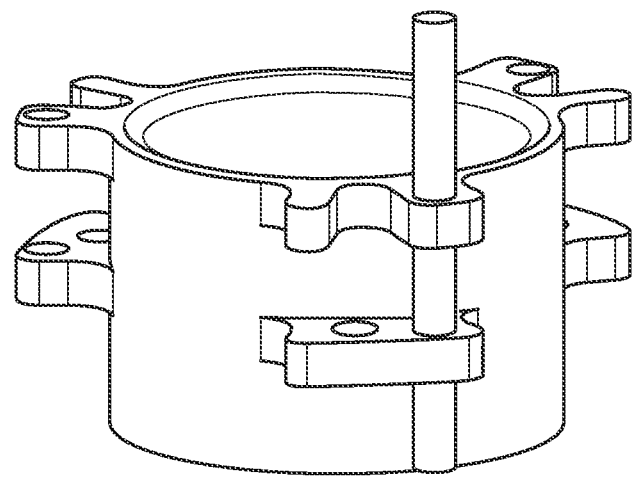
FIG. 48B is a perspective view of the alternative lock collar after the lock collar control rod has been removed.
Figure 48A:
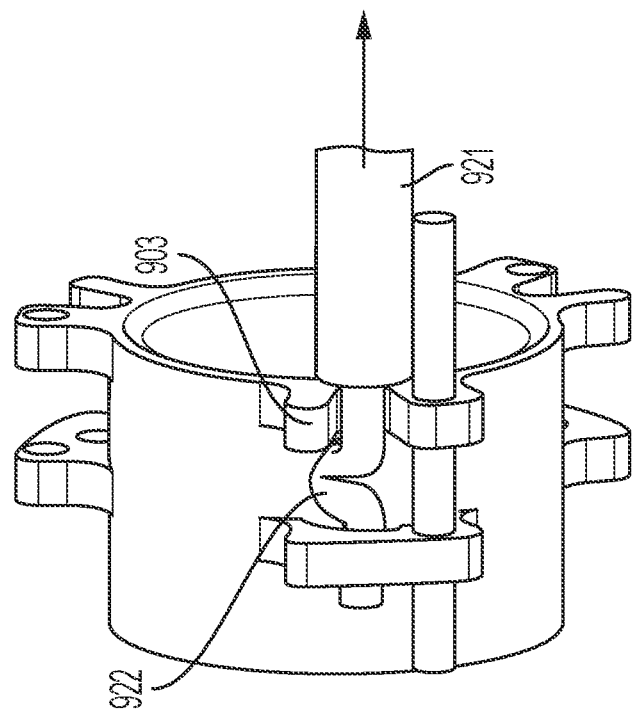
FIG. 48A is equivalent to FIG. 43C.

Referring to FIGS. 48A-B, once the control rod limiter 922 has rotated past the plane of the guide tab 903 of the control rod guide 902 of the lock collar 900, the control rod limiter 922 is free to move past the control road guide 902. At this point, pulling the shaft 921 allows the entire lock collar control rod 92 to be disconnected from the lock collar 900.

Figure 49:
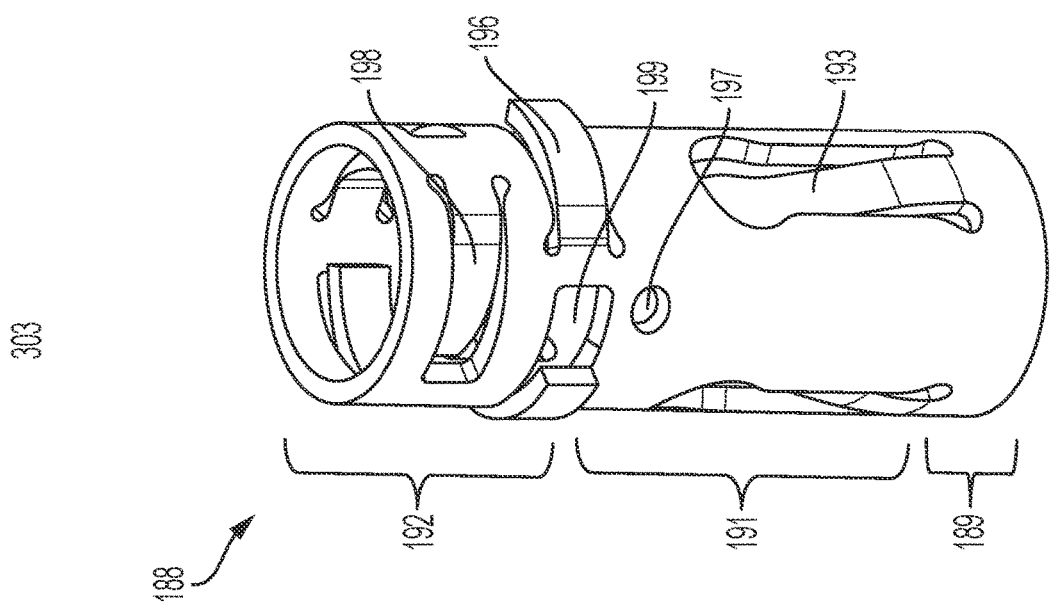
FIG. 49 is a perspective view of a tether swivel without arms.

Tether Swivel Without Arms (FIG. 49)

Referring to FIG. 49, the at least one tether swivel 188 includes a tether swivel base 189, shaft body 191, shaft collar 192, at least one locking arm 193, at least one spring contact tab 196, at least one coupling arm 198, and at least one tether eyelet 197. The tether swivel base 189 is shown as cylindrical, although other polygonal cross-sections are possible, and the base 189 has an internal diameter larger than the lock cap body 53, the outer diameter of base 189 is shown smaller than the outer diameter of the lock cap distal end 54. The shaft body 191 extends from the base 189 to the shaft collar 192. The shaft body 191 may be the same or different thickness of shape compared to the base 189. In the upper half the shaft body 191 is at least one tether swivel eyelet 197, that may have a circular, elliptical, or any other polygonal shape. Extending along part or all of the length of the shaft body 191 and connected to the base 189 is at least one locking arm 193, which extends from the base 189 to below the top of the shaft body 191. Each locking arm 193 bends toward the center of the tether swivel, and each locking arm 193 may bend at the same or variable angle from each other, and may be of the same or variable width, length, or thickness. The shaft collar 192 comprises at least one spring contact tab 196, at least one tether slot 199, and at least one coupling arm 198. The shaft collar 192 is shown as cylindrical, although other polygonal cross-sections are possible. The at least one spring contact tab 196 extends outward from the diameter of shaft collar, either by intrinsic properties or another element (not shown) and may be shaped as a straight or curved member and may have the outline of any polygon. The at least one coupling arm 198 also may take any shape, and bends inwards toward the center of the swivel. In another aspect the tether swivel 188 may composed of any alloy or covered with any membrane as described for tether swivel 188 as set forth above.

Figure 51:
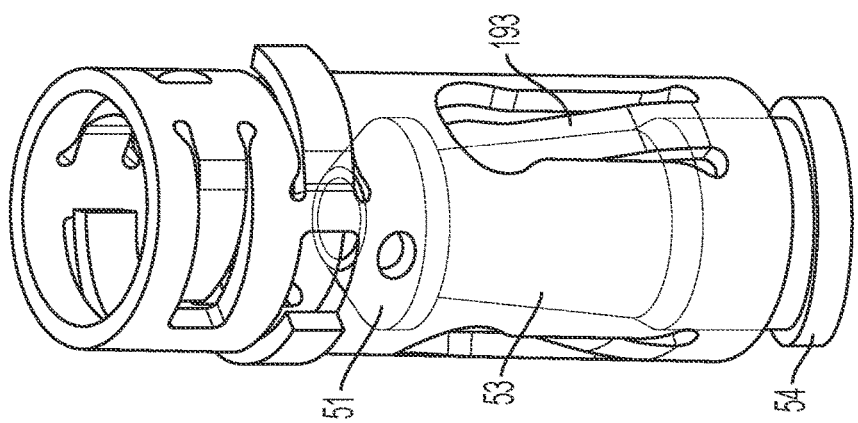
FIG. 51 is a cut-away perspective view of a tether swivel without arms coupled to a lock cap.
Figure 50:
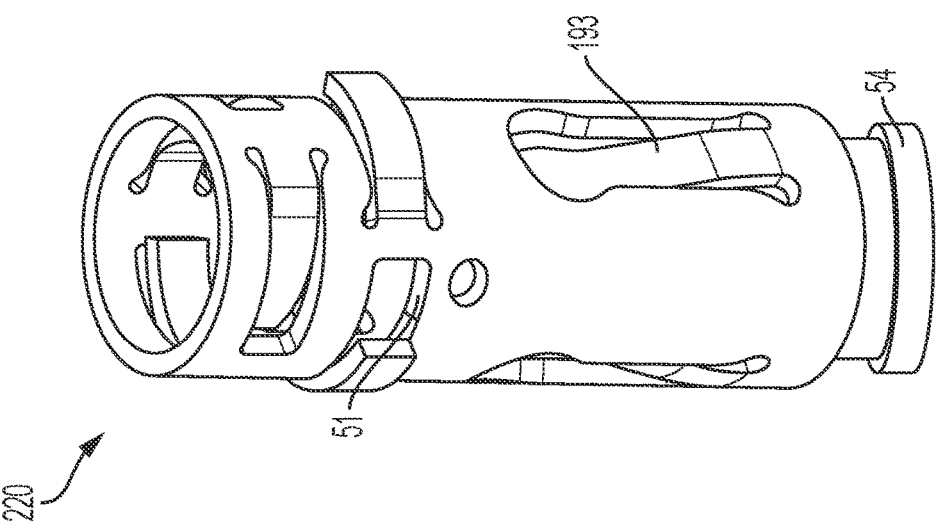
FIG. 50 is a perspective view of a tether swivel without arms coupled to a lock cap.

Tether Swivel Without Arms and Lock Cap Assembly (FIGS. 50-51)

Now referring to FIGS. 50-51, the tether swivel/lock cap assembly 220 is comprised of the lock cap 49 and the tether swivel 188. In this aspect the lock cap body 53 is configured to be attached to the tether swivel base 189 and one or more locking arms 193. Specifically, the lock cap end 54 has a diameter larger than the tether swivel base 189 of the tether swivel 188, preventing the tether swivel 188 from going past the lock cap end 54. The lock cap body 53 as shown has a frustoconical shape (although other polygonal shapes are contemplated) such that the locking arms 193 of the tether swivel 188 bend inwards to abut the surface of the lock cap body 53, but the tips of the locking arms 193 rest below the lock cap head 51. The larger diameter of the lock cap head 51 compared to the proximal end of the lock cap body 53 prevents the locking arms 193 (bent inwards and abutting the lock cap body 53, and thus the tether swivel 188, from moving past the lock cap head 51.

Figure 54:
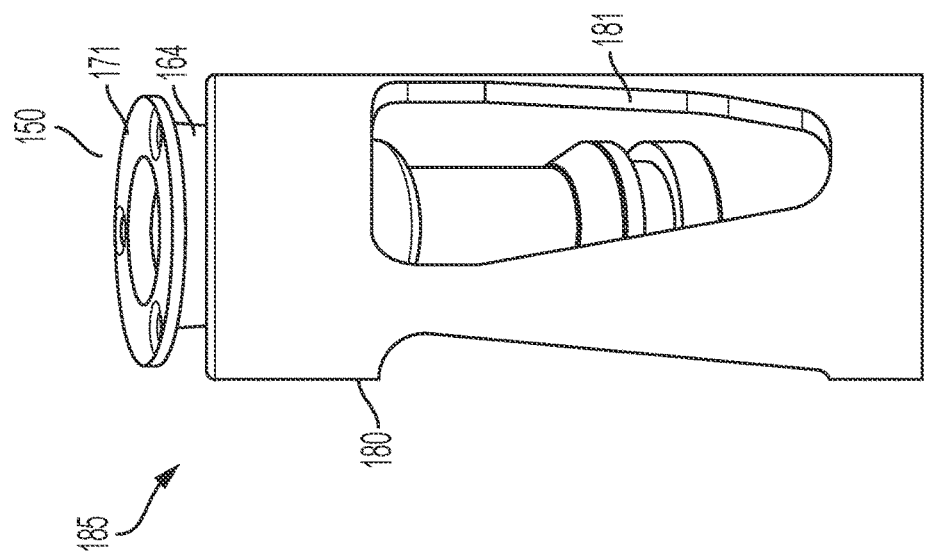
FIG. 54 is a perspective view of a long lock collar coupled to a long lock cone.
Figure 53:
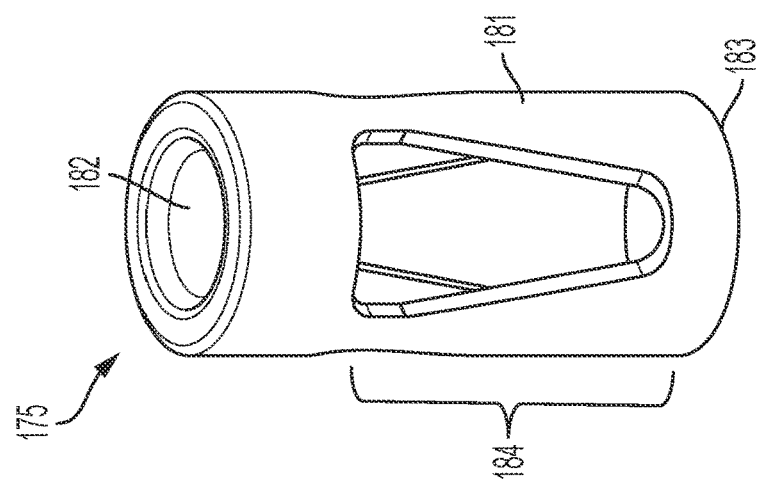
FIG. 53 is a perspective view of a long lock collar.
Figure 52:
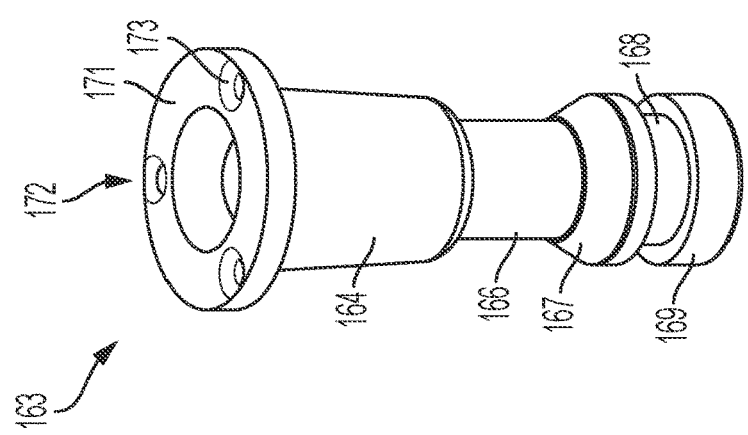
FIG. 52 is a perspective view of a long lock cone.

The Long Lock Cone and Lock Collar (FIGS. 52-54)

Referring to FIGS. 52-54, the long lock cone 163 includes lock cone proximal end 171, lock cone tapered surface 164, lock cone mid-section 166, lock cone assembly hood 167, lock cone assembly groove 168, lock cone end 169, and lock lumen 172, at least one tether alignment hole 173. The at least one long lock collar 175 consists of a lock collar body 181, at least one tapered window 184, lock collar body end 183, and lock collar lumen 182. In one aspect the tapered surface 164 has a reverse frustoconical shape, although any polygonal shape is contemplated, and has a diameter small than the lock collar body lumen 182, which has a complementary shape to tapered surface 164. Referring to FIG. 54, the lock collar 175 is pre-assembled on top of lock cone 163, such that the lock collar body 181 and lock lumen 182 are around the tapered surface 164 of the lock cone 163 and the lock collar lumen 182. In another aspect, the lock cone 163 or lock collar 175 is composed of any metal alloy or covered in any membrane as described above].

Figure 57:
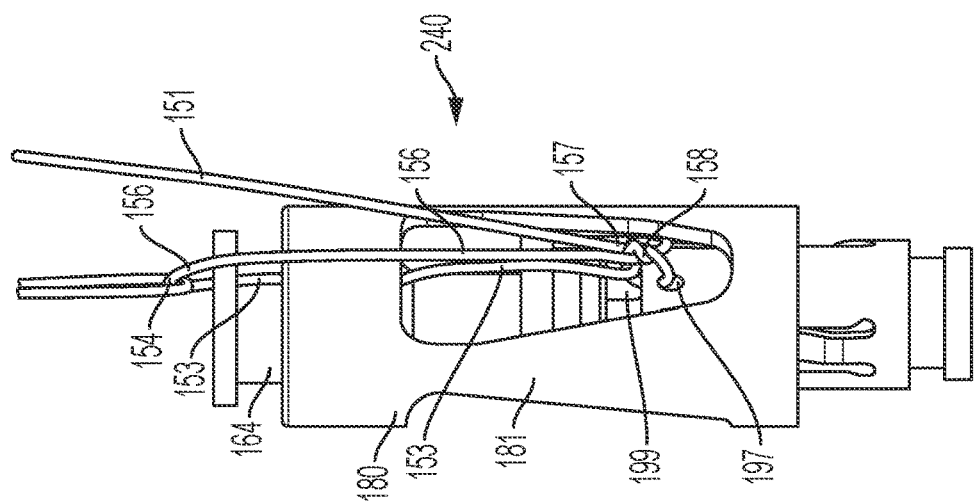
FIG. 57 is perspective view of the system of FIG. 55 with a tether attached.
Figure 56:
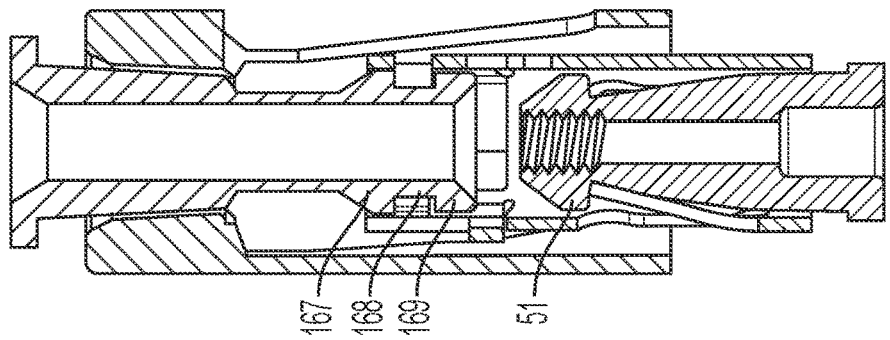
FIG. 56 is a cross-sectional perspective view of the tether swivel/lock cap assembly coupled with the lock cone and lock collar.
Figure 55:
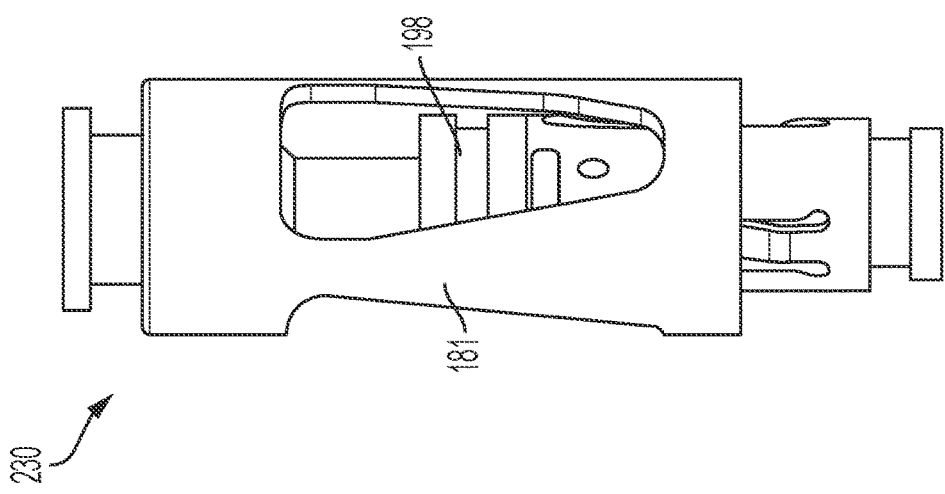
FIG. 55 is a perspective view of the tether swivel/lock cap assembly coupled with the lock cone and lock collar.

The Complete Locking System (FIGS. 55-57)

Figure 58:
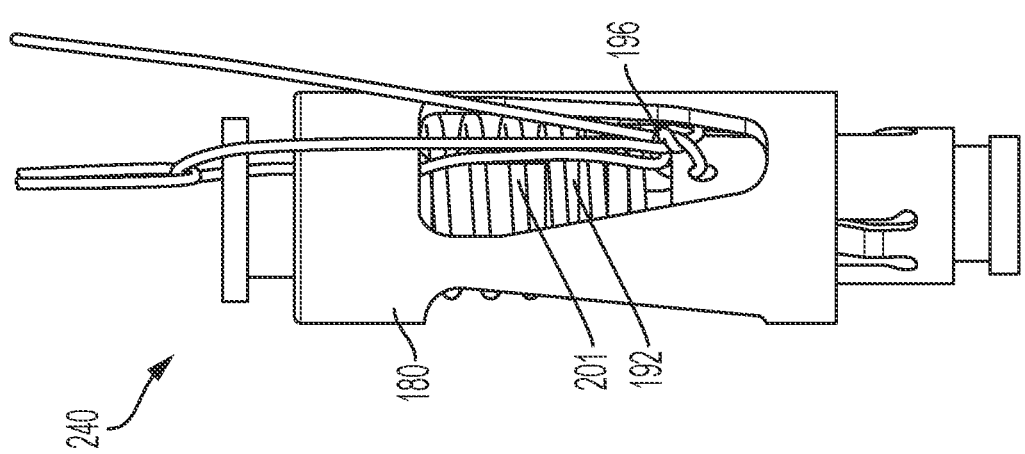
FIG. 58 is a perspective view of the system of FIG. 57 with the locking spring in place.

FIGS. 55-57 show the various components of the locking system and how they are assembled together with the complete locking system 240 shown in FIGS. 57 and 58. FIGS. 55-56 illustrate how the tether swivel/lock cone/lock collar assembly 230 is comprised of the tether swivel/lock cap assembly 220 of FIGS. 50-51 coupling to the lock cone/collar assembly 185 of FIG. 54. In this aspect end of lock cone 169 rests within the tether swivel 188 above the lock cap head 51, of the tether swivel/lock cap assembly 220, and the lock cone end 169 may or may not touch lock cap head 51. Above the lock cone end 169, the lock cone assembly groove 168 couples to the tether swivel 188 by at least one tether coupling arm 198, which bends into the assembly groove 168, in between the lock cone assembly hood 167 and the lock cone end 169

FIG. 57 illustrates how tether 150 is coupled to the tether swivel/lock cone/lock collar assembly 230. The implant segment 151 of each tether 150 is attached proximally to any portion of an intracardiac implant. Distally, the implant end 151 runs through the tether loop 157, within tapered window 184, next to the tether slot 199 of the tether swivel 188. Next, the implant segment 151 runs adjacent to the shaft collar 192, before becoming the interbody segment 153, which runs between the lock surface cone 164 and the lock collar top 180. The interbody segment 153 runs upwards through the tether alignment hole 173 of the long lock cone 163 until it loops around the tether control loop 154. After the tether control loop 154, the lock tether segment 156 runs along the side of the top of lock collar top 180 entering tapered window 184, forming tether knot 158, which encircles the tether eyelet 197 and tether window 199 of the tether swivel 188.

Referring now to FIG. 58 of the entire locking system 240, which comprises system of FIG. 57 and a locking spring 201. The locking spring 201 starts at or close to the at least one spring contact tab 196, wrapping around the tether swivel shaft collar 192 of the tether swivel 188, ending just below the lock collar 180 of the lock collar 175. The locking spring 201 may or may not encircle any aspect of the tether 150.

The locking spring 201 for this system may take any of the characteristics described above.

Figure 59:
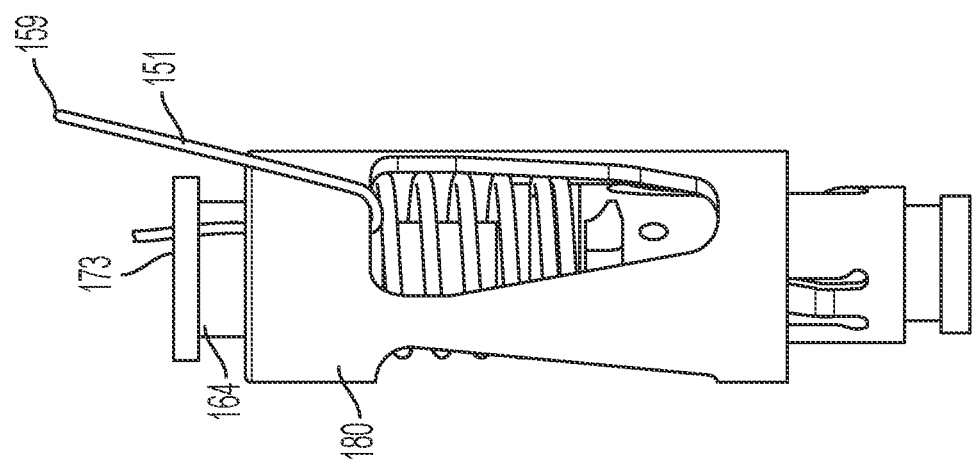
FIG. 59 is a perspective view of the system of FIG. 58 with the tether attached in alternative configuration.

The Lock System With Simplified Tether Routing (FIG. 59)

An alternative way to route the tether 150 is illustrated in FIG. 59. The proximal end 159 of the implant segment 151 of tether 150 is attached to the intracardiac implant. The implant segment 151 passes through tapered window 184, passing under the lock collar top 180, forming the interbody segment 153, which runs between the lock collar top 180 and the lock cone surface 164, going through the tether alignment hole 173, and extending proximally through the lock delivery system.

The Lock Delivery System (FIG. 60-63)

Figure 60:
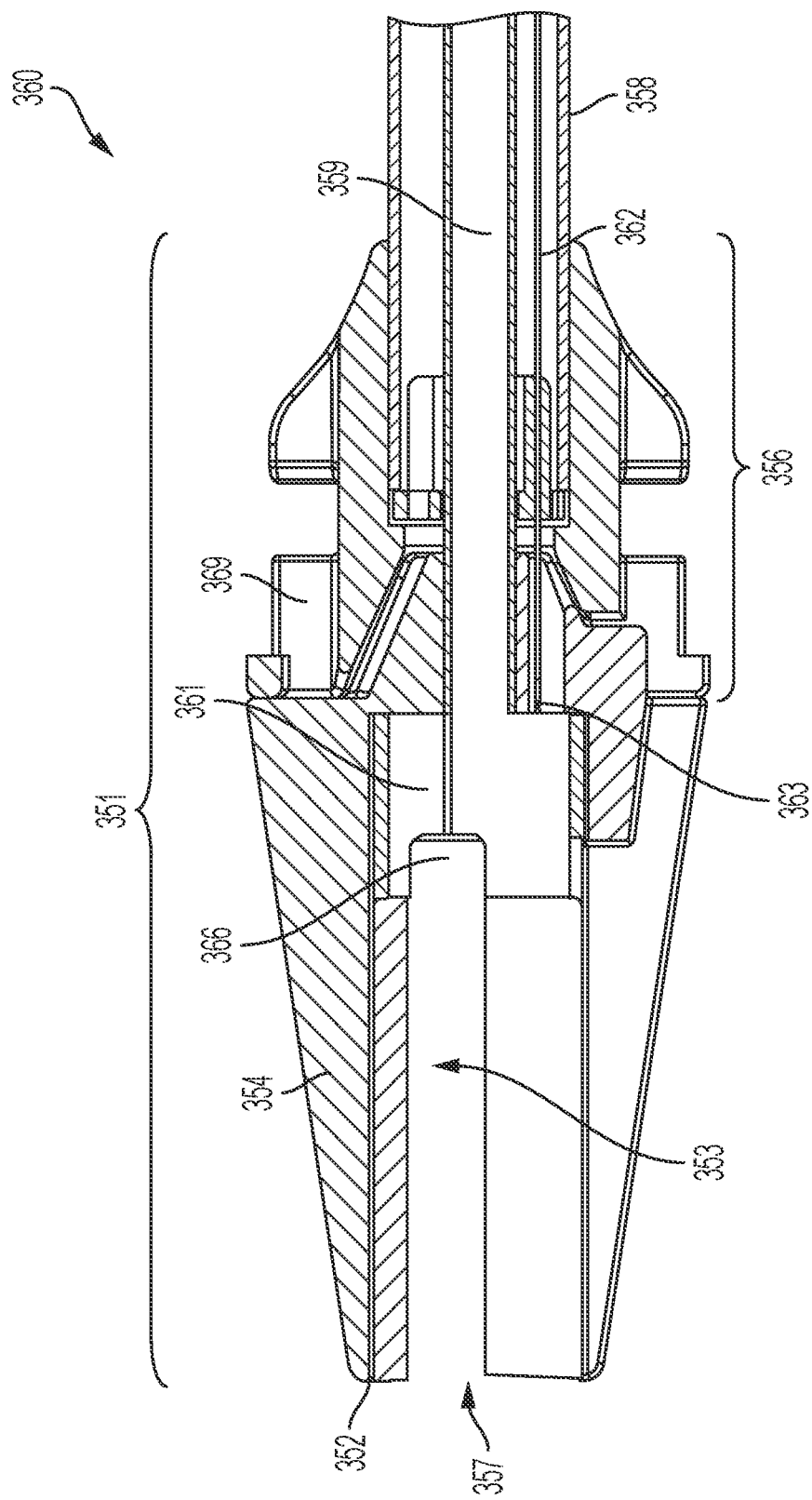
FIG. 60 is a cut-away side-elevational view of a locking delivery system without the locking components.
Figure 61:
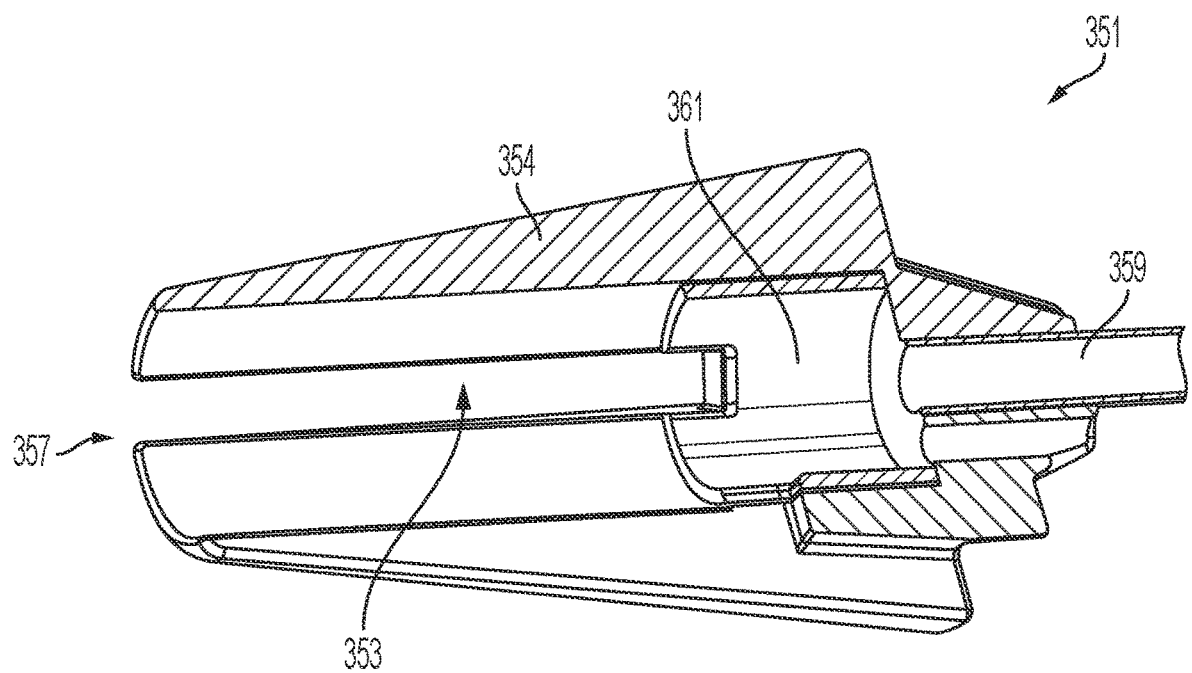
FIG. 61 is a perspective cut-away view of a locking delivery system without the locking components
Figure 62:
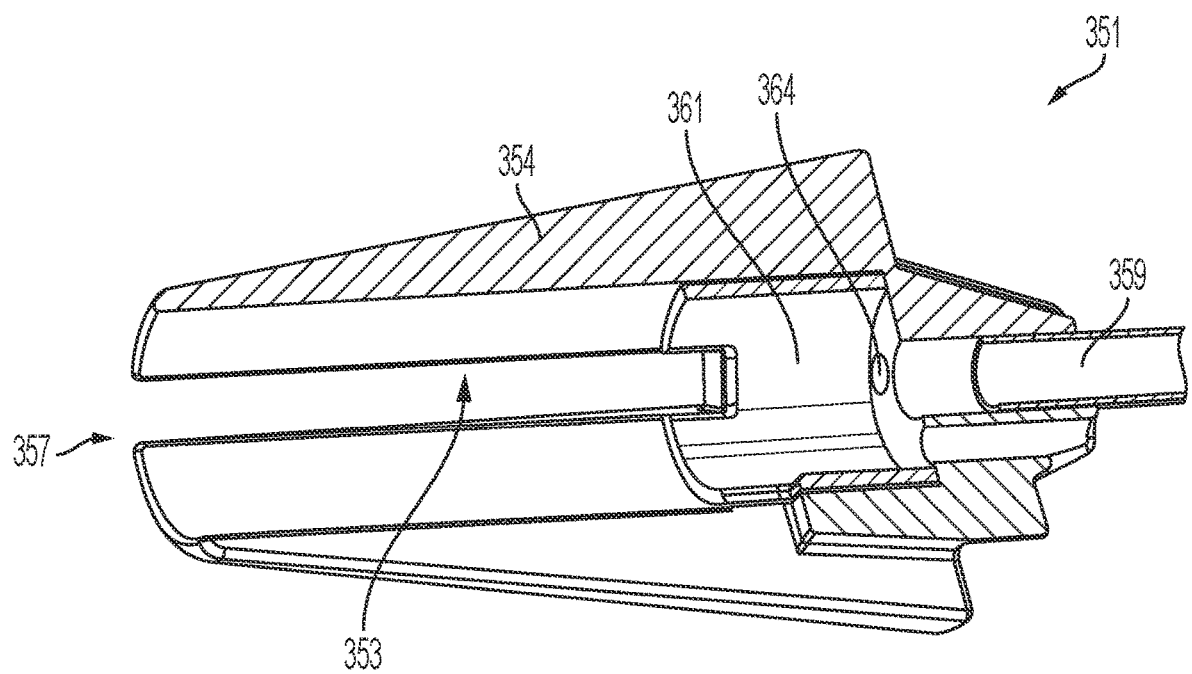
FIG. 62 is a perspective cut-away view of a locking delivery system without the locking components with the lock collar controller cut away from its end.
Figure 63:
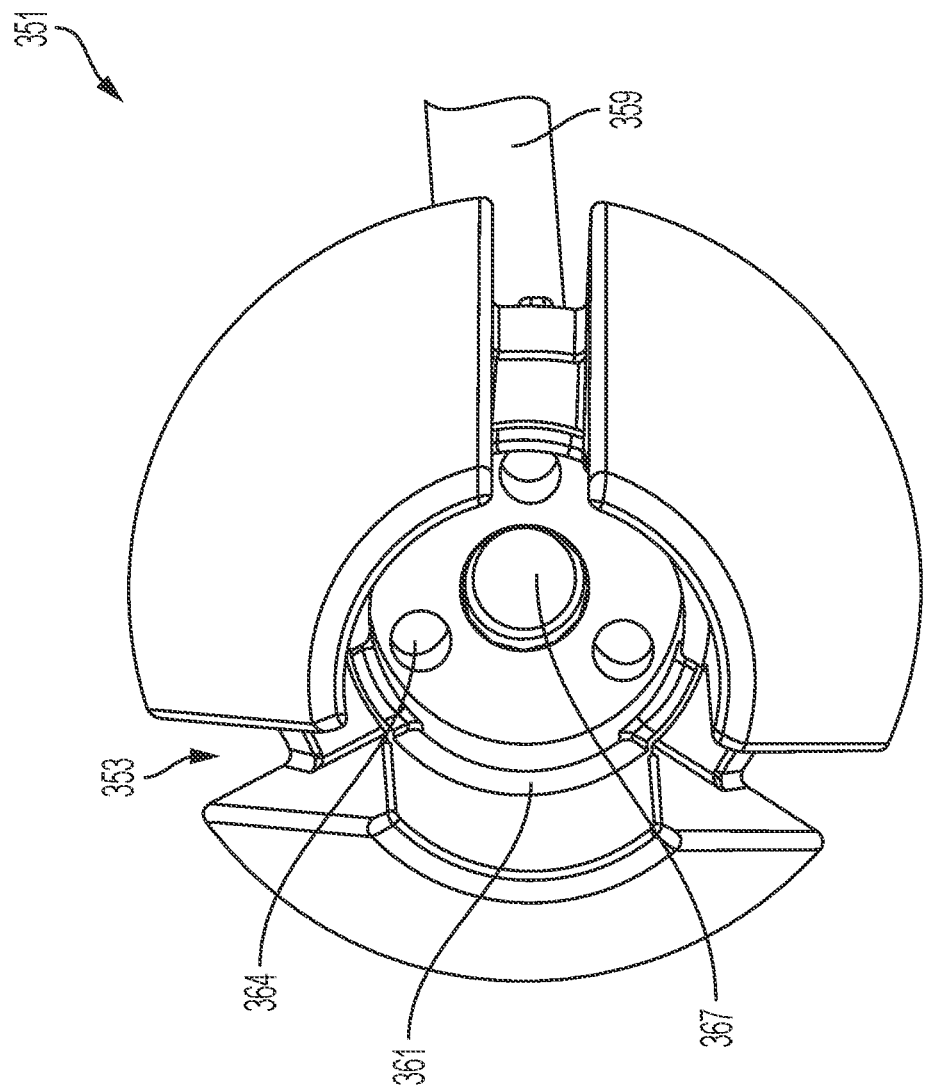
FIG. 63 is a perspective view looking at the end of the prosthesis delivery cap.

FIGS. 60-63 show the lock delivery system 360 without any of the lock components pre-loaded. FIG. 61 shows a longitudinal cross-section of the lock delivery system with a prosthesis delivery system cap 351 that has a distal end 352, proximal end 356, lumen 357 running through cap, at least one tether cap slot 353, outer surface 354, lock delivery system shaft 358, lock collar controller 359 with end 361, and at least one tether control line 362, and at least one tether control port 364 (in FIG. 62). When the prosthesis delivery system cap 351 is associated with a valve system, it is termed a valve delivery system (VDS) cap. FIG. 63 shows an end-on view of the lock cap illustrating the at least one tether control port 364, guidewire lumen 367.

The prosthesis delivery system cap 351 shown has a frustoconical shape distally, although other polyhedral shapes are not excluded. The proximal end 356 has a cylindrical based connected to a proximal conical segment 369. Each of the holes within the distal end may be spaced evenly or at variable distance, and may have the same or different diameter, may take any polygonal shape. The at least one tether cap slot 353 may have the same or different polygonal shape with same or variable width, length, and degree of angulation to accommodate the associated tether arm of the tether swivel. Above the tether cap slot 353, the at least one tether control port 364 may have any polygonal shape, width, and length to accommodate a tether. The lock collar controller 359 has a distal end 361 shown with a cylindrical shape although other shapes are possible, with at least one control slot 366 that has a complementary shape to at least one tether cap slot 353. The lock delivery system may be composed of any type of metallic alloy and may be covered by any biological or synthetic membrane as described according to alternative aspects of the invention described above.

Figure 64:
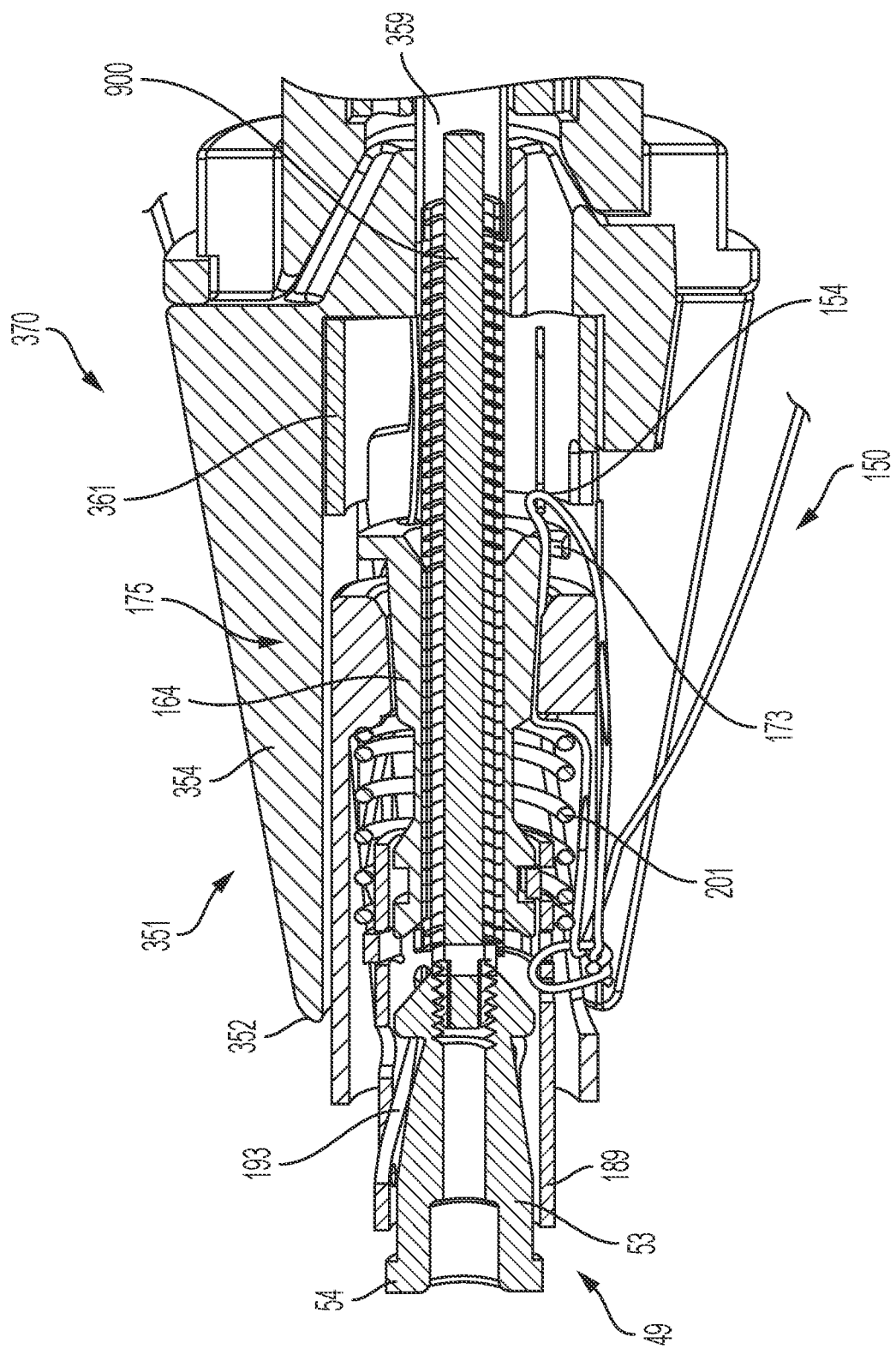
FIG. 64 a cut-away side-elevational view of a lock delivery system with locking components.
Figure 65:
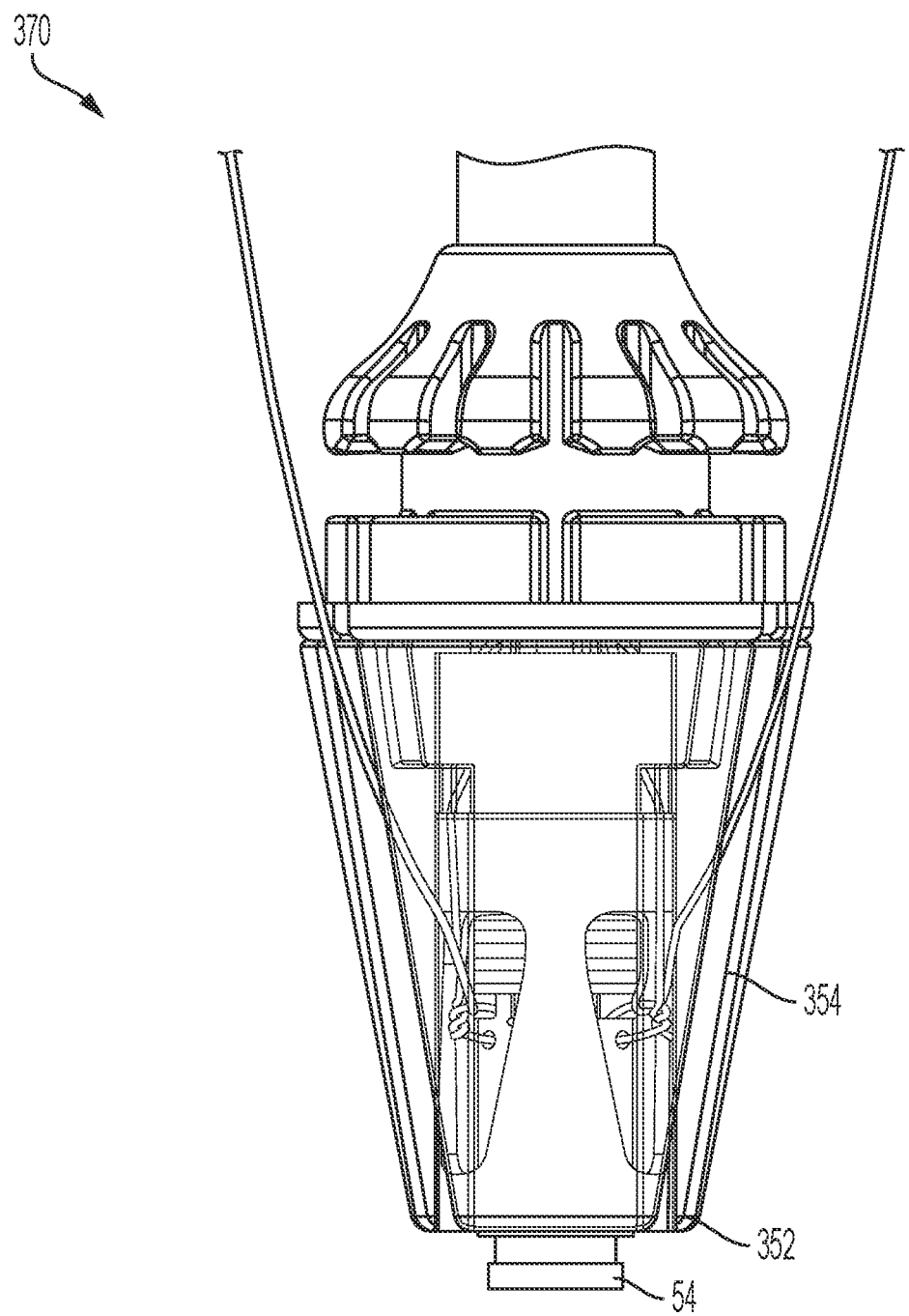
FIG. 65 is a perspective view of a lock delivery system with locking components.

The Lock Delivery System and Lock (FIGS. 64-65)

Figure 66:
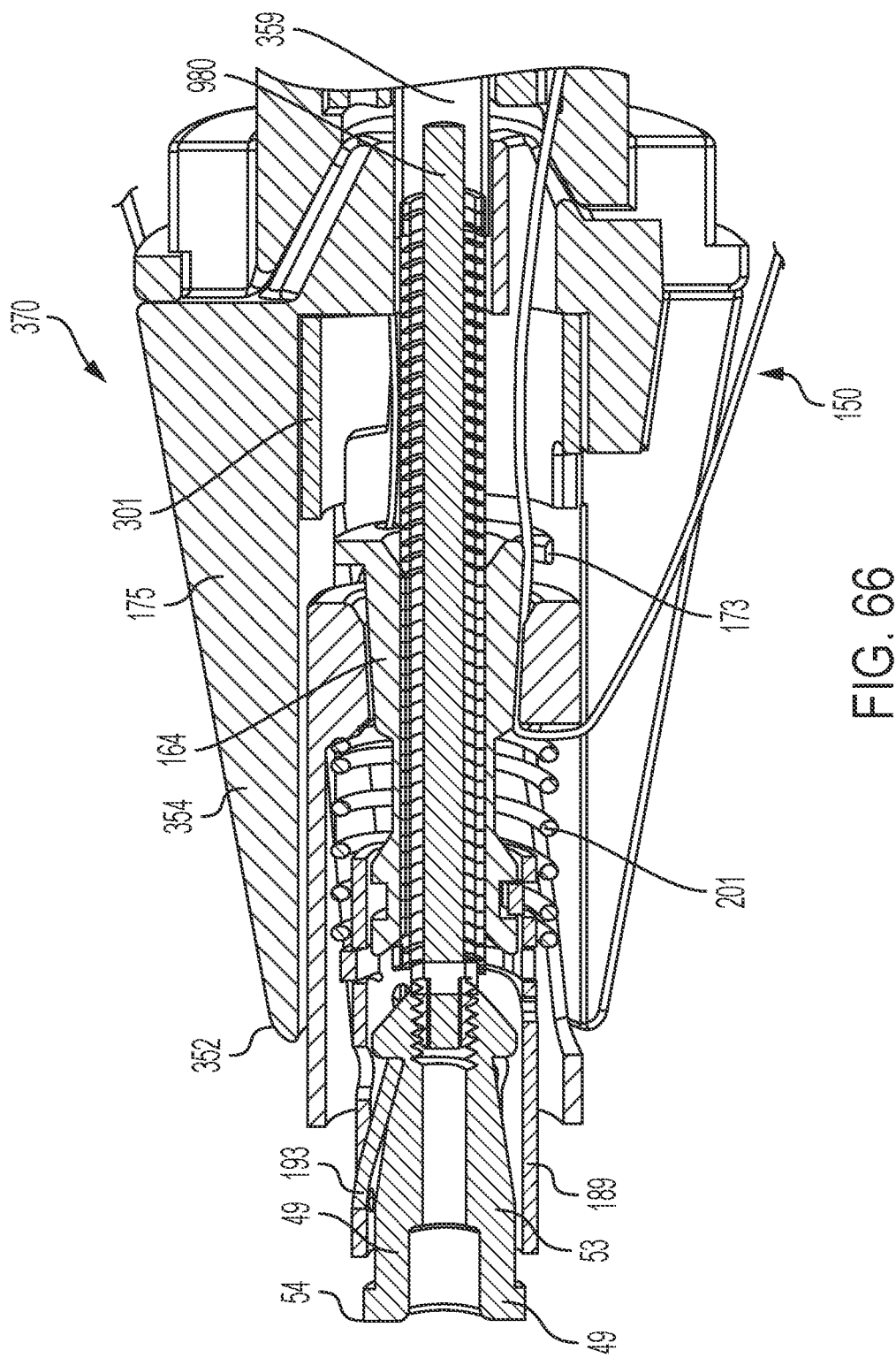
FIG. 66 is a cross-sectional side-elevational view of a lock delivery system with locking components and a tether with simplified routing.

Referring to FIGS. 64-65, are the lock delivery system/lock components 370. FIG. 66 shows the lock delivery system/lock components 370 with the standard routing of tether 150 as described above FIG. 64 shows all the components after the lock delivery system has gone over guidewire 900 and the tether swivel 188 has docked onto lock cap 49. In this aspect the end 54 of lock cap 49 has a larger diameter than lumen 357 (FIGS. 60-63), so the end 352 of the prosthesis delivery system cap 351 does not extend past end 54. The lumen 357 is large enough to accommodate the lock cap body 53 associated tether base 189 and at least one locking arm 93. As shown in cross-section in FIG. 64. part of at least one tether 150 extends along the tether cap slot 353. Within the lumen 357, the rest of the locking system 240 (FIG. 58) extends proximally. As shown in FIG. 64, the end 361 of lock collar controller 359 rests above the lock collar 175. The at least one tether 150 is configured and utilized as described above and the interbody segment 153 exits the tether alignment hole 173, creates loop 154, which is connected to loop 363 of the tether control line 362 (FIG. 60). The at least one tether control line 362, lock collar controller 359, and guidewire 900 extend proximally through the lock delivery system shaft 368, and all of these components exit the body and are connected to a lock delivery system controller (not shown).

Figure 67:
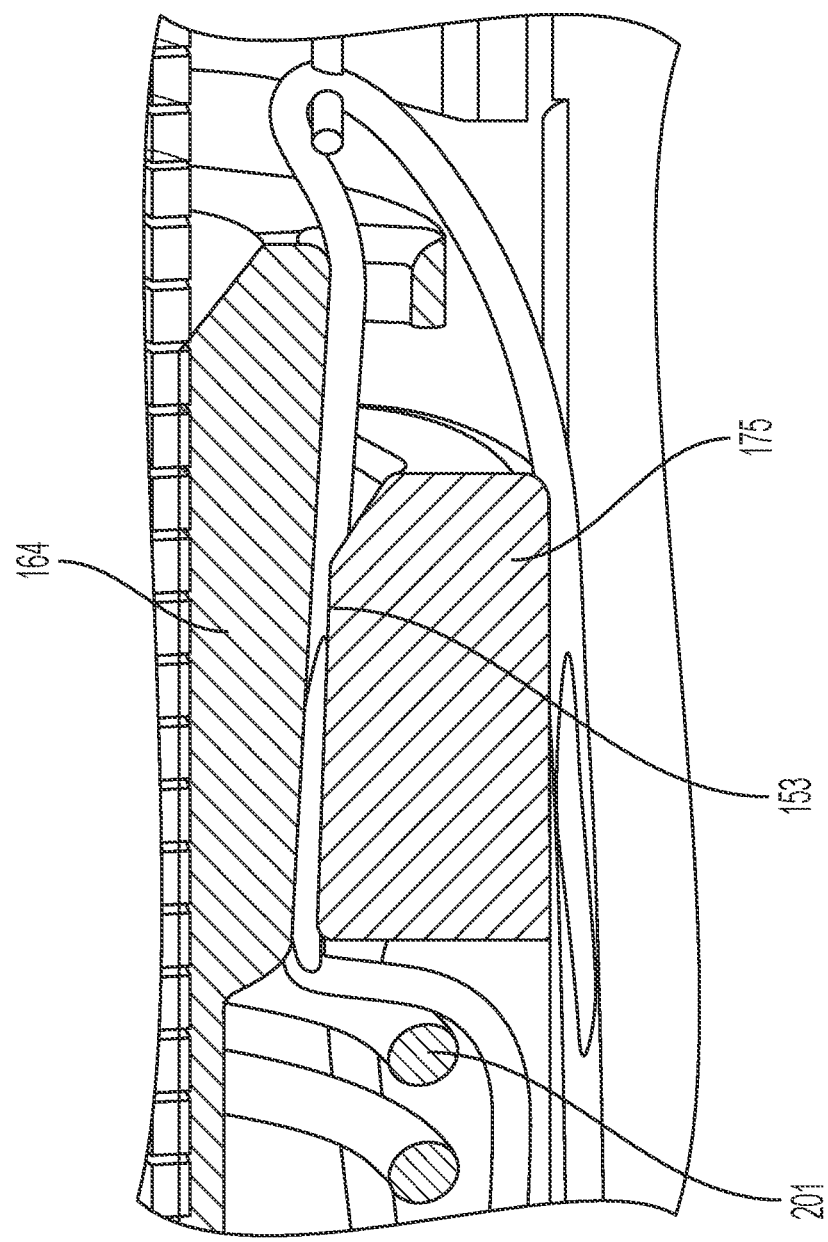
FIG. 67 is a magnified cut-away side elevational view of the tether locked.
Figure 68:
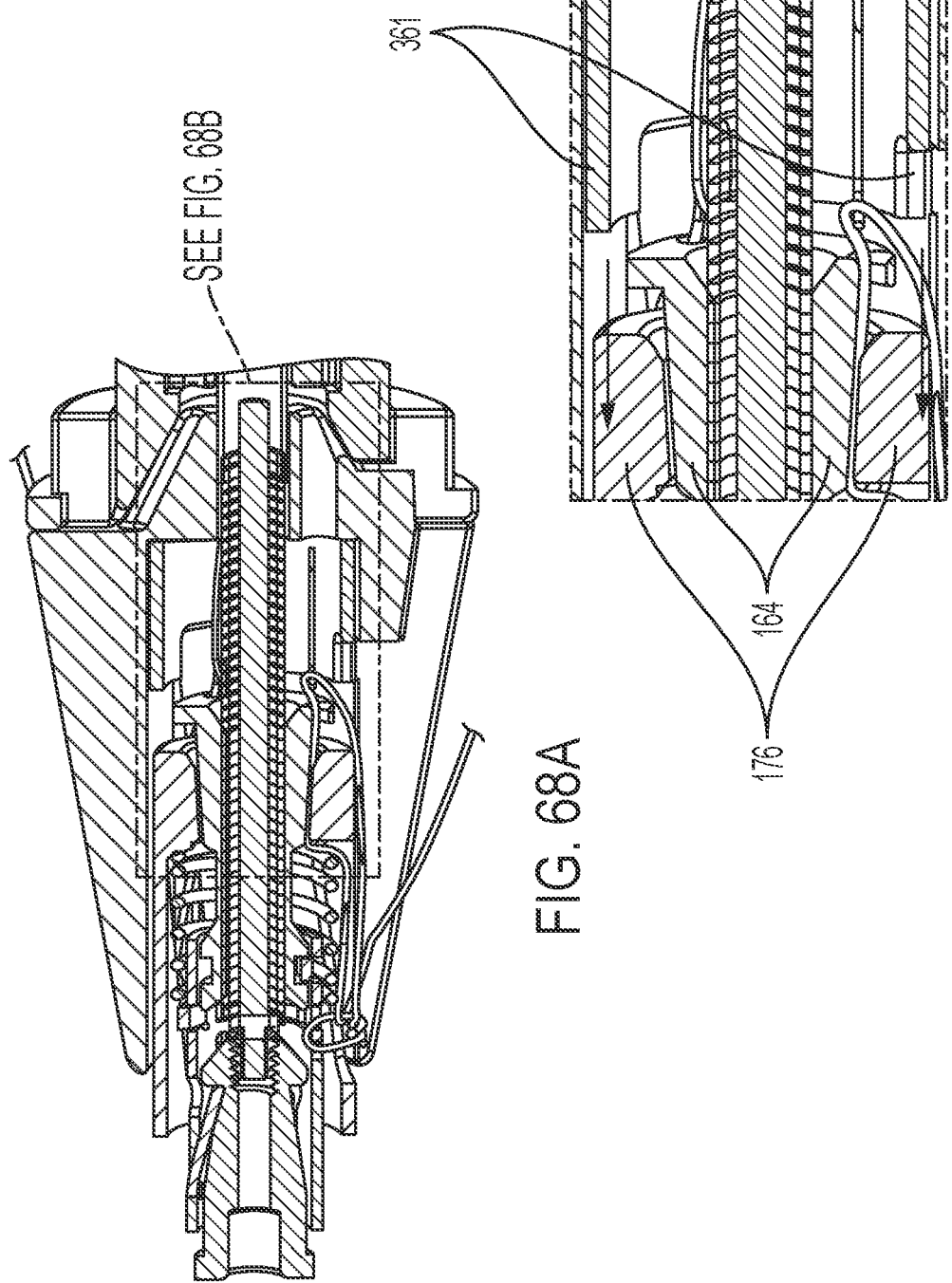
FIG. 68A is a cut-away side elevational view of the lock collar controller moving downwards to push the lock collar inferior to the lock cone so that the lock delivery system is in the unlocked position.
FIG. 68B is a magnified cut-away side elevational view of the lock collar controller moving downwards to push the lock collar inferior to the lock cone so that the lock delivery system is in the unlocked position.

Docking and Baseline Locked State (FIGS. 33-34, 67)

The same process of docking may occur as described in FIGS. 33-34). FIG. 64 shows the locking system in its baseline locked state. Specifically, the locking spring 201 is an expanded state, urging the lock collar 175 upwards with respect to the locking cone tapered surface 164, thereby pinching the interbody segment 153 of the tether 150, thereby fixing the length of the implant segment of the tether 151 of the tether 150. FIG. 67 is a magnified view of the interbody segment 153 being pinched by the lock collar 175, urged upwards by lock spring 201, and the locking cone tapered surface 164.

Unlocking Tether(s) (FIGS. 68-72)

Figure 69:
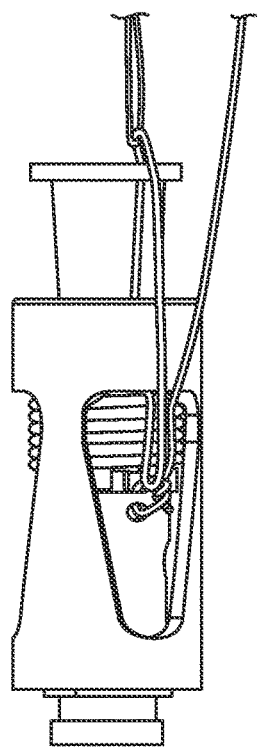
FIG. 69 is a side elevational view of the locking system in the locked position.
Figure 70:
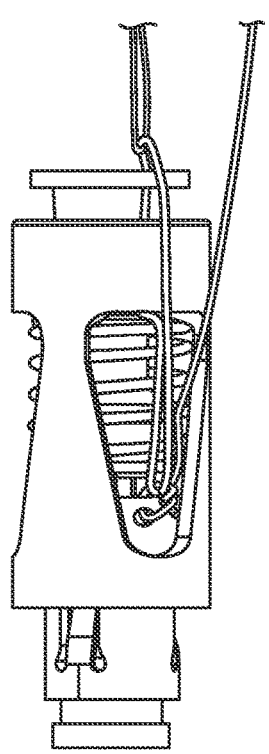
FIG. 70 is a side elevational view of the locking system in the unlocked position.
Figure 71:
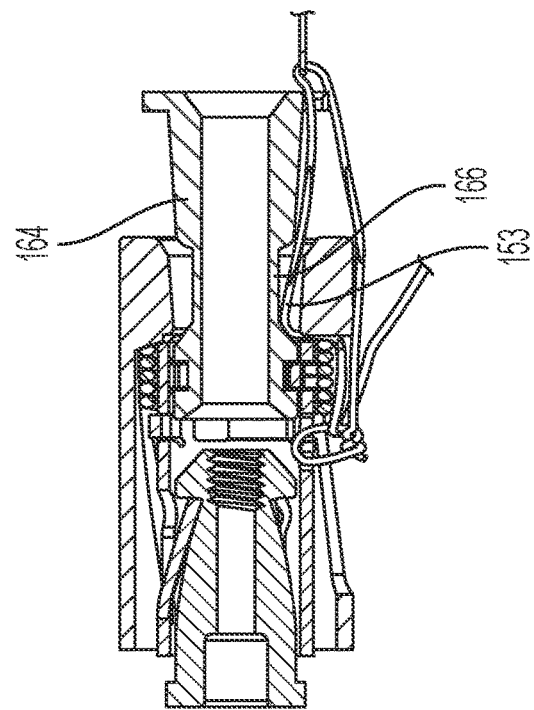
FIG. 71 is a cut-away side elevational view of the locking system in the locked position.
Figure 72:
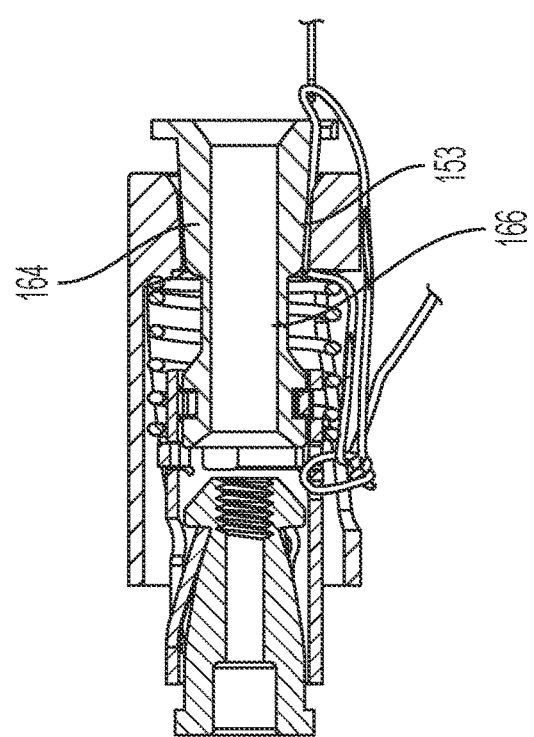
FIG. 72 is a cut-away side elevational view of the locking system in the unlocked position.

FIGS. 68-72 illustrate the step to unlock the system. Specifically, the lock collar controller 359 is pushed, and via its end 361, pushes the lock collar 175 inferior to the tapered surface 164 of the lock cone 163. As shown in FIGS. 68B, 69, and 71, at baseline the lock collar 175 is close to the top of the lock cone 163, minimizing the gap between the tapered surface 164 of the lock cone 163 and the internal wall of the lock collar 175, thereby trapping the interbody segment 153 of the tether 150. As shown in FIGS. 71-72, as the end 361 of the lock collar controller 359 pushes the lock collar 175 past the lock cone 163, the interbody segment 153 rests between internal wall of the lock collar 175 and the lock cone mid-section 166, thereby providing free space for the interbody segment 153 to translate freely.

Adjusting Tether(s) Length

Adjusting tether lengths with the alternative embodiment of the locking system occurs in the same manner as described for the first locking system above.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A minimally invasively implanted anchor support for securing a medical prosthesis device with a tether to an anchor implanted into a heart wall comprising:
   a lock cap having a distal end configured to be operatively connected to the anchor and a proximal end;
   a tether swivel having a proximal end and a distal end and defining a lumen configured to receive said proximal end of said lock cap;
   a lock cone having a distal end positioned within said tether swivel lumen proximally adjacent to said lock cap proximal end, said lock cone having a proximal portion having an outer surface defining a first lock cone mating surface, a second lock cone mating surface, and a lock cone lumen extending between said lock cone proximal and distal ends wherein said second lock cone mating surface is configured to cooperate with said tether swivel; and
   a lock collar comprising a lock collar body defining a lumen configured for receipt of said lock cone proximal end and said lock collar lumen comprises a lock collar mating surface configured to cooperate with said lock cone first mating surface to releasably secure the tether between said lock collar mating surface and said lock cone first mating surface.

2. The minimally invasively implanted anchor support according to claim 1 wherein said lock cone first mating surface is tapered and said lock collar mating surface is correspondingly tapered to mate with said lock cone first tapered surface.

3. The minimally invasively implanted anchor support according to claim 1 further comprising a tether for securing the medical device to said anchor support.

4. The minimally invasively implanted anchor support according to claim 3 wherein said lock cone includes a lock cone assembly hood positioned proximally to said lock cone groove.

5. The minimally invasively implanted anchor support according to claim 3 wherein said tether swivel includes at least one tether arm defining an eyelet wherein said tether includes an implant segment that extends distally through said eyelet of said tether arm wherein it then extends proximally from said eyelet and between said lock collar mating surface and said lock cone first mating surface.

6. The minimally invasively implanted anchor support according to claim 5 wherein said tether extends from between lock collar mating surface and said lock cone first mating surface proximally and reverses direction to extend distally forming a tether control loop.

7. The minimally invasively implanted anchor support according to claim 6 wherein said tether extends from said tether control loop distally to said eyelet.

8. The minimally invasively implanted anchor support according to claim 7 wherein said tether is configured into a knot adjacent said eyelet.

9. The minimally invasively implanted anchor support according to claim 3 wherein said tether includes an implant segment that extends distally and reverses direction through said lock collar mating surface and said lock cone first mating surface.

10. The minimally invasively implanted anchor support according to claim 9 wherein said tether extends from between lock collar mating surface and said lock cone first mating surface proximally and reverses direction to extend distally forming a tether control loop.

11. The minimally invasively implanted anchor support according to claim 1 wherein said tether swivel includes at least one locking arm configured to operatively cooperate with said second lock cone mating surface.

12. The minimally invasively implanted anchor support according to claim 11 wherein said second lock cone mating surface is a groove.

13. The minimally invasively implanted anchor support according to claim 11 wherein said at least one tether swivel locking arm is biased radially inwardly so as to cooperate with said lock cap.

14. The minimally invasively implanted anchor support according to claim 13 wherein said at least one tether swivel locking arm has a distal end adjacent said tether swivel distal end and a proximal end extending radially inward to cooperate with said lock cap.

15. The minimally invasively implanted anchor support according to claim 1 wherein said lock cap comprises a lock cap head on said proximal end and a lock cap body positioned between said lock cap distal end and said lock cap head wherein said lock cap head has a width greater than a width of said lock cap body.

16. The minimally invasively implanted anchor support according to claim 15 wherein said lock cap head is configured to cooperate with a guidewire.

17. The minimally invasively implanted anchor according to claim 16 wherein said lock cap head defines a threaded lumen for cooperating with said guidewire.

18. The minimally invasively implanted anchor support according to claim 15 wherein said tether swivel lumen is configured to receive said lock cap body and said lock cap distal end extends distally from said tether swivel lumen.

19. The minimally invasively implanted anchor according to claim 18 wherein said tether swivel lumen is configured to receive said lock cap head.

20. The minimally invasively implanted anchor support according to claim 15 wherein said lock cap distal end has a width greater than said lock cap body.

21. The minimally invasively implanted anchor support according to claim 15 wherein said lock cap body is tapered having a larger distal end adjacent said lock cap distal end and narrower proximal end adjacent said lock cap head.

22. The minimally invasively implanted anchor support according to claim 1 wherein said tether swivel includes a tubular body, a tether swivel distal base, at least one tether connector configured to operatively cooperate with a tether for connecting the medical device to the tether swivel.

23. The minimally invasively implanted anchor support according to claim 22 wherein said at least one tether connector is a tether eyelet.

24. The minimally invasively implanted anchor support according to claim 22 wherein said at least one tether connector is a tether arm extending radially outward from said tether swivel body.

25. The minimally invasively implanted anchor support according to claim 24 wherein said at least one tether arm extends radially outward from said tether swivel tubular body.

26. The minimally invasively implanted anchor support according to claim 25 wherein said at least one tether arm includes a distal end adjacent said tether swivel distal base and a proximal end, said tether arm proximal end defining an eyelet configured to receive the tether.

27. The minimally invasively implanted anchor support according to claim 26 wherein said eyelet defines an aperture.

28. The minimally invasively implanted anchor support according to claim 22 wherein said tether swivel tubular body is defined by at least one longitudinally extending shaft column adjacent said at least one tether arm.

29. The minimally invasively implanted anchor support according to claim 28 wherein said tether swivel further includes a coupling arm extending from the proximal end of said shaft column wherein said coupling arm is flexible radially inwardly to cooperate with said lock cone second mating surface.

30. The minimally invasively implanted anchor support according to claim 22 wherein said tether swivel tubular body further defines a locking arm and a locking arm aperture wherein said locking arm is moveable between a first unlocked and a second locked position when said locking arm cooperates with said second lock cone mating surface.

31. The minimally invasively implanted anchor support according to claim 22 wherein said tether swivel tubular body defines a lumen extending between said tether swivel proximal end and distal end.

32. The minimally invasively implanted anchor support according to claim 22 wherein said tether swivel further comprises a shaft collar adjacent a proximal end of said shaft column wherein said shaft collar extends circumferentially around said tether swivel proximal end.

33. The minimally invasively implanted anchor support according to claim 1 wherein said tether swivel further comprises swivel distal base having a first width and said lock cap distal end has second width wherein said lock cap second width is greater than said tether swivel first width.

34. The minimally invasively implanted anchor support according to claim 1 wherein said lock collar includes at least one lock collar connector defining a connector lumen having an open upper proximal end and configured for receipt of a lock collar control rod to move said lock collar.

35. The minimally invasively implanted anchor support according to claim 34 wherein said connector lumen defines a threaded portion and said lock collar control rod has a threaded distal end for releasably mating with said lock collar connector lumen.

36. The minimally invasively implanted anchor support according to claim 35 wherein said tether swivel further comprises at least one tether arm configured to operatively cooperate with a tether for connecting the medical device to the tether swivel and said spring is positioned radially inward from said at least one tether arm on said tether swivel tubular body.

37. The minimally invasively implanted anchor support according to claim 34 wherein said at least one lock collar connector includes at least two of said lock collar connectors.

38. The minimally invasively implanted anchor support according to claim 1 wherein said tether swivel includes a tubular body and said anchor support further comprises a locking spring positioned around said tubular body for biasing said lock collar proximally.

39. The minimally invasively implanted anchor support according to claim 38 wherein said spring is a helical spring.

40. The minimally invasively implanted anchor support according to claim 38 wherein said spring is a wave spring.

41. The minimally invasively implanted anchor support according to claim 1 wherein said tether swivel includes a tubular body and a tether swivel distal base wherein said tether swivel base is greater in width than said tether swivel tubular body and said anchor support further comprises a lock delivery system for delivering said tether swivel to said lock cap, said lock delivery system comprising a prosthesis delivery cap having a proximal and distal end and a lumen extending between said delivery cap proximal and distal ends wherein said lumen is configured and has a diameter to receive said lock cap, said tether swivel proximal end, said lock cone and said lock collar.

42. The minimally invasively implanted anchor support according to claim 41 wherein said tether swivel base width is greater than said delivery cap lumen diameter.

43. The minimally invasively implanted anchor support according to claim 41 wherein tether swivel includes a tubular body and at least one tether arm configured to operatively cooperate with a tether for connecting the medical device to the tether swivel and said delivery cap includes at least one tether arm groove for receiving said at least one tether arm of said tether swivel.

44. The minimally invasively implanted anchor support according to claim 41 where said delivery cap distal end is open to said delivery cap lumen for receipt of said anchor cap and said delivery cap proximal end includes a guidewire aperture and at least one tether collar hole and said livery system comprises at least one tether collar control rod configured for receipt by said at least one tether collar hole.

45. The minimally invasively implanted anchor support according to claim 1 wherein said lock collar includes at least one control rod guide defining an aperture and at least one control rod wherein said at least one control rod is selectively received within said rod guide aperture.

46. The minimally invasively implanted anchor support according to claim 45 wherein said lock collar comprises a stabilizer positioned distally from said rod guide aperture for limiting distal movement of said at least one control rod.

47. The minimally invasively implanted anchor support according to claim 46 wherein said control rod includes a proximal shaft and a distal end including a limiter tab for cooperating with said stabilizer.

48. The minimally invasively implanted anchor support according to claim 47 wherein said lock collar comprises a limiting rod positioned for cooperating with said limiter tab for limiting rotational movement of said control rod.

49. The minimally invasively implanted anchor support according to claim 1 wherein said lock collar is positioned proximally to said tether swivel proximal end.

50. The minimally invasively implanted anchor support according to claim 1 wherein said lock collar defines said tether swivel proximal end.

51. The minimally invasively implanted anchor support according to claim 50 wherein said tether swivel includes a shaft body and at least one locking arm configured to operatively cooperate wherein said locking arm is moveable between a first unlocked and a second locked position when said locking arm cooperates with said second lock cone mating surface.

52. The minimally invasively implanted anchor support according to claim 50 wherein said lock collar includes at least one coupling arm for cooperating with said first lock cone mating surface.

53. The minimally invasively implanted anchor support according to claim 50 wherein said lock collar includes at least one spring contact tab and said anchor support further comprises a spring positioned on said tether swivel distal to said lock collar for biasing said lock collar proximally.

54. The minimally invasively implanted anchor support according to claim 50 wherein said anchor support further comprises a tether operatively connected to said tether swivel shaft body.

55. The minimally invasively implanted anchor support according to claim 25 wherein said at least one tether arm comprises at least two tether arms.

56. The minimally invasively implanted anchor support according to claim 55 wherein said at least one tether arm comprises at three tether arms.

57. A method of invasively and endovascularly implanting an anchor support for securing a medical prosthesis device with a tether to an anchor implanted into body tissue comprising a lock cap having a distal end configured to be operatively connected to the anchor and a proximal end; a tether swivel having a proximal end and a distal end and defining a lumen configured to receive said proximal end of said lock cap; a lock cone having a distal end positioned within said tether swivel lumen proximally adjacent to said lock cap proximal end, said lock cone having a proximal portion having an outer surface defining a first lock cone mating surface, a second lock cone mating surface, and a lock cone lumen extending between said lock cone proximal and distal ends wherein said second lock cone mating surface is configured to cooperate with said tether swivel; a lock collar comprising a lock collar body defining a lumen configured for receipt of said lock cone proximal end and said lock collar lumen comprises a lock collar mating surface configured to cooperate with said lock cone first mating surface to releasably secure the tether between said lock collar mating surface and said lock cone first mating surface; a tether; and a lock delivery system wherein said method includes the steps of:

endovascularly implanting the lock cap and securing the lock cap to an anchor for anchoring the anchor support and medical prosthesis to body tissue;

endovascularly implanting a guidewire connected to the lock cap proximal end;

delivering endovascularly the tether swivel, lock cone, lock collar, and locking the tether swivel to the lock cap by advancing the lock delivery system of the guidewire;

applying distal movement of the tether swivel onto the anchor cap wherein the tether swivel locks onto the anchor cap and wherein the tether is locked extends from between lock collar mating surface and said lock cone first mating surface and reversibly locked therebetween.

58. The method according to claim 57 wherein said method further includes the step of securing the tether to the tether swivel.

* * * * *